(12) United States Patent
Henderson et al.

(10) Patent No.: US 6,436,394 B1
(45) Date of Patent: Aug. 20, 2002

(54) ADENOVIRUS VECTORS SPECIFIC FOR CELLS EXPRESSING ANDROGEN RECEPTOR AND METHODS OF USE THEREOF

(75) Inventors: Daniel R. Henderson; Eric R. Schuur, both of Palo Alto; De-Chao Yu, Foster City, all of CA (US)

(73) Assignee: Cell Genesys, Inc., Foster City, CA (US)

( * ) Notice: Subject to any disclaimer, the term of this patent is extended or adjusted under 35 U.S.C. 154(b) by 0 days.

(21) Appl. No.: 09/614,495

(22) Filed: Jul. 11, 2000

Related U.S. Application Data

(63) Continuation of application No. 09/033,333, filed on Mar. 2, 1998.
(60) Provisional application No. 60/039,762, filed on Mar. 3, 1997.

(51) Int. Cl.[7] .................. A61K 48/00; C12N 15/861; C12N 5/10; C12N 15/63
(52) U.S. Cl. .................. 424/93.2; 435/320.1; 435/325; 435/366; 435/455; 435/456; 435/457; 435/371; 435/369; 424/93.1; 424/93.6
(58) Field of Search .................. 435/320.1, 235.1, 435/325, 366, 455, 456, 457, 371, 369; 424/93.1, 93.2, 93.6

(56) References Cited

U.S. PATENT DOCUMENTS

| | | | |
|---|---|---|---|
| 4,893,623 A | 1/1990 | Rosenbluth et al. | |
| 5,007,437 A | 4/1991 | Sterzer et al. | |
| 5,344,435 A | 9/1994 | Turner et al. | |
| 5,516,771 A | 5/1996 | Dionne | |
| 5,527,336 A | 6/1996 | Rosenbluth et al. | |
| 5,569,667 A | 10/1996 | Grove et al. | |
| 5,648,478 A | 7/1997 | Henderson | |
| 5,698,443 A | * 12/1997 | Henderson et al. | ...... 435/320.1 |
| 5,783,681 A | 7/1998 | Matusik | |
| 5,998,205 A | 12/1999 | Hallenbeck | |
| 6,197,293 B1 | * 3/2001 | Henderson et al. | ......... 424/93.2 |

FOREIGN PATENT DOCUMENTS

| | | |
|---|---|---|
| WO | WO 94/03594 | 2/1994 |
| WO | WO 95/00655 A1 | 1/1995 |
| WO | WO 95/11984 | 5/1995 |
| WO | WO 96/17053 | 6/1996 |
| WO | WO 96/34969 | 11/1996 |
| WO | WO 97/01358 | 1/1997 |
| WO | WO 98/35028 | 8/1998 |

OTHER PUBLICATIONS

Tollefson et al., J. Virol, vol. 70, No. 4, pp. 2296–2306, Apr. 1996.

Greenberg et al., Molecular Endocrinology, vol. 8(2), pp. 230–239, 1994.

Bischoff et al. (1996). "An adenovirus mutant that replicates selectively in p53–deficient human tumor cells," Science 274(5286):373–376.

Rodriguez et al. (1997). "Prostate attenuated replication competent adenovirus (ARCA) CN706: A selective cytotoxic for prostate–specific antigen–positive prostate cancer cells," Cancer Res. 57: 2559–2563.

Swaminathan et al. (1995). "Regulation of adenovirus E2 transcription unit," Curr. Top. Microbiol. Immunol. (Pt. 3):177–194.

Wills et al. (1995). "Gene therapy for hepatocellular carcinoma: chemosensitivity conferred by adenovirus–mediated transfer of the HSV–1 thymidine kinase gene," Cancer Gene Ther. 2:191–197.

Adair et al., "Targeted homologous recombination at the endogenous adenine phosphoribosyltransferase locus in chinese hamster cells" Proc. Natl. Acad. Sci. USA 86:4574–4578 (1989).

Adler et al., "Multiple components of a complex androgen–dependent enhancer" Molec. Endocrinol. 5:1587–1596 (1991).

Arnberg et al., "Fiber genes of adenoviruses with tropism for the eye and the genital tract" Virol. 227:239–244 (1997).

Bailey et al., "Enteric adenovirus type 40: Expression of E1B proteins in Vitro and in Vivo" Virol 193:631–641 (1993).

Bailey et al., "Cell type specific regulation of expression from the Ad40 E1B promoter in recombinant Ad5/Ad40 Viruses" Virol. 202:695–706 (1994).

Behringer et al., "Dwarf mice produced by genetic ablation of growth hormone–expressing cells" Genes Dev. 2:453–461 (1988).

(List continued on next page.)

*Primary Examiner*—David Guzo
(74) *Attorney, Agent, or Firm*—Linda Judge, Esq.; Pamela J. Sherwood; Bozicevic, Field & Francis LLP

(57) ABSTRACT

Replication-competent adenovirus vectors specific for cells which allow a probasin transcriptional response element (PB-TRE) to function, such as cells which express the androgen receptor (AR), and methods of use of such viruses are provided. These viruses comprise and adenoviral gene under control of a transcription regulatory portion of a PB-TRE, which is in turn dependent upon AR expression. The gene can be, for example, a gene required for viral replication or the adenovirus death protein gene (ADP). The viruses can also comprise at least one additional adenoviral gene under control of at least one additional prostate-specific transcriptional response element, such as that controlling prostate-specific antigen expression (PSA-TRE). Thus, virus replication can be restricted to target cells exhibiting prostate-specific gene expression, particularly prostate carcinoma cells. An adenovirus of the present invention can further comprise a heterologous gene such as a reporter under transcriptional control of a PB-TRE. The adenovirus vectors can be used to detect and monitor samples for the presence of prostate cells as well as to selectively kill malignant cells producing prostate-specific gene products.

26 Claims, 11 Drawing Sheets

OTHER PUBLICATIONS

Berkner, K.L. and Sharp, P.A. "Generation of adenovirus by transfection of plasmids" Nucleic Acids Res. 11(17):6003–6020 (1983).

Bett et al., "Packaging capacity and stability of human adenovirus type 5 vectors" J. Virol. 67(10):5911–5921 (1993).

Bett et al., "An efficient and flexible system for construction of adenovirus vectors with insertions or deletions in early regions 1 and 3" Proc. Natl. Acad. Sci. USA 91:8802–8806 (1994).

Blok et al., "Follicle–stimulating hormone regulates androgen receptor mRNA in Sertoli cells" Molec. Cell. Endocrinol. 63:267–271 (1989).

Blok et al., "Transcriptional regulation of androgen receptor gene expression in Sertoli cells and other cell types" Molec. Cell. Endocrinol. 88:153–164 (1992).

Boulikas, T., "Gene therapy of prostate cancer: p53, suicidal genes, and other targets" Anticancer Res. 17:1471–1505 (1997).

Braun, R.P. and Lee, J.S., "Immunogenic duplex nucleic acids are nuclease resistant" J. Immunol. 141(6):2084–2089 (1988).

Bridge, E. and Ketner, G., "Redundant control of adenovirus late gene expression by early region 4" J. Virol. 63(2):631–638 (1989).

Burnstein et al., "Androgen and glucocorticoid regulation of androgen receptor cDNA expression" Molec. Cell. Endocrinol. 115:177–186 (1995).

Buzek, S.W. and Sanborn, B.M., "Increase in testicular androgen receptor during sexual maturation in the rat" Biol. Reprod. 39:39–49 (1988).

Capecchi, M.R., "Altering the genome by homologous recombination" Science 244:1288–1292 (1989).

Carson–Jurica et al., "Steroid receptor family: Structure and functions" Endocrinol. Rev. 11(2):201–220 (1990).

Chan et al., "Steroid Hormone Action" in: Pediatric Endocrinology, Collu et al., eds., pp. 81–124, Raven Press, New York (1989).

Chang et al., "Cancer Gene Therapy Using Novel Tumor Specific Replication Competent Adenoviral Vectors" Cold Spring Harbor Gene Therapy Meeting, p. 53 (1996).

Chang et al., "Structural analysis of complementary DNA and amino acid sequences of human and rat androgen receptors".Proc. Natl. Acad. Sci. USA 85:7211–7215 (1988).

Chaturvedi et al., "Stabilization of triple–stranded oligonucleotide complexes: Use of probes containing alternating phosphodiester and stereo–uniform cationic phosporamidate linkages" Nucleic Acids Res. 24(12):2318–2323 (1996).

Claessens et al., "Functional characterization of an androgen response element in the first intron of the C3(1) gene of prostatic binding protein" Biochem. Biophys. Res. Comm. 164:833–840 (1989).

Current Protocols in Molecular Biology (Ausubel et al., eds.), Supp. 30, pp. 7.7.18–7.7.19, Table 7.7.1 (1987).

Dai, J.L. and Burnstein, K.L., "Two androgen response elements in the androgen receptor coding region are required for cell–specific up–regulation of receptor messenger RNA" Molec. Endocrinol. 10:1582–1594 (1996).

Dai et al., "Androgenic up–regulation of androgen receptor cDNA expression in androgen–independent prostate cancer cells" Steroids 61:531–539 (1996).

De Vos et al., "Interaction of the androgen response elements with the DNA–binding domain of the rat androgen receptor expressed in *Escherichia coli*" J. Biol. Chem. 266:3439–3443 (1991).

Dodd et al., "Characterization and cloning of rat dorsal prostate mRNAs" J. Biol. Chem. 258(17):10731–10737 (1983).

Felgner, P.L. and Ringold, G.M., "Cationic liposome–mediated transfection" Nature 337:387–388 (1989).

Flint, S.J., "Expression of adenoviral genetic information in productively infected cells" Biochem. Biophys. Acta 651:175–208 (1982).

Flint, S.J., "Regulation of adenovirus mRNA formation" Adv. Virus Res. 31:169–228 (1986).

Foster et al., "Characterization of prostatic epithelial cell lines derived from transgenic adenocarcinoma of the mouse prostate (tramp) model" Cancer Res. 57:3325–3330 (1997).

Frankel et al., "Selection and characterization of ricin toxin A–chain mutations in *Saccharomyces cerevisiae*" Molec. Cell. Biol. 9(2):415–420 (1989).

Goodrum, F.D. and Ornelles, D.A., "The early region 1B 55–Kilodalton oncoprotein of adenovirus relieves growth restrictions imposed on viral replication by the cell cycle" J. Virol. 71:548–561 (1997).

Graham, F.L., "Covalently closed circles of human adenovirus DNA are infectious" EMBO J 3(12):2917–2922 (1984).

Graham, F.L., "Growth of 293 cells in suspension culture" J. Gen. Virol. 68:937–940 (1987).

Graham, F.L. and Van Der Eb, A.J., "A new technique for the assay of infectivity of human adenovirus 5 DNA" Virol. 52:456–467 (1973).

Graham et al., "Characteristics of a human cell line transformed by DNA from human adenovirus type 5" J. Gen. Virol 36:59–72 (1977).

Grand, R.J.A., "The structure and functions of the adenovirus early region 1 proteins" Biochem. J. 241:25–38 (1987).

Greenberg et al., "Prostate cancer in transgenic mouse" Proc. Natl. Acad. Sci. 92:3439–3443 (1995).

Grootegoed et al., "Absence of a nuclear androgen receptor in isolated germinal cells of rat testis" Molec. Cell. Endocrinol. 9:159–157 (1977).

Hallenbeck, P.L. et al., "Novel Tumor Specific Replication Competent Adenoviral Vectors for Gene Therapy of Cancer" Abstract No. O–36 Cancer Gene Therapy 3(6):S19–S20 (1996).

Hayashi et al., "Expression of a thyroid hormone–responsive recombinant gene introduced into adult mice livers by replication–defective adenovirus can be regulated by endogenous thyroid hormone receptor" J. Biol. Chem. 269(39):23872–23875 (1994).

Huber et al., "VDEPT: An enzyme/prodrug gene therapy approach for the treatment of metastatic colorectal cancer" Adv. Drug Delivery Reviews 17:279–292 (1995).

Jaffe et al., "Adenovirus–mediated in vivo gene transfer and expression in normal rat liver" Nature Genetics 1:372–378 (1992).

Johnson et al., "Characterization of the androgen receptor" in: Steroid Receptors and Disease (Sheridan, ed.), pp. 207–228, Dekker, New York (1988).

Johnson et al., "Targeting of nonexpressed genes in embryonic stem cells via homologous recombination" Science 245:1234–1236 (1989).

Lamb et al., "Nucleotide sequence of cloned cDNA coding for preproricin" Eur. J. Biochem. 148:265–270 (1985).

Latimer et al., "Specificity of monoclonal antibodies produced against phosphorothioate and ribo modified DNAs" Molec. Immunol. 32:1057–1064 (1995).

Le Gal La Salle et al., "An adenovirus vector for gene transfer into neurons and glia in the brain" Science 259:988–990 (1993).

Lindzey et al., "Molecular mechanisms of androgen action" Vitamins and Hormones 49:383–432 (1994).

Lubahn et al., "The human androgen receptor: Complementary deoxyribonucleic acid cloning, sequence analysis and gene expression in prostate" Molec. Endocrinol. 2:1265–1275 (1988).

Lundwall, A., "Characterization of the gene for prostate–specific antigen, a human glandular kallikrein" Biochim. Biophys. Res. Commun. 161(3):1151–1159 (1989).

Lundwall, A. and Lilja, H., "Molecular cloning of human prostate specific antigen cDNA" FEBS Lett. 214(2):317–322 (1987).

Mansour et al., "Disruption of the proto–oncogene int–2 in mouse embryo–derived stem cells: A general strategy for targeting mutations to non–selectable genes" Nature 336:348–352 (1988).

Mastrangeli et al., "Diversity of airway epithelial cell targets for in Vivo recombinant adenovirus–mediated gene transfer" J. Clin. Invest. 91:225–234 (1993).

Matusik et al., "Regulation of prostatic genes: Role of androgens and zinc in gene expression" Biochem. Cell. Biol. 64:601–607 (1986).

Maxwell et al., "Cloning, sequence determination, and expression in transfected cells of the coding sequence for the tox 176 attenuated diptheria toxin A chain" Molec. Cell. Biol. 7(4):1576–1579 (1987).

McKinnon et al., "Tn5 mutagenesis of the transforming genes of human adenovirus type 5" Gene 19:33–42 (1982).

Messing et al., "P.sub.0 promoter directs expression of reporter and toxin genes to Schwann cells of transgenic mice" Neuron 8:507–520 (1992).

Mocellini et al., "Finasteride (MK–906) in the treatment of benign prostatic hyperplasia" Prostate 22:291–299 (1993).

Morris, B.J., "hGK–1: A Kallikrein gene expressed in human prostate" Clin. Exp. Pharm. Physiol. 16:345–351 (1989).

Murtha et al., "Androgen induction of a human prostate–specific kallikrein, hKLK2: Characterization of an androgen response element in the 5' promoter region of the gene" Biochem. 32:6459–6464 (1987).

Nastiuk, K.L. and Clayton, D.F., "Seasonal and tissue–specific regulation of canary androgen receptor messenger ribonucleic acid" Endorcinol. 134:640–649 (1994).

Nevins, J.R., "Mechanisms of viral–mediated trans–activation of transcription" Adv. Virus Res. 31:35–83 (1989).

Palmiter et al., "Cell lineage ablation in transgenic mice by cell–specific expression of a toxin gene" Cell 50:435–443 (1987).

Peyrottes et al., "Oligodeoxynucleoside phosphoramidates (P–NH.sub.2) Synthesis and thermal stability of duplexes with DNA and RNA targets" Nucleic Acids Res. 24:1841–1848 (1996).

Piatak et al., "Expression of soluble and fully functional ricin A chain in *Escherichia coli* is temperature–sensitive" J. Biol. Chem. 263:4837–4843 (1988).

Prins, G.S. and Woodham, C., "Autologous regulation of androgen receptor messenger ribonucleic acid in the separate lobes of the rat prostate gland" Biol. Reprod. 53:609–619 (1995).

Quantin et al., "Adenovirus as an expression vector in muscle cells in vivo" Proc. Natl. Acad. Sci. USA 89:2581–2584 (1992).

Quarmby et al., "Autologous down–regulation of androgen receptor messenger ribonucleic acid" Molec. Endocrinol. 4:22–28 (1990).

Qiu et al., "In situ hybridization of prostate–specific antigen mRNA in human prostate" J. Urology 144:1550–1556 (1990).

Ragot et al., "Efficient adenovirus–mediated transfer of a human minidystrophin gene to skeletal muscle of mdx mice" Nature 361:647–650 (1993).

Rennie et al., "Characterization of two cis–acting DNA elements involved in the androgen regulation of the probasin gene" Molec. Endocrinol. 7:23–36 (1993).

Riegman et al., "The promoter of the prostate–specific antigen gene contains a functional androgen responsive element" Molec. Endocrinol. 5(12):1921–1930 (1991).

Rosenfeld et al., "In vivo transfer of the human cystic fibrosis transmembrane conductance regulator gene to the airway epithelium" Cell 68:143–155 (1992).

Rosenfeld et al., "Adenovirus–mediated transfer of a recombinant .alpha.1–antitrypsin gene to the lung epithelium in vivo" Science 252:431–434 (1991).

Schedlich et al., "Primary structure of a human glandular kallikrein gene" DNA 6(5):429–437 (1987).

Schultz et al., "Oligo–2'–fluoro–2'–deoxynucleotide N3'.fwdarw.P5' phosphoramidates: Synthesis and properties" Nucleic Acids Res. 24:2966–2973 (1996).

Schuur et al., "Prostate specific antigen expression is regulated by an upstream enhancer" J. Biol. Chem. 271:7043–7051 (1996).

Shan et al., "Quantitative analysis of androgen receptor messenger ribonucleic acid in developing Leydig cells and Sertoli cells by in situ hybridization" Endocrinol. 136:3856–3862 (1995).

Snoek et al., "Induction of cell–free, in Vitro transcription by recombinant androgen receptor peptides" J. Steroid Biochem. Molec. Biol. 59:243–50 (1996).

Stratford–Perricaudet et al., "Widespread long–term gene transfer to mouse skeletal muscles and heart" J. Clin. Invest. 90:626–630 (1992).

Stratford–Perricaudet et al., "Evaluation of the transfer and expression in mice of an enzyme–encoding gene using a human adenovirus vector" Human Gene Therapy 1:241–256 (1990).

Swaminathan, S. and Thimmapaya, B., "Regulation of adenovirus E2 transcription unit" Curr. Topics in Microbiol. Immunol. 199(part 3):177–194 (1995).

Sweetland et al., "Post–castration rebound of an androgen regluated prostatic gene" Molec. Cell. Biochem. 84:3–15 (1988).

Takiff et al., "Propagation and in vitro studies of previously non–cultivable enteral adenoviruses in 293 cells" The Lancet 11:832–834 (Oct. 17, 1981).

Tilley et al., "Characterization and expression of a cDNA encoding the human androgen receptor" Proc. Natl. Acad. Sci. USA 86:327–331 (1989).

Tollefson et al., "The 11,600–M.sub.w protein encoded by region E3 of adenovirus is expressed early but is greatly amplified at late stages of infection" J. Virol. 66(6):3633–3642 (1992).

Trapman et al., "Cloning, structure and expression of a cDNA encoding T receptor" Biochem. Biophys. Res. Comm. 153:241–248 (1988).

Verhoeven, G. and Cailleau, J., "Follicle–stimulating hormone and androgens increase the concentration of the androgen receptor in Sertoli cells" Endocrinol. 122:1541–1550 (1988).

Verma, I.M. and Somia, N., "Gene Therapy: Promises, problems and prospects" Nature 389:239–242 (1997).

Virtanen et al., "mRNAs from human adenovirus 2 early region 4" J. Virol. 51(3):822–831 (1984).

Wang et al., "Expression of the APRT gene in an adenovirus vector system as a model for studying gene therapy" Adv. Exp. Med. Biol. 309:61–66 (1991).

Weinberg, D.H. and Ketner, G., "A cell line that supports the growth of a defective early region 4 deletion mutant of human adenovirus type 2" Proc. Natl. Acad. Sci. USA 80:5383–5386 (1983).

Wolf et al., "Transcriptional regulation of prostate kallikrein–like genes by androgen" Molec. Endocrinol. 6:753–762 (1992).

Wolf et al., "Transcriptional and posttranslational regulation of human androgen receptor expression by androgen" Molec. Endocrinol. 7:924–936 (1993).

Young et al., "Tissue–specific and hormonal regulation of human prostate–specific glandular kallikrein" Biochem. 31(3):818–824 (1992).

Zhang et al., "Identification of two novel cis–elements in the promoter of the prostate–specific antigen gene that are required to enhance androgen receptor–mediated transactivation" Nucleic Acids Res. 25(15):3143–3150 (1997).

Zhou et al., "The androgen receptor: An overview" Recent Prog. Hormone Res. 49:249–274 (1994).

Zjilstra et al., "Germ–line transmission of a disrupted .beta..sub.2 –microglobulin gene produced by homologous recombination in embryonic stem cells" Nature 342:435–438 (1989).

* cited by examiner

-426

5'-AAGCTTCCACAAGTGCATTTAGCCTCTCCAGTATTGCTGATGAATCCACAGT

TCAGGTTCAATGGCGTTCAAAACTTGATCAAAAATGACCAGACTTTATATTCTTA

CACCAACATCTATCTGATTGGAGGAATGGATAATAGTCATCATGTTTAAACATCT

ACCATTCCAGTTAAGAAAATATGATAGC<u>ATCTTGTTCTTAGT</u>CTTTTTCTTAATA
                                         ARE-1

GGGACATAAAGCCCACAAATAAAAATATGCCTGAAGAATGGGACAGGCATTGG

GCATTGTCCATGCCTA<u>GTAAAGTACTCCAAGAACCTATTT</u>GTATACTAGATGACA
                ARE-2

CAATGTCAATGTCTGTGTACAACTGCCAACTGGGATGCAAGACACTGCCCATG

+1
|CCAAT|CATCCTGAAAAGCAGC|TATAAAAA|GCAGGAAGCTACTCTGCAC|C|TT
CAAT BOX                 TATAA BOX         TRANSCRIPTION SITE

+28
GTCAGTGAGGTCCAGATACCTACAG-3'

FIG. 1

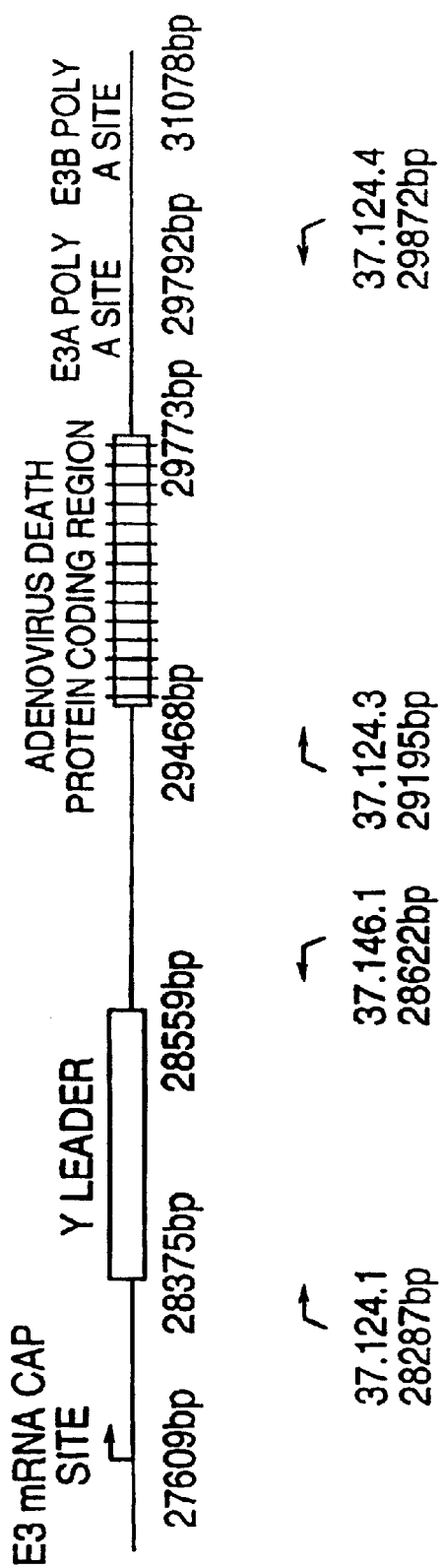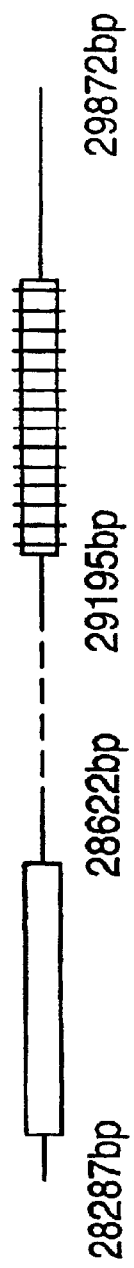
FIG. 5A
FIG. 5B

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 454 base pairs
      (B) TYPE: nucleic acid (C) STRANDEDNESS: single
        (D) TOPOLOGY: linear (xi) SEQUENCE DESCRIPTION: SEQ ID NO: 1:

| | | | | | |
|---|---|---|---|---|---|
| AAGCTTCCAC | AAGTGCATTT | AGCCTCTCCA | GTATTGCTGA | TGAATCCACA | GTTCAGGTTC | 60 |
| AATGGCGTTC | AAAACTTGAT | CAAAAATGAC | CAGACTTTAT | ATTCTTACAC | CAACATCTAT | 120 |
| CTGATTGGAG | GAATGGATAA | TAGTCATCAT | GTTTAAACAT | CTACCATTCC | AGTTAAGAAA | 180 |
| ATATGATAGC | ATCTTGTTCT | TAGTCTTTTT | CTTAATAGGG | ACATAAAGCC | CACAAATAAA | 240 |
| AATATGCCTG | AAGAATGGGA | CAGGCATTGG | GCATTGTCCA | TGCCTAGTAA | AGTACTCCAA | 300 |
| GAACCTATTT | GTATACTAGA | TGACACAATG | TCAATGTCTG | TGTACAACTG | CCAACTGGGA | 360 |
| TGCAAGACAC | TGCCCATGCC | AATCATCCTG | AAAAGCAGCT | ATAAAAAGCA | GGAAGCTACT | 420 |
| CTGCACCTTG | TCAGTGAGGT | CCAGATACCT | ACAG | | | 454 |

(2) INFORMATION FOR SEQ ID NO: 2:

(i) SEQUENCE CHARACTERISTICS:
        (A) LENGTH: 5836 base pairs
        (B) TYPE: nucleic acid
        (C) STRANDEDNESS: single
        (D) TOPOLOGY: linear (xi) SEQUENCE DESCRIPTION: SEQ ID NO: 2:

| | | | | | |
|---|---|---|---|---|---|
| AAGCTTCTAG | TTTTCTTTTC | CCGGTGACAT | CGTGGAAAGC | ACTAGCATCT | CTAAGCAATG | 60 |
| ATCTGTGACA | ATATTCACAG | TGTAATGCCA | TCCAGGGAAC | TCAACTGAGC | CTTGATGTCC | 120 |
| AGAGATTTTT | GTGTTTTTTT | CTGAGACTGA | GTCTCGCTCT | GTGCCAGGCT | GGAGTGCAGT | 180 |
| GGTGCAACCT | TGGCTCACTG | CAAGCTCCGC | CTCCTGGGTT | CACGCCATTC | TCCTGCCTCA | 240 |
| GCCTCCTGAG | TAGCTGGGAC | TACAGGCACC | CGCCACCACG | CCTGGCTAAT | TTTTTTGTAT | 300 |
| TTTTAGTAGA | GATGGGGTTT | CACTGTGTTA | GCCAGGATGG | TCTCAGTCTC | CTGACCTCGT | 360 |
| GATCTGCCCA | CCTTGGCCTC | CCAAAGTGCT | GGGATGACAG | GCGTGAGCCA | CCGCGCCTGG | 420 |
| CCGATATCCA | GAGATTTTTT | GGGGGGCTCC | ATCACACAGA | CATGTTGACT | GTCTTCATGG | 480 |
| TTGACTTTTA | GTATCCAGCC | CCTCTAGAAA | TCTAGCTGAT | ATAGTGTGGC | TCAAAACCTT | 540 |
| CAGCACAAAT | CACACCGTTA | GACTATCTGG | TGTGGCCCAA | ACCTTCAGGT | GAACAAAGGG | 600 |
| ACTCTAATCT | GGCAGGATAT | TCCAAAGCAT | TAGAGATGAC | CTCTTGCAAA | GAAAAAGAAA | 660 |
| TGGAAAAGAA | AAAGAAAGAA | AGGAAAAAAA | AAAAAAAAAA | GAGATGACCT | CTCAGGCTCT | 720 |
| GAGGGGAAAC | GCCTGAGGTC | TTTGAGCAAG | GTCAGTCCTC | TGTTGCACAG | TCTCCCTCAC | 780 |
| AGGGTCATTG | TGACGATCAA | ATGTGGTCAC | GTGTATGAGG | CACCAGCACA | TGCCTGGCTC | 840 |
| TGGGGAGTGC | CGTGTAAGTG | TATGCTTGCA | CTGCTGAATG | CTTGGGATGT | GTCAGGGATT | 900 |
| ATCTTCAGCA | CTTACAGATG | CTCATCTCAT | CCTCACAGCA | TCACTATGGG | ATGGGTATTA | 960 |
| CTGGCCTCAT | TTGATGGAGA | AAGTGGCTGT | GGCTCAGAAA | GGGGGGACCA | CTAGACCAGG | 1020 |
| GACACTCTGG | ATGCTGGGGA | CTCCAGAGAC | CATGACCACT | CACCAACTGC | AGAGAAATTA | 1080 |
| ATTGTGGCCT | GATGTCCCTG | TCCTGGAGAG | GGTGGAGGTG | GACCTTCACT | AACCTCCTAC | 1140 |
| CTTGACCCTC | TCTTTTAGGG | CTCTTTCTGA | CCTCCACCAT | GGTACTAGGA | CCCCATTGTA | 1200 |
| TTCTGTACCC | TCTTGACTCT | ATGACCCCCA | CTGCCCACTG | CATCCAGCTG | GGTCCCCTCC | 1260 |
| TATCTCTATT | CCCAGCTGGC | CAGTGCAGTC | TCAGTGCCCA | CCTGTTTGTC | AGTAACTCTG | 1320 |
| AAGGGGCTGA | CATTTTACTG | ACTTGCAAAC | AAATAAGCTA | ACTTTCCAGA | GTTTTGTGAA | 1380 |
| TGCTGGCAGA | GTCCATGAGA | CTCCTGAGTC | AGAGGCAAAG | GCTTTTACTG | CTCACAGCTT | 1440 |

```
                                       -continued

AGCAGACAGC ATGAGGTTCA TGTTCACATT AGTACACCTT GCCCCCCCCA AATCTTGTAG   1500

GGTGACCAGA GCAGTCTAGG TGGATGCTGT GCAGAAGGGG TTTGTGCCAC TGGTGAGAAA   1560

CCTGAGATTA GGAATCCTCA ATCTTATACT GGGACAACTT GCAAACCTGC TCAGCCTTTG   1620

TCTCTGATGA AGATATTATC TTCATGATCT TGGATTGAAA ACAGACCTAC TCTGGAGGAA   1680

CATATTGTAT CGATTGTCCT TGACAGTAAA CAAATCTGTT GTAAGAGACA TTATCTTTAT   1740

TATCTAGGAC AGTAAGCAAG CCTGGATCTG AGAGAGATAT CATCTTGCAA GGATGCCTGC   1800

TTTACAAACA TCCTTGAAAC AACAATCCAG AAAAAAAAAG GTGTTGCTGT CTTTGCTCAG   1860

AAGACACACA GATACGTGAC AGAACCATGG AGAATTGCCT CCCAACGCTG TTCAGCCAGA   1920

GCCTTCCACC CTTGTCTGCA GGACAGTCTC AACGTTCCAC CATTAAATAC TTCTTCTATC   1980

ACATCCTGCT TCTTTATGCC TAACCAAGGT TCTAGGTCCC GATCGACTGT GTCTGGCAGC   2040

ACTCCACTGC CAAACCCAGA ATAAGGCAGC GCTCAGGATC CCGAAGGGGC ATGGCTGGGG   2100

ATCAGAACTT CTGGGTTTGA GTGAGGAGTG GGTCCACCCT CTTGAATTTC AAAGGAGGAA   2160

GAGGCTGGAT GTGAAGGTAC TGGGGGAGGG AAAGTGTCAG TTCCGAACTC TTAGGTCAAT   2220

GAGGGAGGAG ACTGGTAAGG TCCCAGCTCC CGAGGTACTG ATGTGGGAAT GGCCTAAGAA   2280

TCTCATATCC TCAGGAAGAA GGTGCTGGAA TCCTGAGGGG TAGAGTTCTG GGTATATTTG   2340

TGGCTTAAGG CTCTTTGGCC CCTGAAGGCA GAGGCTGGAA CCATTAGGTC CAGGGTTTGG   2400

GGTGATAGTA ATGGGATCTC TTGATTCCTC AAGAGTCTGA GGATCGAGGG TTGCCCATTC   2460

TTCCATCTTG CCACCTAATC CTTACTCCAC TTGAGGGTAT CACCAGCCCT TCTAGCTCCA   2520

TGAAGGTCCC CTGGGCAAGC ACAATCTGAG CATGAAAGAT GCCCCAGAGG CCTTGGGTGT   2580

CATCCACTCA TCATCCAGCA TCACACTCTG AGGGTGTGGC CAGCACCATG ACGTCATGTT   2640

GCTGTGACTA TCCCTGCAGC GTGCCTCTCC AGCCACCTGC CAACCGTAGA GCTGCCCATC   2700

CTCCTCTGGT GGGAGTGGCC TGCATGGTGC CAGGCTGAGG CCTAGTGTCA GACAGGGAGC   2760

CTGGAATCAT AGGGATCCAG GACTCAAAAG TGCTAGAGAA TGGCCATATG TCACCATCCA   2820

TGAAATCTCA AGGGCTTCTG GGTGGAGGGC ACAGGGACCT GAACTTATGG TTTCCCAAGT   2880

CTATTGCTCT CCCAAGTGAG TCTCCCAGAT ACGAGGCACT GTGCCAGCAT CAGCCTTATC   2940

TCCACCACAT CTTGTAAAAG GACTACCCAG GGCCCTGATG AACACCATGG TGTGTACAGG   3000

AGTAGGGGGT GGAGGCACGG ACTCCTGTGA GGTCACAGCC AAGGGAGCAT CATCATGGGT   3060

GGGGAGGAGG CAATGGACAG GCTTGAGAAC GGGGATGTGG TTGTATTTGG TTTTCTTTGG   3120

TTAGATAAAG TGCTGGGTAT AGGATTGAGA GTGGAGTATG AAGACCAGTT AGGATGGAGG   3180

ATCAGATTGG AGTTGGGTTA GATAAAGTGC TGGGTATAGG ATTGAGAGTG GAGTATGAAG   3240

ACCAGTTAGG ATGGAGGATC AGATTGGAGT TGGGTTAGAG ATGGGGTAAA ATTGTGCTCC   3300

GGATGAGTTT GGGATTGACA CTGTGGAGGT GGTTTGGGAT GGCATGGCTT TGGGATGGAA   3360

ATAGATTTGT TTTGATGTTG GCTCAGACAT CCTTGGGGAT TGAACTGGGG ATGAAGCTGG   3420

GTTTGATTTT GGAGGTAGAA GACGTGGAAG TAGCTGTCAG ATTTGACAGT GGCCATGAGT   3480

TTTGTTTGAT GGGGAATCAA ACAATGGGGG AAGACATAAG GGTTGGCTTG TTAGGTTAAG   3540

TTGCGTTGGG TTGATGGGGT CGGGGCTGTG TATAATGCAG TTGGATTGGT TTGTATTAAA   3600

TTGGGTTGGG TCAGGTTTTG GTTGAGGATG AGTTGAGGAT ATGCTTGGGG ACACCGGATC   3660

CATGAGGTTC TCACTGGAGT GGAGACAAAC TTCCTTTCCA GGATGAATCC AGGGAAGCCT   3720

TAATTCACGT GTAGGGGAGG TCAGGCCACT GGCTAAGTAT ATCCTTCCAC TCCAGCTCTA   3780
```

-continued

```
AGATGGTCTT AAATTGTGAT TATCTATATC CACTTCTGTC TCCCTCACTG TGCTTGGAGT    3840

TTACCTGATC ACTCAACTAG AAACAGGGGA AGATTTTATC AAATTCTTTT TTTTTTTTTT    3900

TTTTTTTTGA GACAGAGTCT CACTCTGTTG CCCAGGCTGG AGTGCAGTGG CGCAGTCTCG    3960

GCTCACTGCA ACCTCTGCCT CCCAGGTTCA AGTGATTCTC CTGCCTCAGC CTCCTGAGTT    4020

GCTGGGATTA CAGGCATGCA GCACCATGCC CAGCTAATTT TTGTATTTTT AGTAGAGATG    4080

GGGTTTCACC ATGTTTGCC AGGCTGGCCT CGAACTCCTG ACCTGGTGAT CCACCTGCCT     4140

CAGCCTCCCA AAGTGCTGGG ATTACAGGCG TCAGCCACCG CGCCCAGCCA CTTTTGTCAA    4200

ATTCTTGAGA CACAGCTCGG GCTGGATCAA GTGAGCTACT CTGGTTTTAT TGAACAGCTG    4260

AAATAACCAA CTTTTTGGAA ATTGATGAAA TCTTACGGAG TTAACAGTGG AGGTACCAGG    4320

GCTCTTAAGA GTTCCCGATT CTCTTCTGAG ACTACAAATT GTGATTTTGC ATGCCACCTT    4380

AATCTTTTTT TTTTTTTTTT TAAATCGAGG TTTCAGTCTC ATTCTATTTC CCAGGCTGGA    4440

GTTCAATAGC GTGATCACAG CTCACTGTAG CCTTGAACTC CTGGCCTTAA GAGATTCTCC    4500

TGCTTCGGTC TCCCAATAGC TAAGACTACA GTAGTCCACC ACCATATCCA GATAATTTTT    4560

AAATTTTTTG GGGGGCCGGG CACAGTGGCT CACGCCTGTA ATCCCAACAC CATGGGAGGC    4620

TGAGATGGGT GGATCACGAG GTCAGGAGTT TGAGACCAGC CTGACCAACA TGGTGAAACT    4680

CTGTCTCTAC TAAAAAAAAA AAAAATAGAA AAATTAGCCG GGCGTGGTGG CACACGGCAC    4740

CTGTAATCCC AGCTACTGAG GAGGCTGAGG CAGGAGAATC ACTTGAACCC AGAAGGCAGA    4800

GGTTGCAATG AGCCGAGATT GCGCCACTGC ACTCCAGCCT GGGTGACAGA GTGAGACTCT    4860

GTCTCAAAAA AAAAAAATTT TTTTTTTTTT TTTGTAGAGA TGGATCTTGC TTTGTTTCTC    4920

TGGTTGGCCT TGAACTCCTG GCTTCAAGTG ATCCTCCTAC CTTGGCCTCG GAAAGTGTTG    4980

GGATTACAGG CGTGAGCCAC CATGACTGAC CTGTCGTTAA TCTTGAGGTA CATAAACCTG    5040

GCTCCTAAAG GCTAAAGGCT AAATATTTGT TGGAGAAGGG GCATTGGATT TTGCATGAGG    5100

ATGATTCTGA CCTGGGAGGG CAGGTCAGCA GGCATCTCTG TTGCACAGAT AGAGTGTACA    5160

GGTCTGGAGA ACAAGGAGTG GGGGGTTATT GGAATTCCAC ATTGTTTGCT GCACGTTGGA    5220

TTTTGAAATG CTAGGGAACT TTGGGAGACT CATATTTCTG GGCTAGAGGA TCTGTGGACC    5280

ACAAGATCTT TTTATGATGA CAGTAGCAAT GTATCTGTGG AGCTGGATTC TGGGTTGGGA    5340

GTGCAAGGAA AAGAATGTAC TAAATGCCAA GACATCTATT TCAGGAGCAT GAGGAATAAA    5400

AGTTCTAGTT TCTGGTCTCA GAGTGGTGCA GGGATCAGGG AGTCTCACAA TCTCCTGAGT    5460

GCTGGTGTCT TAGGGCACAC TGGGTCTTGG AGTGCAAAGG ATCTAGGCAC GTGAGGCTTT    5520

GTATGAAGAA TCGGGATCG TACCCACCCC CTGTTTCTGT TTCATCCTGG GCATGTCTCC     5580

TCTGCCTTTG TCCCCTAGAT GAAGTCTCCA TGAGCTACAA GGGCCTGGTG CATCCAGGGT    5640

GATCTAGTAA TTGCAGAACA GCAAGTGCTA GCTCTCCCTC CCCTTCCACA GCTCTGGGTG    5700

TGGGAGGGGG TTGTCCAGCC TCCAGCAGCA TGGGGAGGGC CTTGGTCAGC CTCTGGGTGC    5760

CAGCAGGGCA GGGGCGGAGT CCTGGGGAAT GAAGGTTTTA TAGGGCTCCT GGGGGAGGCT    5820

CCCCAGCCCC AAGCTT                                                    5836
```

(2) INFORMATION FOR SEQ ID NO: 3:

(i) SEQUENCE CHARACTERISTICS:
        (A) LENGTH: 5835 base pairs
        (B) TYPE: nucleic acid
        (C) STRANDEDNESS: single
        (D) TOPOLOGY: linear -continued (xi) SEQUENCE DESCRIPTION: SEQ ID NO: 3:

```
AAGCTTCTAG TTTTCTTTTC CCGGTGACAT CGTGGAAAGC ACTAGCATCT CTAAGCAATG      60
ATCTGTGACA ATATTCACAG TGTAATGCCA TCCAGGGAAC TCAACTGAGC CTTGATGTCC     120
AGAGATTTTT GTGTTTTTTT CTGAGACTGA GTCTCGCTCT GTGCCAGGCT GGAGTGCAGT     180
GGTGCAACCT TGGCTCACTG CAAGCTCCGC CTCCTGGGTT CACGCCATTC TCCTGCCTCA     240
GCCTCCTGAG TAGCTGGGAC TACAGGCACC CGCCACCACG CCTGGCTAAT TTTTTTGTAT     300
TTTTAGTAGA GATGGGGTTT CACTGTGTTA GCCAGGATGG TCTCAGTCTC CTGACCTCGT     360
GATCTGCCCA CCTTGGCCTC CCAAAGTGCT GGGATGACAG GCGTGAGCCA CCGCGCCTGG     420
CCGATATCCA GAGATTTTTT GGGGGGCTCC ATCACACAGA CATGTTGACT GTCTTCATGG     480
TTGACTTTTA GTATCCAGCC CCTCTAGAAA TCTAGCTGAT ATAGTGTGGC TCAAAACCTT     540
CAGCACAAAT CACACCGTTA GACTATCTGG TGTGGCCCAA ACCTTCAGGT GAACAAAGGG     600
ACTCTAATCT GGCAGGATAC TCCAAAGCAT TAGAGATGAC CTCTTGCAAA GAAAAAGAAA     660
TGGAAAAGAA AAAGAAAGAA AGGAAAAAAA AAAAAAAAAA GAGATGACCT CTCAGGCTCT     720
GAGGGGAAAC GCCTGAGGTC TTTGAGCAAG GTCAGTCCTC TGTTGCACAG TCTCCCTCAC     780
AGGGTCATTG TGACGATCAA ATGTGGTCAC GTGTATGAGG CACCAGCACA TGCCTGGCTC     840
TGGGGAGTGC CGTGTAAGTG TATGCTTGCA CTGCTGAATG GCTGGGATGT GTCAGGGATT     900
ATCTTCAGCA CTTACAGATG CTCATCTCAT CCTCACAGCA TCACTATGGG ATGGGTATTA     960
CTGGCCTCAT TGATGGAGA AAGTGGCTGT GGCTCAGAAA GGGGGGACCA CTAGACCAGG    1020
GACACTCTGG ATGCTGGGGA CTCCAGAGAC CATGACCACT CACCAACTGC AGAGAAATTA    1080
ATTGTGGCCT GATGTCCCTG TCCTGGAGAG GGTGGAGGTG GACCTTCACT AACCTCCTAC    1140
CTTGACCCTC TCTTTTAGGG CTCTTTCTGA CCTCCACCAT GGTACTAGGA CCCCATTGTA    1200
TTCTGTACCC TCTTGACTCT ATGACCCCCA CCGCCCACTG CATCCAGCTG GGTCCCCTCC    1260
TATCTCTATT CCCAGCTGGC CAGTGCAGTC TCAGTGCCCA CCTGTTTGTC AGTAACTCTG    1320
AAGGGGCTGA CATTTTACTG ACTTGCAAAC AAATAAGCTA ACTTTCCAGA GTTTTGTGAA    1380
TGCTGGCAGA GTCCATGAGA CTCCTGAGTC AGAGGCAAAG GCTTTTACTG CTCACAGCTT    1440
AGCAGACAGC ATGAGGTTCA TGTTCACATT AGTACACCTT GCCCCCCCCA AATCTTGTAG    1500
GGTGACCAGA GCAGTCTAGG TGGATGCTGT GCAGAAGGGG TTTGTGCCAC TGGTGAGAAA    1560
CCTGAGATTA GGAATCCTCA ATCTTATACT GGGACAACTT GCAAACCTGC TCAGCCTTTG    1620
TCTCTGATGA AGATATTATC TTCATGATCT TGGATTGAAA ACAGACCTAC TCTGGAGGAA    1680
CATATTGTAT CGATTGTCCT TGACAGTAAA CAAATCTGTT GTAAGAGACA TTATCTTTAT    1740
TATCTAGGAC AGTAAGCAAG CCTGGATCTG AGAGAGATAT CATCTTGCAA GGATGCCTGC    1800
TTTACAAACA TCCTTGAAAC AACAATCCAG AAAAAAAAAG GTGTTACTGT CTTTGCTCAG    1860
AAGACACACA GATACGTGAC AGAACCATGG AGAATTGCCT CCCAACGCTG TTCAGCCAGA    1920
GCCTTCCACC CTTTCTGCAG GACAGTCTCA ACGTTCCACC ATTAAATACT TCTTCTATCA    1980
CATCCCGCTT CTTTATGCCT AACCAAGGTT CTAGGTCCCG ATCGACTGTG TCTGGCAGCA    2040
CTCCACTGCC AAACCCAGAA TAAGGCAGCG CTCAGGATCC CGAAGGGCA TGGCTGGGA     2100
TCAGAACTTC TGGGTTTGAG TGAGGAGTGG GTCCACCCTC TTGAATTTCA AGGAGGAAG     2160
AGGCTGGATG TGAAGGTACT GGGGGAGGGA AAGTGTCAGT TCCGAACTCT TAGGTCAATG    2220
AGGGAGGAGA CTGGTAAGGT CCCAGCTCCC GAGGTACTGA TGTGGGAATG CCTAAGAAT    2280
CTCATATCCT CAGGAAGAAG GTGCTGGAAT CCTGAGGGGT AGAGTTCTGG GTATATTTGT    2340
```

```
GGCTTAAGGC TCTTTGGCCC CTGAAGGCAG AGGCTGGAAC CATTAGGTCC AGGGTTTGGG   2400

GTGATAGTAA TGGGATCTCT TGATTCCTCA AGAGTCTGAG GATCGAGGGT TGCCCATTCT   2460

TCCATCTTGC CACCTAATCC TTACTCCACT TGAGGGTATC ACCAGCCCTT CTAGCTCCAT   2520

GAAGGTCCCC TGGGCAAGCA CAATCTGAGC ATGAAAGATG CCCCAGAGGC CTTGGGTGTC   2580

ATCCACTCAT CATCCAGCAT CACACTCTGA GGGTGTGGCC AGCACCATGA CGTCATGTTG   2640

CTGTGACTAT CCCTGCAGCG TGCCTCTCCA GCCACCTGCC AACCGTAGAG CTGCCCATCC   2700

TCCTCTGGTG GGAGTGGCCT GCATGGTGCC AGGCTGAGGC CTAGTGTCAG ACAGGGAGCC   2760

TGGAATCATA GGGATCCAGG ACTCAAAAGT GCTAGAGAAT GGCCATATGT CACCATCCAT   2820

GAAATCTCAA GGGCTTCTGG GTGGAGGGCA CAGGGACCTG AACTTATGGT TTCCCAAGTC   2880

TATTGCTCTC CCAAGTGAGT CTCCCAGATA CGAGGCACTG TGCCAGCATC AGCCTTATCT   2940

CCACCACATC TTGTAAAAGG ACTACCCAGG GCCCTGATGA ACACCATGGT GTGTACAGGA   3000

GTAGGGGGTG GAGGCACGGA CTCCTGTGAG GTCACAGCCA AGGGAGCATC ATCATGGGTG   3060

GGGAGGAGGC AATGGACAGG CTTGAGAACG GGGATGTGGT TGTATTTGGT TTTCTTTGGT   3120

TAGATAAAGT GCTGGGTATA GGATTGAGAG TGGAGTATGA AGACCAGTTA GGATGGAGGA   3180

TCAGATTGGA GTTGGGTTAG ATAAAGTGCT GGGTATAGGA TTGAGAGTGG AGTATGAAGA   3240

CCAGTTAGGA TGGAGGATCA GATTGGAGTT GGGTTAGAGA TGGGTAAAA TTGTGCTCCG   3300

GATGAGTTTG GGATTGACAC TGTGGAGGTG GTTTGGGATG GCATGGCTTT GGGATGGAAA   3360

TAGATTTGTT TTGATGTTGG CTCAGACATC CTTGGGGATT GAACTGGGGA TGAAGCTGGG   3420

TTTGATTTTG GAGGTAGAAG ACGTGGAAGT AGCTGTCAGA TTTGACAGTG GCCATGAGTT   3480

TTGTTTGATG GGGAATCAAA CAATGGGGA AGACATAAGG GTTGGCTTGT TAGGTTAAGT   3540

TGCGTTGGGT TGATGGGGTC GGGGCTGTGT ATAATGCAGT TGGATTGGTT TGTATTAAAT   3600

TGGGTTGGGT CAGGTTTTGG TTGAGGATGA GTTGAGGATA TGCTTGGGGA CACCGGATCC   3660

ATGAGGTTCT CACTGGAGTG GAGACAAACT TCCTTTCCAG GATGAATCCA GGGAAGCCTT   3720

AATTCACGTG TAGGGGAGGT CAGGCCACTG GCTAAGTATA TCCTTCCACT CCAGCTCTAA   3780

GATGGTCTTA AATTGTGATT ATCTATATCC ACTTCTGTCT CCCTCACTGT GCTTGGAGTT   3840

TACCTGATCA CTCAACTAGA AACAGGGGAA GATTTTATCA AATTCTTTTT TTTTTTTTT   3900

TTTTTTTGAG ACAGAGTCTC ACTCTGTTGC CCAGGCTGGA GTGCAGTGGC GCAGTCTCGG   3960

CTCACTGCAA CCTCTGCCTC CCAGGTTCAA GTGATTCTCC TGCCTCAGCC TCCTGAGTTG   4020

CTGGGATTAC AGGCATGCAG CACCATGCCC AGCTAATTTT TGTATTTTTA GTAGAGATGG   4080

GGTTTCACCA ATGTTTGCCA GGCTGGCCTC GAACTCCTGA CCTGGTGATC CACCTGCCTC   4140

AGCCTCCCAA AGTGCTGGGA TTACAGGCGT CAGCCACCGC GCCCAGCCAC TTTTGTCAAA   4200

TTCTTGAGAC ACAGCTCGGG CTGGATCAAG TGAGCTACTC TGGTTTTATT GAACAGCTGA   4260

AATAACCAAC TTTTTGGAAA TTGATGAAAT CTTACGGAGT TAACAGTGGA GGTACCAGGG   4320

CTCTTAAGAG TTCCCGATTC TCTTCTGAGA CTACAAATTG TGATTTTGCA TGCCACCTTA   4380

ATCTTTTTTT TTTTTTTTTT AAATCGAGGT TTCAGTCTCA TTCTATTTCC CAGGCTGGAG   4440

TTCAATAGCG TGATCACAGC TCACTGTAGC CTTGAACTCC TGGCCTTAAG AGATTCTCCT   4500

GCTTCGGTCT CCCAATAGCT AAGACTACAG TAGTCCACCA CCATATCCAG ATAATTTTTA   4560

AATTTTTTGG GGGGCCGGGC ACAGTGGCTC ACGCCTGTAA TCCCAACACC ATGGGAGGCT   4620

GAGATGGGTG GATCACGAGG TCAGGAGTTT GAGACCAGCC TGACCAACAT GGTGAAACTC   4680
```

```
TGTCTCTACT AAAAAAAAAA AAAATAGAAA AATTAGCCGG GCGTGGTGGC ACACGGCACC    4740

TGTAATCCCA GCTACTGAGG AGGCTGAGGC AGGAGAATCA CTTGAACCCA GAAGGCAGAG    4800

GTTGCAATGA GCCGAGATTG CGCCACTGCA CTCCAGCCTG GGTGACAGAG TGAGACTCTG    4860

TCTCAAAAAA AAAAAATTTT TTTTTTTTTT TTGTAGAGAT GGATCTTGCT TTGTTTCTCT    4920

GGTTGGCCTT GAACTCCTGG CTTCAAGTGA TCCTCCTACC TTGGCCTCGG AAAGTGTTGG    4980

GATTACAGGC GTGAGCCACC ATGACTGACC TGTCGTTAAT CTTGAGGTAC ATAAACCTGG    5040

CTCCTAAAGG CTAAAGGCTA AATATTTGTT GGAGAAGGGG CATTGGATTT TGCATGAGGA    5100

TGATTCTGAC CTGGGAGGGC AGGTCAGCAG GCATCTCTGT TGCACAGATA GAGTGTACAG    5160

GTCTGGAGAA CAAGGAGTGG GGGGTTATTG GAATTCCACA TTGTTTGCTG CACGTTGGAT    5220

TTTGAAATGC TAGGGAACTT TGGGAGACTC ATATTTCTGG GCTAGAGGAT CTGTGGACCA    5280

CAAGATCTTT TTATGATGAC AGTAGCAATG TATCTGTGGA GCTGGATTCT GGGTTGGGAG    5340

TGCAAGGAAA AGAATGTACT AAATGCCAAG ACATCTATTT CAGGAGCATG AGGAATAAAA    5400

GTTCTAGTTT CTGGTCTCAG AGTGGTGCAT GGATCAGGGA GTCTCACAAT CTCCTGAGTG    5460

CTGGTGTCTT AGGGCACACT GGGTCTTGGA GTGCAAAGGA TCTAGGCACG TGAGGCTTTG    5520

TATGAAGAAT CGGGGATCGT ACCCACCCCC TGTTTCTGTT TCATCCTGGG CATGTCTCCT    5580

CTGCCTTTGT CCCCTAGATG AAGTCTCCAT GAGCTACAAG GGCCTGGTGC ATCCAGGGTG    5640

ATCTAGTAAT TGCAGAACAG CAAGTGCTAG CTCTCCCTCC CCTTCCACAG CTCTGGGTGT    5700

GGGAGGGGGT TGTCCAGCCT CCAGCAGCAT GGGGAGGGCC TTGGTCAGCC TCTGGGTGCC    5760

AGCAGGGCAG GGGCGGAGTC CTGGGGAATG AAGGTTTTAT AGGGCTCCTG GGGGAGGCTC    5820

CCCAGCCCCA AGCTT                                                   5835

(2) INFORMATION FOR SEQ ID NO: 4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 4:

GATCACCGGT AAGCTTCCAC AAGTGCATTT AGCC                                34

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 5:

GATCACCGGT CTGTAGGTAT CTGGACCTCA CTG                                 33

(2) INFORMATION FOR SEQ ID NO: 6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 6:

GATCCGGCCG AAGCTTCCAC AAGTGCATTT AGCC                                34
```

(2) INFORMATION FOR SEQ ID NO: 7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 7:

GATCCGGCCG CTGTAGGTAT CTGGACCTCA CTG               33

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 8:

TCGTCTTCAA GAATTCTCA                             19

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 9:

TTTCAGTCAC CGGTGTCGGA                            20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 10:

GCATTCTCTA GACACAGGTG                            20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 11:

TCCGACACCG GTGACTGAAA                            20

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 12:

GCCCACGGCC GCATTATATA C                           21

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 13:

GTATATAATG CGGCCGTGGG C                              21

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 14:

CCAGAAAATC CAGCAGGTAC C                              21

(2) INFORMATION FOR SEQ ID NO: 15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 15:

GCCTTAATTA AAAGCAAACC TCACCTCCG                        29

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 16:

GTGGAACAAA AGGTGATTAA AAAATCCCAG                     30

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 17:

CACCTTTTGT TCCACCGCTC TGCTTATTAC                     30

(2) INFORMATION FOR SEQ ID NO: 18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 18:

GGCTTAATTA ACTGTGAAAG GTGGGAGC                       28

(2) INFORMATION FOR SEQ ID NO: 19:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (xi) SEQUENCE DESCRIPTION: SEQ ID NO: 19:

GCAGCTCACT TAAGTTCATG TCG                                              23

(2) INFORMATION FOR SEQ ID NO: 20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 20:

TCAGCCTAGG AAATATGACT ACGTCCG                                          27

(2) INFORMATION FOR SEQ ID NO: 21:

(i) SEQUENCE CHARACTERISTICS:
        (A) LENGTH: 307 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 2...304
        (D) OTHER INFORMATION:

(xi) SEQUENCE DESCRIPTION: SEQ ID NO: 21:

```
G ATG ACC GGC TCA ACC ATC GCG CCC ACA ACG GAC TAT CGC AAC ACC ACT      49
  Met Thr Gly Ser Thr Ile Ala Pro Thr Thr Asp Tyr Arg Asn Thr Thr
  1               5                   10                  15

GCT ACC GGA CTA ACA TCT GCC CTA AAT TTA CCC CAA GTT CAT GCC TTT        97
Ala Thr Gly Leu Thr Ser Ala Leu Asn Leu Pro Gln Val His Ala Phe
            20                  25                  30

GTC AAT GAC TGG GCG AGC TTG GAC ATG TGG TGG TTT TCC ATA GCG CTT        145
Val Asn Asp Trp Ala Ser Leu Asp Met Trp Trp Phe Ser Ile Ala Leu
        35                  40                  45

ATG TTT GTT TGC CTT ATT ATT ATG TGG CTT ATT TGT TGC CTA AAG CGC        193
Met Phe Val Cys Leu Ile Ile Met Trp Leu Ile Cys Cys Leu Lys Arg
    50                  55                  60

AGA CGC GCC AGA CCC CCC ATC TAT AGG CCT ATC ATT GTG CTC AAC CCA        241
Arg Arg Ala Arg Pro Pro Ile Tyr Arg Pro Ile Ile Val Leu Asn Pro
65                  70                  75                  80

CAC AAT GAA AAA ATT CAT AGA TTG GAC GGT CTG AAA CCA TGT TCT CTT        289
His Asn Glu Lys Ile His Arg Leu Asp Gly Leu Lys Pro Cys Ser Leu
                85                  90                  95

CTT TTA CAG TAT GAT TAA                                                307
Leu Leu Gln Tyr Asp
            100
```

(2) INFORMATION FOR SEQ ID NO: 22:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein -continued

```
    (v) FRAGMENT TYPE: internal (xi) SEQUENCE DESCRIPTION: SEQ ID NO: 22:

Met Thr Gly Ser Thr Ile Ala Pro Thr Thr Asp Tyr Arg Asn Thr Thr
1               5                   10                  15

Ala Thr Gly Leu Thr Ser Ala Leu Asn Leu Pro Gln Val His Ala Phe
            20                  25                  30

Val Asn Asp Trp Ala Ser Leu Asp Met Trp Trp Phe Ser Ile Ala Leu
        35                  40                  45

Met Phe Val Cys Leu Ile Ile Met Trp Leu Ile Cys Cys Leu Lys Arg
    50                  55                  60

Arg Arg Ala Arg Pro Pro Ile Tyr Arg Pro Ile Ile Val Leu Asn Pro
65              70                  75                  80

His Asn Glu Lys Ile His Arg Leu Asp Gly Leu Lys Pro Cys Ser Leu
            85                  90                  95

Leu Leu Gln Tyr Asp
            100
```

ADENOVIRUS VECTORS SPECIFIC FOR CELLS EXPRESSING ANDROGEN RECEPTOR AND METHODS OF USE THEREOF

CROSS-REFERENCE TO RELATED APPLICATION

This application is a continuation application of U.S. Ser. No. 09/033,333 filed Mar. 2, 1998, which claims benefit of U.S. Provisional Patent Application Ser. No. 60/039,762, filed on Mar. 3, 1997, both of which applications are hereby incorporated by reference in their entirety.

STATEMENT OF RIGHTS TO INVENTIONS MADE UNDER FEDERALLY SPONSORED RESEARCH (Not applicable)

TECHNICAL FIELD

This invention relates to cell transfection using adenoviral vectors, especially replication-competent adenoviruses, and methods of their use. More Specifically, it relates to cell-specific replication of adenovirus vectors in cells expressing the androgen receptor, particularly, prostate carcinoma cells, through use of a probasin transcriptional regulatory element.

BACKGROUND OF THE INVENTION

There are three significant diseases of the prostate: benign prostate hyperplasia (BPH), prostate cancer, and prostatitis. The cost of treating these three diseases is immense. The annual treatment of prostate diseases in the U.S. required 4.4 million physician visits, 836,000 hospitalizations, and cost over $3 billion in 1985. Approximately one out of every four males above the age of 55 suffers from a prostate disease of some form or another. Prostate cancer is the fastest growing cause of cancer in men, with approximately 244,000 new cases diagnosed and about 44,000 deaths reported for 1995 in the United States. Due to the aging U.S. population, the incidence of BPH and prostate cancer is likely to increase.

BPH causes urinary obstruction resulting in urinary incontinence. It occurs in almost 80% of men by the age of 80. Unregulated dihydrotestosterone is believed to cause hyperplastic prostate growth. Pharmacotherapy for the treatment of BPH is currently aimed at relaxing prostate smooth muscle (alpha blockade) and decreasing prostate volume (androgen suppression). Phase III clinical trials are underway to evaluate selective alpha, blockers, antiandrogens, and 5-alpha reductase inhibitors for the treatment of BPH. The most promising of these is finasteride, which has shown an ability to cause regression of the hyperplastic prostate gland in a majority of patients. Mocellini et. al. (1993) *Prostate* 22:291.

BPH is treated surgically with a transurethral resection of the prostate (TURP). This procedure is very common: 500,000 TURPs are performed in the U.S. each year and 25% of men will require surgery at some time in their lives to alleviate urinary obstruction. This makes BPH the second most common cause of surgery in males. The TURP procedure requires several days of hospitalization as well as the surgery itself. The average medical reimbursement cost of a TURP in 1987 dollars was $8,000; in 1993 dollars this is $14,000. Unfortunately, a side-effect of the TURP is the elimination of the ejaculatory ducts as well as the nerve bundles of the penis, resulting in impotence in 90% of patients. A TURP is prefaced by an outpatient biopsy procedure to determine if the enlargement of the prostate is benign or cancerous, which also adds to the cost. Hypertrophy may also be treated by transurethral insertion of a tubular stent or expandable dilation catheter to maintain the patency of the urethral lumen. U.S. Pat. No. 4,893,623, issued Jan. 16, 1990, to Rosenbluth et al.; and U.S. Pat. No. 5,527,336, issued Jun. 18, 1996, to Rosenbluth et al.

An alternative therapy for prostate diseases involves radiation therapy. A catheter has been developed which squeezes prostate tissue during microwave irradiation; this increases the therapeutic temperature to which the prostate tissue more distal to the microwave antennae can be heated without excessively heating nearby non-prostate tissue. U.S. Pat. No. 5,007,437, issued Apr. 16, 1991, to Sterzer et al. A combination of a radiating energy device integrated with a urinary drainage Foley type catheter has also been developed. U.S. Pat. No. 5,344,435, issued Sep. 6, 1994, to Turner et al.

Prostate cancer is now the most frequently diagnosed cancer in men. Prostate cancer is latent; many men carry prostate cancer cells without overt signs of disease. Autopsies of individuals dying of other causes show prostate cancer cells in 30% of men at age 50; by age 80, the prevalence is 60%. Further, prostate cancer can take up to 10 years to kill the patient after initial diagnosis. Prostate cancer is newly diagnosed in slightly over 100,000 men in the U.S. each year, of which over 40,000 will die of the disease. There is also high morbidity. Cancer metastasis to bone (late stage) is common and often associated with uncontrollable pain. Metastasis also occurs to lymph nodes (early stage).

The disease progresses from a well-defined mass within the prostate, to a breakdown and invasion of the lateral margins of the prostate, to metastasis to regional lymph nodes, to metastasis to the bone marrow. The aggressiveness of prostate tumors varies widely. Some tumors are relatively aggressive, doubling every six months, whereas other are extremely slow-growing, doubling once every five years. As a consequence of the slow growth rate, few cancer cells are actively dividing at any one time. As a result, prostate cancer is generally resistant to radiation and chemotherapy, although both therapeutic modalities are widely used. Surgery is the mainstay of treatment but it too is largely ineffective and also removes the ejaculatory ducts, resulting in impotence.

Unfortunately, in 80% of cases, diagnosis of prostate cancer is established when the disease has already metastasized to the bones. Of special interest is the observation that prostate cancers frequently grow more rapidly in sites of metastasis than within the prostate itself, the site of the primary cancer.

At this stage there is no effective cytotoxic chemotherapy for prostate cancer. Current therapeutic techniques include the use of chemical forms of medical castration by shutting down androgen production in the testes, or directly blocking androgen production in the prostate. For the treatment of prostate cancer oral estrogens and luteinizing releasing hormone analogs are used as well as surgical removal of glands that produce androgens (orchiectomy or adrenalectomy). However, estrogens are no longer recommended because of serious, even lethal, cardiovascular complications. Luteinizing hormone releasing hormone (LHRH) analogs are used instead. However, hormonal therapy invariably fails with time with the development of hormone-resistant tumor cells. It is not known whether these cells develop as a mutation of the original hormone sensitive cells, or a separate class of cells. Furthermore, since 20% of patients fail to respond to hormonal therapy, it is believed that hormone-resistant cells are present at the onset of therapy.

Estramustine, a steroidal nitrogen mustard derivative, was originally thought to be suitable for targeted drug delivery through conjugation of estrogen to toxic nitrogen mustard. Clinical trials, however, have been disappointing when survival is used as an endpoint. Finasteride, a 4-aza steroid (Proscar® from Merck & Co.), inhibits the enzyme responsible for the intracellular conversion of testosterone to dihydrotestosterone, the most potent androgen in the prostate. Casodex® is thought to inhibit cellular uptake of testosterone by blocking androgen receptors in the nucleus. However, almost all advanced cancer prostate cells fail to respond to androgen deprivation. Indolocarbazole derivatives such as K-252a have also recently been developed to treat prostate diseases. U.S. Pat. No. 5,516,771, issued May 14, 1996, to Dionne.

None of these techniques for treating prostate diseases has been universally successful. Following localized therapy, up to 40% of patients with advanced disease, and a large proportion of all patients, eventually develop metastatic disease. Treatment for advanced disease initially involving hormonal manipulations and palliative radiotherapy have demonstrated symptomatic relief, but not long-term disease-free survival. The use of cytotoxic agents in the management of hormone-resistant advanced prostate cancer remains poorly defined. A few single agents have become "standard therapy", although demonstration of their efficacy, by contemporary standards, is lacking. Combination chemotherapy is frequently employed, although its contribution to overall patient management is largely unsubstantiated, especially when critical assessment of efficacy parameters are used. Newer approaches using chemohormonal therapy and hormonal priming therapies have failed. High-dose chemotherapy with transplant regimens are not well-tolerated in an elderly population, to which most victims of prostate cancer belong. A growth factor inhibitor, suramin, has shown promising initial results. However, no therapy to date has been demonstrated to improve overall survival in patients with advanced hormone refractory prostate cancer. U.S. Pat. No. 5,569,667, issued Oct. 29, 1996, to Grove et al.

A major, indeed the overwhelming, obstacle to cancer therapy is the problem of selectivity; that is, the ability to inhibit the multiplication of tumor cells, while leaving unaffected the function of normal cells. Thus, the therapeutic ratio, or ratio of tumor cell killing to normal cell killing of traditional tumor chemotherapy, is only 1.5:1. Thus, more effective treatment methods and pharmaceutical compositions for therapy and prophylaxis of prostatic hyperplasia and neoplasia are needed.

Of particular interest is development of more specific, targeted forms of therapy for prostate diseases. In contrast to conventional cancer therapies, which result in relatively non-specific and often serious toxicity or impotence, more specific treatment modalities attempt to inhibit or kill malignant cells selectively while leaving healthy cells intact.

One possible treatment approach for prostate diseases is gene therapy, whereby a gene of interest is introduced into the malignant cell. Boulikas (1997) *Anticancer Res.* 17:1471–1505. The gene of interest may encode a protein which converts into a toxic substance upon treatment with another compound, or an enzyme that converts a prodrug to an active drug. For example, introduction of the herpes simplex gene encoding thymidine kinase (HSV-tk) renders cells conditionally sensitive to ganciclovir (GCV). Zjilstra et al. (1989) *Nature* 342: 435; Mansour et al. (1988) *Nature* 336: 348; Johnson et al. (1989) *Science* 245: 1234; Adair et al. (1989) *Proc. Natl. Acad. Sci. USA* 86: 4574; and Capecchi (1989) *Science* 244: 1288. Alternatively, the gene of interest may encode a compound that is directly toxic, such as diphtheria toxin (DT). For these treatments to be rendered specific to prostate cells, the gene of interest can be under control of a transcriptional regulatory element that is specifically (i.e. preferentially) increases transcription of an operably linked polynucleotide in the prostate cells. Cell- or tissue-specific expression can be achieved by using cell-specific enhancers and/or promoters. See generally, Huber et al. (1995) *Adv. Drug Delivery Rev.* 17:279–292.

A variety of viral and non-viral (e.g., liposomes) vehicles, or vectors, have been developed to transfer these genes. Of the viruses, retroviruses, herpes virus, adeno-associated virus, Sindbis virus, poxvirus and adenoviruses have been proposed for use in gene transfer, with retrovirus vectors or adenovirus vectors being the focus of much current research. Verma and Somia (1997) *Nature* 389:239–242. Adenoviruses are among the most easily produced and purified, whereas retroviruses are unstable, difficult to produce and to purify, and may integrate into the host genome, raising the possibility of dangerous mutations. Moreover, adenovirus has the advantage of effecting high efficiency of transduction and does not require cell proliferation for efficient cell transduction. For general background references regarding adenovirus and development of adenoviral vector systems, see Graham et al. (1973) *Virology* 52:456–467; Takiff et al. (1981) *Lancet* 11:832–834; Berkner et al. (1983) *Nucleic Acid Research* 11: 6003–6020; Graham (1984) *EMBO J* 3:2917–2922; Bett et al. (1993) *J. Virology* 67:5911–5921; and Bett et al. (1994) *Proc. Natl. Acad. Sci. USA* 91:8802–8806.

When used as gene transfer vehicles, adenovirus vectors are often designed to be replication-defective and are thus deliberately engineered to fail to replicate in the target cells of interest. In these vehicles, the early adenovirus gene products E1A and/or E1B are deleted and provided in trans by the packaging cell line 293. Graham et al. (1987) *J. Gen. Virol* 36:59–72; Graham (1977) *J. Genetic Virology* 68:937–940. The gene to be transduced is commonly inserted into adenovirus in the deleted E1A and/or E1B region of the virus genome. Bett et al. (1994). Replication-defective adenovirus vectors as vehicles for efficient transduction of genes have been described by, inter alia, Stratford-Perricaudet (1990) *Human Gene Therapy* 1:241–256; Rosenfeld (1991) *Science* 252:431–434; Wang et al. (1991) *Adv. Exp. Med. Biol.* 309:61–66; Jaffe et al. (1992) *Nat. Gent.* 1:372–378; Quantin et al. (1992) Proc. Natl. Acad. Sci. USA 89:2581–2584; Rosenfeld et al. (1992) *Cell* 68:143–155; Stratford-Perricaudet et al. (1992) *J. Clin. Invest.* 90:626–630; Le Gal Le Salle et al. (1993) *Science* 259:988–990; Mastrangeli et al. (1993) *J. Clin. Invest.* 91:225–234; Ragot et al. (1993) *Nature* 361:647–650; Hayaski et al. (1994) *J. Biol. Chem.* 269:23872–23875; and Bett et al. (1994).

The virtually exclusive focus in the development of adenoviral vectors for gene therapy is use of adenovirus merely as a vehicle for introducing the gene of interest, not as an effector in itself. Replication of adenovirus has been viewed as an undesirable result, largely due to the host immune response. In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity. Thus, the ability to repeatedly administer cytokines, tumor suppressor genes, ribozymes, suicide genes, or genes which convert a prodrug to an active drug has been limited by the immunogenicity of both the gene transfer vehicle and the viral gene products of the transfer vehicle as well as the transient nature of gene expression. There is a need for vector constructs that are capable of eliminating essentially all cancerous cells in a minimum number of administrations before specific immunological response against the vector prevents further treatment.

A completely separate and unrelated area of research pertains to the description of tissue-specific transcriptional regulatory proteins.

Rat Probasin (PB) Gene

The rat probasin (PB) gene encodes a nuclear and secreted protein, probasin, that is only expressed in the dorsolateral prostate. Dodd et al. (1983) *J. Biol. Chem.* 258:10731–10737; Matusik et al. (1986) *Biochem. Cell. Biol.* 64: 601–607; and Sweetland et al. (1988) *Mol. Cell. Biochem.* 84: 3–15. The dorsolateral lobes of the murine prostate are considered the most homologous to the peripheral zone of the human prostate, where approximately 68% of human prostate cancers are thought to originate. Immunohistochemistry with polyclonal and monoclonal antibodies has shown dual cellular localization of PB within the cytoplasm and nucleus of epithelial cells of the prostate. The expression of this gene is mediated by both zinc and testosterone (T), or a derivative thereof, via the androgen receptor (AR). T, the dominant testicular androgen, diffuses passively into the cell and either binds directly to the AR, or undergoes enzymatic reduction to 5α-dihydrotestosterone (DHT), or aromatization to estrogens. Once T or DHT binds to the AR, the protein undergoes conformational changes, chaperone proteins such as heat shock proteins dissociate from the receptor, and the activated receptor can then bind DNA. Johnson et al. (1988) in *Steroid Receptors and Disease* (Sheridan, ed.), pp. 207–228, Dekker, New York; and Chan et al. (1989) in *Pediatric Endocrinology* (Collu et al., eds.), pp. 81–124, Raven Press, New York.

The androgen-activated AR binds to specific DNA enhancer sequences called androgen-responsive elements (AREs or ARE sites). Once anchored to an ARE, the AR is able to regulate transcriptional activity in either a positive or negative fashion. Lindzey et al. (1994) *Vitamins and Hormones* 49: 383–432. The 5' TRE (transcriptional response element) region of PB gene contains two ARE sites required for androgen regulation. Rennie et al. (1993) *Mol. Endocrinol.* 7:23–36; International Application PCT/CA93/00319, published as WO 94/03594, Feb. 17, 1994, to Matusik.

The AR belongs to a nuclear receptor superfamily whose members are believed to function primarily as transcription factors that regulate gene activity through binding to specific DNA sequences, hormone-responsive elements. Carson-Jurica et al. (1990) *Endocr. Rev.* 11: 201–220. This family includes the other steroid hormone receptors as well as the thyroid hormone, the retinoic acid and the vitamin $D_3$ receptors. The progesterone and glucocorticoid receptor are structurally most closely related to the AR. Tilley et al. (1989) *Proc. Natl. Acad. Sci. USA* 86: 327–331; Zhou et al. (1994) *Recent Prog. Horm. Res.* 49: 249–274; and Lindzey et al. (1994) *Vit. Horm.* 49: 383–432.

Recently, the cDNAs encoding the human and rat AR have been cloned. Chang et al. (1988) *Proc. Natl. Acad Sci. USA* 85: 7211–7215; Lubahn et al. (1988) *Mol. Endocrinol.* 2:1265–1275; and Trapman et al. (1988) *Biochem. Biophys. Res. Commun.* 153: 241–248. The rat and human AR mRNAs show a high degree of sequence similarity in the coding regions and the 5' UTRs.

The AR gene itself is a target of androgenic regulation. This modulation may constitute an important level of control modulating physiological effects of testosterone. Androgen promotes up- and down-regulation of AR mRNA in a tissue- and possible stage-specific fashion. Nastiuk et al. (1994) *Endocrin.* 134: 640–649; Shan et al. (1995) *Endocrin.* 136: 3856–3862; and Prins et al. (1995) *Biol. Reprod.* 53: 609–619. In the testis, AR protein is expressed in Sertoli cells, Leydig cells and peritubular cells, but not in the developing germ cells. Grootegoed et al. (1977) *Mol. Cell. Endocrinol.* 9: 159–157; and Buzek et al. (1988) *Biol. Reprod.* 39: 39–49. Hormones such as follicle-stimulating hormone (FSH) and testosterone affect the production of AR. Verhoeven et al. (1988) *Endocrinology* 122: 1541–1550; and Blok et al. (1989) *Mol. Cell. Endocrinol.* 63: 267–271; Quarmby et al. (1990) *Mol. Endocrinol.* 4:22–28.

Up- and down-regulation of AR mRNA can be reproduced in different cell lines transfected with an AR cDNA. Burnstein et al. (1995); *Mol. Cell. Endocrinol.* 115:177–186 and Dai et al. (1996) *Steroids* 61:531–539. In both COS-1 and LNCaP cells expressing an AR cDNA, androgen promotes down-regulation of AR mRNA. Burnstein et al. (1995). The prostate cancer cells lines PC3 and DU145 do not express an endogenous AR, but when these cells are transfected with AR cDNA, the gene demonstrates androgenic up-regulation. Dai et al. (1996). Both up- and down-regulation of AR mRNA in cells expressing the AR cDNA are due to sequences within the AR cDNA. The heterologous cytomegalovirus (CMV) promoter that drives the expression of the AR cDNA is not itself responsible for androgenic regulation of AR cDNA expression. Burnstein et al. (1995); and Dai et al. (1996). Therefore, androgen-mediated differential regulation of AR cDNA expression is conferred by the AR cDNA in a cell line-specific manner. Burnstein et al. (1995); Dai et al. (1996).

The molecular mechanism of AR mRNA autoregulation is complex, with both transcriptional and post-transcriptional mechanisms implicated in this process. Prins et al. (1995) *Biol. Reprod.* 53: 609–619; Wolf et al. (1993) *Mol. Endocrin.* 7: 924–936; and Blok et al. (1992) *Mol. Cell. Endocrin.* 88: 153–164. The 5' region of the AR gene does not appear to contain AREs. Blok et al. (1992) *Mol. Cell. Endocrin.* 88: 153–164. The mechanism of androgen-mediated up-regulation of AR mRNA in PC3 cells (prostate cancer cell line) expressing a transfected human AR (hAR) cDNA has been studied. An androgen-responsive region within the AR coding sequence is bound by AR and contains two distinct AREs that act synergistically to mediate AR mRNA up-regulation. Dai et al. (1996) *Mol. Endocrin.* 10:1582–1594.

Prostate diseases are generally recalcitrant to treatment by standard therapies. Thus, it is critical to develop new therapeutic approaches for this disease. The present invention addresses this need by providing adenoviral vectors specific for replication in AR-producing cells.

All publications cited herein are hereby incorporated by reference in their entirety.

SUMMARY OF THE INVENTION

In one embodiment, the invention provides an adenovirus vector comprising an adenovirus gene under transcriptional control of a probasin transcriptional response element (PB-TRE). The PB-TRE is capable of mediating gene expression specific to cells which allow a PB-TRE to function, such as cells expressing the androgen receptor, e.g. prostate cells. The PB-TRE can comprise a promoter and/or enhancer from a probasin gene, provided that the PB-TRE is capable of mediating gene expression specific to cells expressing the androgen receptor. In one embodiment, a PB-TRE comprises a promoter from a probasin gene. In one embodiment, a PB-TRE comprises an enhancer from a probasin gene. In one embodiment, a PB-TRE comprises a promoter from a probasin gene and an enhancer from a probasin gene. In one embodiment, the PB-TRE is transcriptionally active in cells which allow a PB-TRE to function. such as cells expressing the androgen receptor (AR).

In certain embodiments, a PB-TRE comprises the nucleotide sequence of SEQ ID NO:1. In certain embodiments, a PB-TRE comprises a portion of SEQ ID NO:1 capable of mediating cell-specific transcription in AR-producing cells such as prostate cells. In another embodiment, a PB-TRE comprises the sequence from about −286 to about +28 relative to the transcriptional start site of a probasin gene (nucleotides about 141 to about 454 of SEQ ID NO:1). In another embodiment, a PB-TRE comprises the sequence from about −426 to about +28 relative to the transcriptional start site of a probasin gene (nucleotide about 1 to about 454 of SEQ ID NO:1). In another embodiment, a PB-TRE comprises the sequence to about −236 to about −223 and/or the sequence to about −140 to about −117 (nucleotides about 191 to about 204 and/or about 286 to about 310, respectively, of SEQ ID NO:1), relative to the transcriptional start site of a probasin gene, combined with a probasin or non-probasin promoter. In another embodiment, a PB-TRE comprises one or two ARE sites (androgen-responsive elements) combined with a probasin or non-probasin promoter. In each embodiment, a PB-TRE is defined as a transcriptional response element or transcriptional regulatory element capable of effecting transcription in a cell, such as a prostate cell, which allows a PB-TRE to function, such as a cell expressing androgen receptor.

In certain embodiments, the adenovirus comprises a PB-TRE, which in turn comprises at least one androgen response element (ARE). In some embodiments, the ARE is ARE-1 or ARE-2 from either the probasin gene or the AR gene. In other embodiments, the adenovirus vector comprises a PB-TRE, which in turn comprises an ARE, such as ARE-2. In other embodiments, the adenovirus vector comprises a probasin transcriptional response element, which in turn comprises both ARE-1 and ARE-2.

In some embodiments, the PB-TRE is rat in origin. In some embodiments, the rat PB-TRE is capable of mediating prostate-specific gene expression in humans.

In some embodiments, the adenovirus gene under control of a PB-TRE contributes to cytotoxicity (directly or indirectly), such as a gene essential for viral replication. In one embodiment, the adenovirus gene is an early gene. In another embodiment, the early gene is E1A. In another embodiment, the early gene is E1B. In yet another embodiment, both E1A and E1B are under transcriptional control of a PB-TRE. In other embodiments, the adenovirus gene essential for replication is a late gene. In various embodiments, the additional late gene is L1, L2, L3, L4, or L5. In another embodiment, the adenovirus gene under control of a PB-TRE is the adenovirus death protein gene (ADP).

In another embodiment, the adenovirus comprising an adenovirus gene under transcriptional control of a PB-TRE further comprises at least one additional adenovirus gene under transcriptional control of at least one additional prostate-specific transcriptional regulatory element. In one embodiment, a composition comprises this adenovirus. In one embodiment, this composition further comprises a pharmaceutically acceptable excipient. In one embodiment, the at least one additional prostate-specific transcriptional regulatory element is a second PB-TRE. In one embodiment, the at least one additional PB-TRE can have a sequence different from that of the first PB-TRE. In one embodiment, the at least one additional prostate-specific transcriptional regulatory element comprises a prostate-specific antigen (PSA) transcriptional regulatory element.

In other embodiments, the adenovirus vector can further comprise a heterologous gene or transgene, wherein said transgene is under transcriptional control of a PB-TRE. In one embodiment, the heterologous gene is a reporter gene. In one embodiment, the heterologous gene is conditionally required for cell survival. In some embodiments, the transgene is a cytotoxic gene.

In another embodiment, a method of treating prostate cancer in an individual is provided, the method comprising the step of administering to the individual an effective amount of an adenovirus vector in which an adenovirus gene is under transcriptional control of a PB-TRE. In one embodiment, the adenovirus gene is essential for viral replication. In one embodiment, the adenovirus gene is an early gene. In one embodiment, the adenovirus gene is E1A. In one embodiment, the adenovirus gene is E1B. In one embodiment, the adenovirus gene is ADP. In one embodiment, the PB-TRE comprises an enhancer from a probasin gene. In one embodiment, the PB-TRE comprises a promoter from a probasin gene. In one embodiment, the PB-TRE comprises a promoter from a probasin gene and an enhancer from a probasin gene. In one embodiment, the adenovirus further comprises an additional adenovirus gene under transcriptional control of at least one additional prostate-specific transcriptional regulatory element. In one embodiment, the second prostate-specific transcriptional regulatory element comprises a prostate-specific antigen (PSA) transcriptional regulatory element. In one embodiment, the additional adenovirus gene is essential for viral replication. In one embodiment, the additional adenovirus gene is an early gene. In one embodiment, the additional adenovirus gene is E1A. In one embodiment, the additional adenovirus early gene is E1B. In one embodiment, the additional adenovirus gene is a late gene. In various embodiments, the late gene can be L1, L2, L3, L4, or L5. In one embodiment, the additional adenovirus gene is ADP.

In another aspect, the invention provides a host cell transformed with any adenovirus vector(s) described herein.

In another aspect, the invention provides a composition comprising an adenovirus comprising an adenovirus gene under transcriptional control of a PB-TRE. In one embodiment, the composition further comprises a pharmaceutically, acceptable excipient.

In another aspect, the invention provides kits which contain an adenoviral. vector(s) described herein.

Another embodiment of the invention is an adenovirus which replicates preferentially in mammalian cells expressing AR.

In another aspect, a method is provided for propagating an adenovirus specific for cells which allow a PB-TRE to function; such as cells expressing androgen receptor, said method comprising combining any adenovirus vector(s) described herein with cells which allow a PB-TRE to function, such as cells expressing AR, whereby said adenovirus is propagated.

In another aspect, a method for modifying the genotype of a target cell is provided, the method comprising contacting a cell which allows a PB-TRE to function, such as a cell expressing androgen receptor, with any adenovirus described herein, wherein the adenovirus enters the cell.

In another aspect, methods are provided for detecting cells expressing probasin in a biological sample, comprising contacting cells of a biological sample with an adenovirus vector(s) described herein, and detecting replication of the adenovirus vector, if any.

In one embodiment, a method is provided for detecting cells which allow a PB-TRE to function, such as cells expressing androgen receptor in a biological sample, the method comprising the steps of: contacting a biological sample with an adenovirus vector comprising a gene under transcriptional control of a PB-TRE, under conditions suitable for PB-TRE-mediated gene expression in cells which allow a PB-TRE to function, such as cells expressing androgen receptor; and determining if PB-TRE mediates gene expression in the biological sample, where PB-TRE-mediated gene expression is indicative of the presence of cells which allow a PB-TRE to function, such as cells expressing the androgen receptor. In one embodiment, the gene is a heterologous (non-adenovirus gene). In one embodiment, the heterologous gene is a reporter gene, and production of the product of the reporter gene is detected.

In another embodiment, a method is provided for conferring selective toxicity on a target cell, said method comprising contacting a cell which allows a PB-TRE to function, such as a cell expressing androgen receptor, with any adenovirus disclosed herein, wherein the adenovirus enters the cell.

In one embodiment, an adenovirus is provided which comprises a heterologous gene under transcriptional control of a PB-TRE. In one embodiment the heterologous gene is a reporter gene. In one embodiment, the heterologous gene is conditionally required for cell survival. In one embodiment, a method is provided for detecting cells which allow a PB-TRE to function, such as cells expressing androgen receptor in a sample comprising the steps of: contacting a biological sample with an adenovirus vector comprising a gene under transcriptional control of a PB-TRE, under conditions suitable for PB-TRE-mediated gene expression in cells which allow a PB-TRE to function, such as cells expressing androgen receptor; and determining if PB-TRE mediates gene expression in the biological sample, where PB-TRE-mediated gene expression is indicative of the presence of cells expressing the androgen receptor.

BRIEF DESCRIPTION OF THE DRAWINGS

FIG. 1 depicts the sequence of the 5-flanking region of the rat probasin (PB) gene, including the PB-TRE region (SEQ ID NO:1).

FIGS. 5A and B are schematic depictions an adenovirus death protein (ADP) cassette for insertion into Ad. Arrows underneath FIG. 5A indicate positions of primers. FIG. 5B depicts the annealed fragment containing the Y leader sequence and the ADP coding sequence.

MODES FOR CARRYING OUT THE INVENTION

Figure 2A:
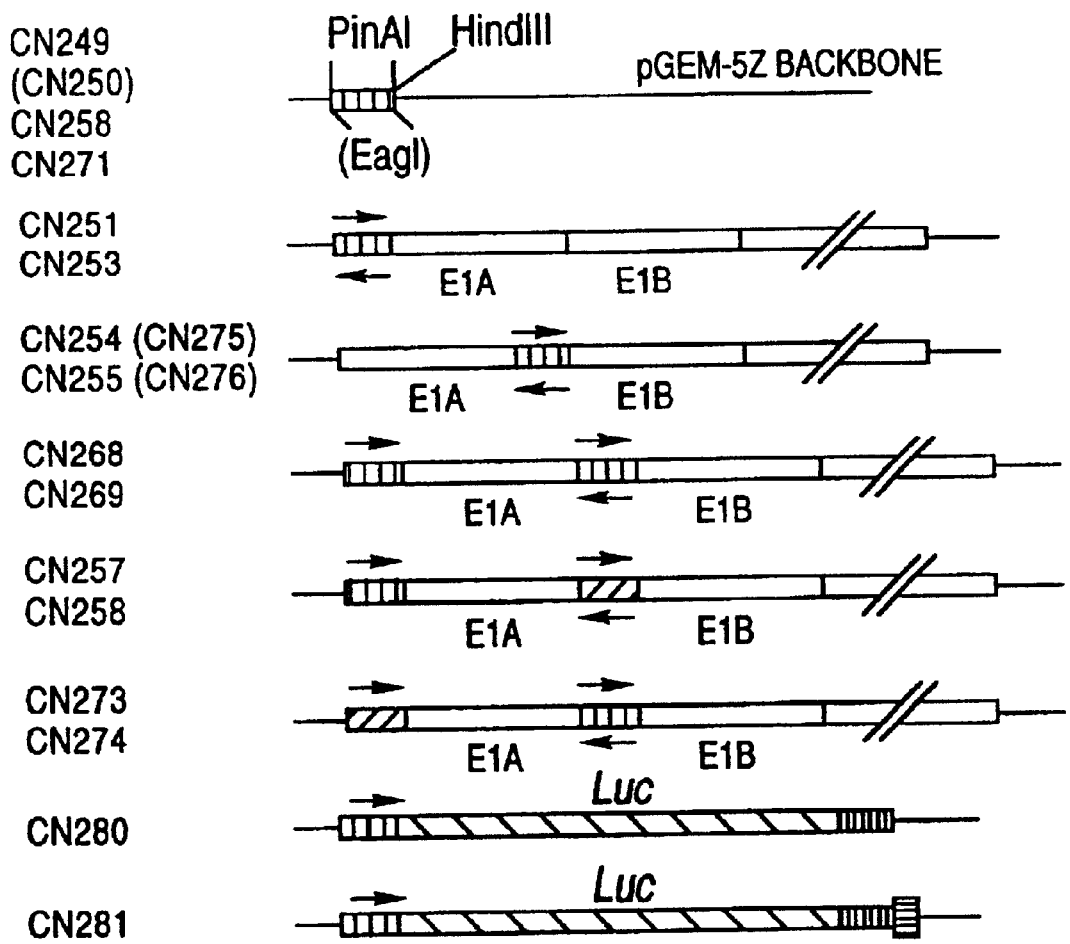
FIGS. 2A and 2B depict schematic diagrams of various adenovirus vectors in which various genes are under control of a PB-TRE.
Figure 2B:
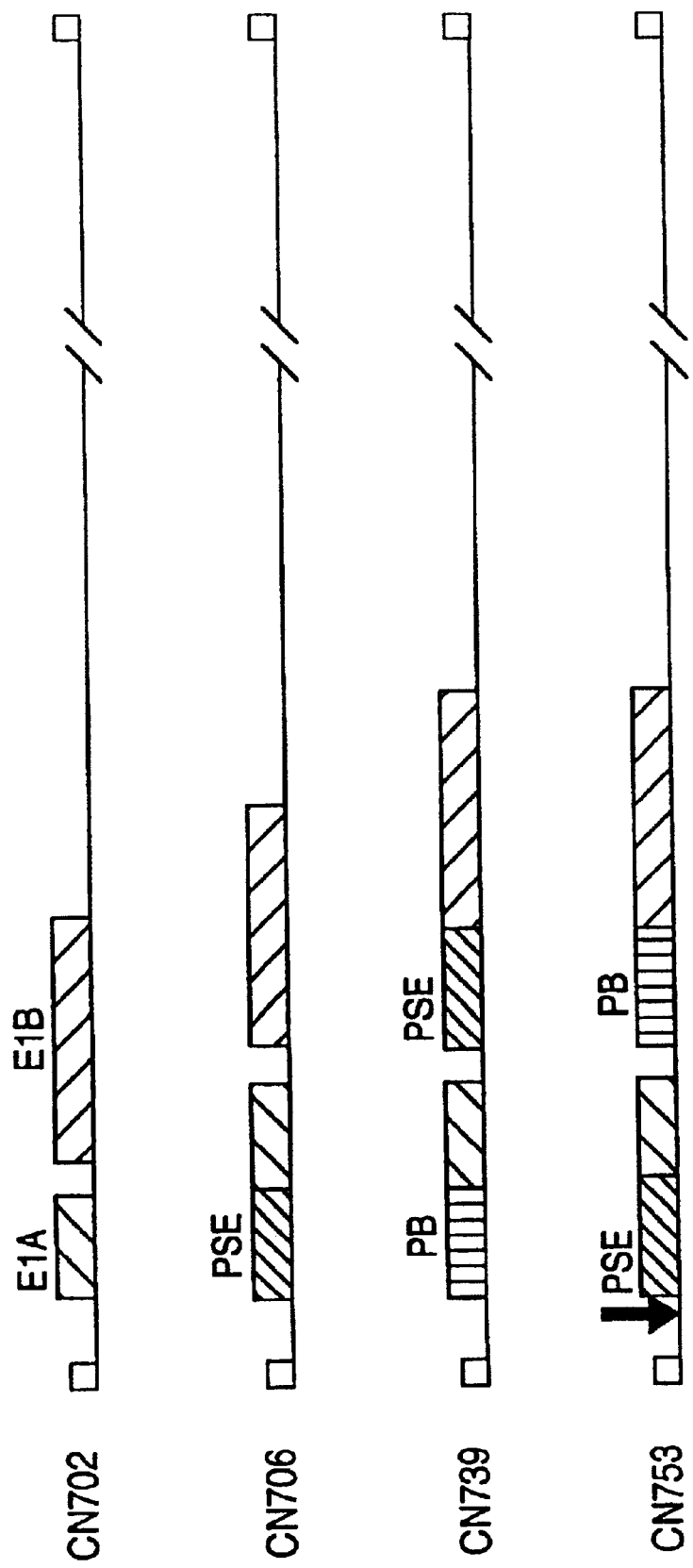

We have discovered and constructed replication-competent adenovirus vectors containing a probasin (PB) transcriptional regulatory element (PB-TRE) which can preferentially replicate in cells that allow a PB-TRE to function, such as prostate cells that express the androgen receptor (AR), and have developed methods using these adenovirus vectors. The adenovirus vectors of this invention can comprise at least one adenovirus gene under the transcriptional control of a PB-TRE, which is specifically up-regulated by binding of androgen receptor. The adenovirus gene can be, for example, a gene that contributes to cytotoxicity (directly or indirectly), such as a gene that is necessary for adenoviral replication. This replication gene is preferably at least one early gene. Alternatively, the adenovirus gene under control of a PB-TRE can be an adenovirus death protein (ADP) gene. Alternatively, the adenovirus gene under control of a PB-TRE can be a late replication gene. The adenovirus can optionally comprise at least one other gene such as an adenovirus gene or transgene under control of another TRE which is different from the PB-TRE. By providing for cell-specific transcription of at least one adenovirus gene required for replication, the invention provides adenovirus vectors that can be used for specific cytotoxic effects due to selective replication. Selective replication is especially useful in the cancer context, in which targeted cell killing is desirable. The adenovirus vectors are useful for treatment of cancers such as prostate. The vectors can also be useful for detecting the presence of androgen receptor-producing cells in, for example, an appropriate biological (such as clinical) sample. Further, the adenovirus vector(s) can optionally selectively produce one or more proteins of interest in a target cell by using a PB-TRE.

We have found that the adenovirus vectors of the invention replicate preferentially in cells that allow a PB-TRE to function, such as AR-producing cells (i.e., at a significantly higher yield than in non-AR producing cells). This replication preference is indicated by comparing the level of replication (i.e., titer) in cells that allow a PB-TRE to function to the level of replication in cells that do not allow a PB-TRE to function. The replication preference is even more significant, as the adenovirus vectors of the invention actually replicate at a significantly lower rate in cells that do not allow a PB-TRE to function than wild type virus. Comparison of the titer of a PB-producing cell type to the titer of a PB-deficient cell type provides a key indication that the overall replication preference is enhanced due to depressed replication in PB-deficient cells as well as the replication in PB-producing cells. Thus, the invention uses and takes advantage of what has been considered an undesirable aspect of adenoviral vectors, namely, their replication and possible concomitant immunogenicity. Runaway infection is prevented due to the cell-specific requirements for viral replication. Without wishing to be bound by any particular theory, the inventors note that production of adenovirus proteins can serve to activate and/or stimulate the immune system, either generally or specifically toward target cells producing adenoviral proteins which can be an important consideration in the cancer context, where patients are often moderately to severely immunocompromised.

Under at least some conditions, the PB-TRE is able to mediate a significantly higher degree of cell-specificity than two other prostate-specific TREs, the prostate specific antigen TRE (PSA-TRE) or the human glandular kallikrein TRE (hKLK2-TRE). In experiments with adenoviruses in which multiple adenoviral replication genes were under control of multiple prostate-specific TREs, the adenoviruses comprising PB-TRE demonstrated a significantly higher degree of cell-specific replication than viruses comprising a PSA-TRE or hKLK2-TRE. These results are described in detail in the Examples section. These findings are particularly surprising because human prostate cells were tested, and the PB-TRE is derived from rat, while the PSA-TRE and hKLK2-TRE are derived from human DNA.

As shown in the Examples section, two adenoviral vectors were constructed in which two adenovirus genes, E1A and E1B, are under control of a PSA-TRE or a PSA-TRE. E1A is arguably more important for viral replication than E1B, as E1A is expressed before any other viral genes, including E1B, and is required for E1B expression. Flint (1982) *Biochem. Biophys. Acta* 651:175–208; Flint (1986) *Advances Virus Research* 31:169–228; Grand (1987) *Biochem. J.* 241:25–38. The vector in which a PB-TRE controls E1A expression demonstrated an unexpectedly higher specificity of replication than the vector in which a PSA-TRF controls E1A. Thus, under at least some conditions, a PB-TRE may allow a greater degree of cell-specificity of viral replication than a PSA-TRE.

The PB-TRE is also more cell-specific than the TRE of the human glandular kallikrein-1 gene (hKLK2) or hKLK2-TRE. Like the probasin gene, the hKLK2 gene is expressed exclusively in the prostate, is up-regulated by androgens primarily by transcriptional activation, and contains AREs in its TRE. Wolf et al. (1992) *Molec. Endocrinol.* 6:753–762. Morris (1989) *Clin. Exp. Pharm. Physiol.* 16:345–351; Qui et al. (1990) *J. Urol.* 144:1550–1556; Young et al. (1992) *Biochem.* 31:818–824; Schedlich et al. (1987) *DNA* 6:429–437; Young et al. (1992) *Biochem.* 31:818–824; Schedlich et al. (1987) *DNA* 6:429–437; and Murtha et al. (1993) *Biochem.* 32:6459–6464. As shown in the Example section, in two separate adenoviral vectors, a PSE-TRE was placed in control of E1A expression. In one vector, E1B was controlled by a PB-TRE; in the other, a hKLK2-TRE controlled E1B expression. Thus, while PB-TRE and hKLK2 are both prostate-specific, the adenoviral vector in which PB-TRE controlled E1B unexpectedly demonstrated up to 8-fold greater cell-specificity in replication than the vector in which hKLK2 controlled E1B. Thus, under at least some conditions, a PB-TRE may allow a greater degree of cell-specificity of replication in human prostate cells than either of two other prostate-specific TREs, a PSA-TRE or an hKLK2-TRE. These results are even more surprising considering that a PB-TRE is rat-derived, while both a PSA-TRE and a hKLK2-TRE are human.

Data presented in the Examples section also show that an adenovirus in which two prostate-specific TREs control replication of two adenoviral genes is capable of treating LNCaP tumors in nude mice. After palpable tumors were established, the mice were injected with adenoviruses in which a PB-TRE controls E1A, and also a PSA-TRE controls E1B. Most of the animals (⁴⁄₇) were free of palpable tumors at day 42. This beneficial result was obtained with only a single dose of adenovirus. This study showed that an adenovirus of the present invention was efficacious against LNCaP tumor xenografts in vivo.

General Techniques The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; and Bett et al. (1994) *Proc. Natl. Acad Sci. USA* 91:8802–8806.

Definitions

A "probasin gene (PB) transcriptional response element", "probasin (PB) transcriptional regulatory element", "PB-TRE", "PBE", and the like indicate a polynucleotide sequence, preferably a DNA sequence, which increases transcription of an operably-linked polynucleotide sequence in a host cell that allows a PB-TRE to function, such as a host cell that expresses androgen receptor, such as a prostate cell. A PB-TRE thus increases the level of transcription of an operably linked DNA sequence in a prostate cell relative the level of transcription in a non-prostate cell. A PB-TRE comprises at least a portion of a PB promoter and/or a PB enhancer (which may include an ARE or androgen receptor binding site). The PB-TRE can comprise a heterologous (non-PB-TRE) promoter and a PB-TRE enhancer or a PB-TRE promoter and a heterologous enhancer. Methods are described herein for measuring the activity of a PB-TRE and thus for determining whether a given cell allows a PB-TRE to function.

As described in more detail herein, a PB-TRE can comprise any number of configurations, including, but not limited to, a PB promoter; a PB enhancer; a PB promoter and a PB enhancer (preferably comprising an ARE site); a PB promoter and a non-PB (heterologous) enhancer; a non-PB (heterologous) promoter and a PB enhancer; a non-PB promoter and multiple PB enhancers; and multimers of the foregoing. Methods are described herein for measuring the activity of a PB-TRE and thus for determining whether a given cell allows a PB-TRE to function. The promoter and enhancer of a PB-TRE may be in any orientation and/or distance from the coding sequence of interest, and comprise multimers of the foregoing. as long as the desired PB cell-specific transcriptional activity is obtained. Transcriptional activation can be measured in a number of ways known in the art (and described in more detail below), but is generally measured by detection and/or quantitation of mRNA or the protein product of the coding sequence under control of (i.e., operatively linked to) a PB-TRE. As discussed herein, a PB-TRE can be of varying lengths, and of varying sequence composition. By "transcriptional activation" or an "increase in transcription", it is intended that transcription will be increased above basal levels in the target cell (i.e. cells that allow a PB-TRE to function, such as AR-producing cell) by at least about 2-fold, preferably at least about 5-fold, preferably at least about 10-fold, more preferably at least about 20-fold, more preferably at least about 50-fold, more preferably at least about 100-fold, even more preferably at least about 200-fold, even more preferably at least about 400- to about 500-fold, even more preferably, at least about 1000-fold. Basal levels are generally the level of activity. if any, in a non-AR-producing cell, or the level of activity (if any) of a reporter construct lacking a PB-TRE as tested in an AR-producing cell. Optionally, a transcriptional terminator or transcriptional "silencer" can be placed upstream of the PB-TRE, thus preventing unwanted read-through transcription of the coding segment under transcriptional control of the PB-TRE. Also, optionally, the endogenous promoter of the coding segment to be placed under transcriptional control of the PB-TRE can be deleted.

A "functionally-preserved" variant of a PB-TRE is a PB-TRE which differs from another PB-TRE. but which still retains the ability to increase transcription of an operably linked polynucleotide, especially cell-specific transcription activity. The difference in a PB-TREs can be due to differences in linear sequence, arising from, for example, single or multiple base mutation(s), addition(s), deletion(s), insertion(s). and/or modification(s) of the bases. The difference can also arise from changes in the sugar(s), and/or linkage(s) between the bases of a PB-TRE.

As used herein, "prostate-specific gene expression" indicates gene expression which occurs primarily in prostate cells or in cells expressing gene products typical of prostate cells, but to a lesser degree in other cells. "Prostate-specific gene expression" indicates that this gene expression is at least about 2-fold, preferably at least about 5-fold, preferably at least about 10-fold, more preferably at least about 20-fold, more preferably at least about 50-fold, more preferably at least about 100-fold, even more preferably at least about 200-fold, even more preferably at least about 400- to about 500-fold, even more preferably, at least about 1000-fold, greater in prostate cells or in cells expressing gene products typical of prostate cells than in other cells. Genes demonstrating prostate-specific gene expression include, but are not limited to, prostate specific antigen and androgen receptor.

A "prostate-specific transcriptional response elementa", "prostate-specific transcriptional regulatory element", "prostate-specific TRE", "PS-TRE" and the like indicate a DNA segment capable of mediating (i.e., regulating) and/or enhancing prostate-specific gene expression. Such a segment is typified by, but not limited to, a probasin transcriptional regulatory element (PB-TRE) and prostate-specific antigen transcriptional regulatory element (PSA-TRE), the TRE of the human glandular kallikrein-1 gene (hGK-1 or 17KLK2, encoding the hK2 protein), transcriptional regulatory elements thereof which are capable of mediating prostate-specific gene expression.

"Prostate-specific antigen (PSA) promoter enhancer". "Prostate-specific antigen (PSA) transcriptional regulator) element," "PSA-TRE," "prostate specific antigen promoter-enhancer," "PSE", or the like, are defined herein as the transcriptional regulatory element(s) derived from the 5' region of the prostate specific antigen gene (PSA), and sufficient to mediate prostate-specific gene expression. A PSA-TRE comprises at least a portion of a PSA-TRE promoter and/or a PSA-TRE enhancer. The PSA-TRE can comprise a heterologous (non-PSA-TRE) promoter and a PSA-TRE enhancer, or a PSA-TRE promoter and a heterologous (non-PSA-TRE) enhancer. Methods are described herein for measuring the activity of a PSA-TRE and thus for determining whether a given cell allows a PSA-TRE to function.

The PSA-TRE depicted in SEQ ID NO:2 is the same as that given in GenBank Accession No. U37672, and published. Schuur et al. (1996) *J. Biol. Chem.* 271:7043–7051. A variant PSA-TRE nucleotide sequence is depicted in SEQ ID NO:3. This is the PSA-TRE contained within CN706 clone 35.190.13. CN706 is an adenoviral vector in which the E1A gene in Ad5 is under transcriptional control of a PSA-TRE. CN706 demonstrates selective cytotoxicity toward PSA-expressing cells in vitro and in vivo. Rodriguez et al. (1997) *Cancer Res.* 57:2559–2563. CN706 was passaged through 293 and LNCaP cells. A clone, designated 35.190.13 was isolated. The structure of this clone was confirmed by PCR, restriction endonuclease digestion and Southern blotting. Both DNA strands of the CN706 clone 35.190.13 were sequenced between positions 1 and 3537. Seven single base pair changes were found in the PSA-TRE, compared to the sequence reported by Schuur et al. (1996). These point mutations are not in the ARE and are thus not likely to affect the function of the enhancer. One mutation was found in the PSA promoter, but is not likely to affect gene expression from this promoter. In addition to these mutations, a missense mutation was found in the first exon of E1A. This C to G transition at position 3032 results in a Glu to Arg change in the E1A protein sequence. This mutation does not appear to diminish E1A function.

"Androgen receptor" as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In nonnal cells the AR is activated by androgen, but in non-normal cells (including malignant cells) the AR may be activated by non-androgenic agents, including hormones other than androgens. Encompassed in the term "androgen receptor" are mutant forms of an androgen receptor, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

An "adenovirus vector" or "adenoviral vector" (used interchangeably) is a term well understood in the art and generally comprises a polynucleotide (defined herein) comprising all or a portion of an adenovirus genome. For purposes of the present invention, an adenovirus vector contains a PB-TRE operably linked to a polynucleotide. The operably linked polynucleotide can be adenoviral or heterologous. An adenoviral vector construct of the present invention can be in an) of several forms, including, but not limited to, naked DNA, DNA encapsulated in an adenovirus coat, DNA packaged in another viral or viral-like form (such as herpes simplex virus and AAV), DNA encapsulated in liposomes, DNA complexed with polylysine, complexed with synthetic polycationic molecules, conjugated with transferrin, and complexed with compounds such as PEG to immunologically "mask" the molecule and/or increase halflife, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs. and modified and/or alternative backbone structures, such as polyamides. For purposes of this invention, adenovirus vectors are replication-competent in a target cell.

The term "polynucleotide" or "nucleic acid" as used herein refers to a polymeric form of nucleotides of any length, either ribonucleotides or deoxy ribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH$_2$) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothiate linkage can be used in place of a phosphodiester linkage. Braun et al. (1988) *J. Immunol.* 141: 2084–2; Latimer et al. (1995) *Mol. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rPNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs knoan in the art, for example, those described in *Current Protocols in Molecular Biology* (Ausubel et al., eds., 1987), Supp. 30, section 7.7.18, Table 7.7.1. A preferred alignment program is ALIGN Plus (Scientific and Educational Software, Pennsylvania).

As used herein, "a cell which allows a PB-TRE to function", a cell in which the function of a PB-TRE is "sufficiently preserved", "a cell in which a PB-TRE is functional" is a cell in which a PB-TRE, when operably linked to, for example, a reporter gene, increases expression of the reporter gene at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to 500-fold, even more preferably at least about 1000-fold, when compared to the expression of the same reporter gene when not operably linked to the PB-TRE. Methods for measuring levels (whether relative or absolute) of expression are known in the art and are described herein.

"Under transcriptional control" is a term well-understood in the art and indicates that transcription of a polynucleotide sequence. usually a DNA sequence, depends on its being operably (operatively) linked to an element which contributes to the initiation of, or promotes, transcription. As noted below, "operably linked" refers to a juxtaposition wherein the elements are in an arrangement allowing them to function.

As used herein, "cytotoxicity" is a term well understood in the art and refers to a state in which one or more of a cell's usual biochemical or biological functions are aberrantly compromised (i.e., inhibited or elevated). These activities include, but are not limited to, metabolism; cellular replication; DNA replication; transcription; translation; and uptake of molecules. "Cytotoxicity" includes cell death and/or cytolysis. Assays are knoan in the art which indicate cytotoxicity, such as dye exclusion, $^3$H-thymidine uptake, and plaque assays. The term "selective cytotoxicity", as used herein, refers to the cytotoxicity conferred by an adenovirus vector of the present invention on a cell which allows a PB-TRE to function when compared to the cytotoxicity conferred by the adenovirus on a cell which does not allowa PB-TRE to function. Such cytotoxicity may be measured, for example, by plaque assays, reduction or stabilization in size of a tumor comprising target cells, or the reduction or stabilization of serum levels of a marker characteristic of the tumor cells or a tissue-specific marker, e.g., a cancer marker such as prostate specific antigen.

"Replication" and "propagation" are used interchangeably and refer to the ability of a adenovirus vector of the invention to reproduce or proliferate. This term is well understood in the art. For purposes of this invention. replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

A "heterologous gene" or "transgene" is any gene that is not present in wild-type adenovirus. Preferably, the transgene will also not be expressed or present in the target cell prior to introduction by the adenovirus vector. Examples of preferred transgenes are provided below.

A "heterologous" promoter or enhancer is one which is not associated with or derived from a probasin gene 5' flanking sequence. Examples of a heterologous promoter or enhancer are the albumin promoter or enhancer and other viral promoters and enhancers, such as SV40.

An "endogenous" promoter, enhancer, or TRE is native to or derived from adenovirus.

The term "operably linked" relates to the orientation of polynucleotide elements in a functional relationship. A TRE is operably linked to a coding segment if the TRE promotes transcription of the coding sequence. Operably linked means that the DNA sequences being linked are generally contiguous and, where necessary to join two protein coding regions, contiguous and in the same reading frame. However, since enhancers generally function when separated from the promoter by several kilobases and intronic sequences may be of variable length, some polynucleotide elements may be operably linked but not contiguous.

A "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with an adenoviral vector of this invention.

A "target cell" is any cell that allows a PB-TRE to function. Preferably, a target cell is a mammalian cell which allows a PB-TRE to function, such as a cell expressing androgen receptor, preferably, a mammalian cell endogenously expressing androgen receptor, more preferably, a human cell, and more preferably, a human cell capable of allowing a PB-TRE to function and expressing an androgen receptor.

As used herein, "neoplastic cells", "neoplasia", "tumor", "tumor cells", "cancer", and "cancer cells" refer to cells which exhibit relatively autonomous growth, so that they exhibit an aberrant growth phenotype characterized by a significant loss of control of cell proliferation. Neoplastic cells can be benign or malignant.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates. serum, plasma, biological fluid, and tissue samples.

An "individual" is a vertebrate. preferably a mammal, more preferably a human. Mammals include, but are not limited to, farm animals, sport animals, and pets.

An "effective amount" is an amount sufficient to effect beneficial or desired clinical results. An effective amount can be administered in one or more administrations. For purposes of this invention, an effective amount of an adenoviral vector is an amount that is sufficient to palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering adenoviral vectors of the present invention.

Adenoviral Vectors Having Replication Specificity for Androge Receptor-producing Cells The present invention also provides adenoviral vector constructs which comprise an adenoviral gene under transcriptional control of a PB-TRE. Preferably the adenovirus gene is one that contributes to cytotoxicity (whether directly and/or indirectly), more preferably one that contributes to or causes cell death, and even more preferably the adenoviral gene under transcriptional control of a PB-TRE is a gene essential for adenoviral replication. Examples of an adenoviral gene that contributes to cytotoxicity include, but are not limited to, an adenoviral death protein (ADP). When the adenovirus vector(s) is selectively (i.e. preferentially) replication-competent for propagation in target cells allowing a PB-TRE to function, such as cells expressing androgen receptor (AR), these cells will be preferentially killed upon adenoviral proliferation. By combining the adenovirus vector(s) with the mixture of prostate and non-prostate cells, in vitro or in vivo, the adenovirus vector(s) preferentially replicate in the target prostate cells. Once the target cells are destroyed due to selective cytotoxic and/or cytolytic replication, the adenovirus vector replication is significantly reduced, thus lessening the probability of runaway infection and undesirable bystander effects. In vitro cultures may be retained to continually monitor the mixture (such as, for example, a biopsy or other appropriate biological sample) for occurrence (i.e. presence) and/or recurrence of the target cell. e.g., any cell that allows a PB-TRE to function, such as a an androgen receptor-producing cancer cell. To ensure cytotoxicity further, one or more transgenes having a cytotoxic effect may also be present and under selective transcriptional control. In this embodiment, one may provide higher confidence that the target cells will be destroyed. Additionally, or alternatively, an adenovirus gene that contributes to cytotoxicity and/or cell death (such as ADP) may be included in the adenoviral vector, either free of, or under, selective transcriptional control.

The PB-TREs used in this invention are derived from rodent cells, including, but not limited to, rat. Preferably the PB-TRE is derived from rat cells. In one embodiment, the PB-TRE comprises a promoter of a probasin gene. In one embodiment, the PB-TRE comprises an enhancer from a probasin gene. In another embodiment, the PB-TRE comprises a promoter from a probasin gene and an enhancer from a probasin gene. In certain embodiments wherein the PB-TRE comprises an enhancer from a probasin gene, the enhancer may be in combination with a promoter from a probasin gene or a promoter from another gene. In certain embodiments wherein the PB-TRE comprises a promoter from a probasin gene, the promoter may be in combination with an enhancer from a probasin gene or an enhancer from another gene. In addition, the PB-TRE can comprise multiple promoters and/or multiple enhancers derived from the probasin gene or another gene or other genes.

A DNA fragment comprising the 5'-flanking PB DNA, nt about −426 to about +28 (SEQ ID NO:1), carries sufficient information to direct prostate-specific, developmentally- and hormonally-regulated expression of a heterologous (non-probasin) gene in transgenic mice. Greenberg et al. (1994) Mol. Endocrinol. 8: 230–239; Foster et al. (1997) Cancer Res. 57:3325–30. Furthermore, this expression was both male-specific and restricted to the epithelial cells of the lateral, dorsal, and ventral prostate lobes. The demonstration that the foreign gene activity approached precastration levels when transgenic mice were supplemented with testosterone indicates that the PB-driven reporter transgene was responding to androgens in vivo. Moreover, a PB-TRE could drive expression of the simian virus 40 large tumor antigen-coding region in the prostate of the transgenic mice. Greenberg et al. (1995) Proc. Natl. Acad. Sci. 92: 3439–3443.

Accordingly, in one embodiment, a PB-TRE is the sequence upstream of the probasin coding segment, comprising, for example, the sequence shown in FIG.1 (SEQ ID NO:1). This sequence. e.g. from about −426 to about +28 relative to the transcriptional start site, comprises protein binding sites believed to be important or essential in cell-specific transcription, including ARE-1, ARE-2, a CAAT box, and a TATAA box.

Alternatively, a PB-TRE comprises, for example, the fragment of DNA upstream of the PB gene between base pairs about −286 and about +28 relative to the transcriptional start (nucleotides about 141 to about 454 of SEQ ID NO:1). Rennie et al. (1993) Mol. Endocrinol. 7:23–36. Sequence analysis revealed that this PB-TRE contains two ARE sites (designated ARE-1, also known as ARBS-1, which resembles a glucocorticoid response element, at about −236 to about −223 relative to the transcriptional start (nucleotides about 191 to about 204 of SEQ ID NO:1) and ARE-2, also known as ARBS-2, which is a unique sequence at about −140 to about −117 (nucleotides about 286 to about 310 of SEQ ID NO:1) required for androgen regulation. A single base mutation in ARE-1 or ARE-2 can result in the loss of androgen induction. Rennie et al. (1993) Mol. Endocrinol. 7:23–36. A fragment of 5'-flanking PB DNA containing the two ARE sites could drive expression of the bacterial chloramphenicol actyltransferase (CAT); expression was prostate-specific and inducible by androgens, but not by glucocorticoids. Greenberg et al. (1994) Mol. Endocrinol. 8:230–239. Like the probasin gene, the AR gene itself is regulated by two ARE sites upstream of the coding segment. The first AR gene ARE site, ARE-1. resembles a half-site of the palindromic hormone response element and the second. ARE-2, is identical to a portion of the probasin sequence. Dai et al. (1996) Mol. Endocrinol. 10:1582–94. A PB enhancer is exemplified by an ARE site or pair of ARE sites, or any other sequence capable of assisting a promoter in prostate-specific transcription. Proper spacing between ARE sites may also be important in their function.

A PB-TRE can also comprise multimers. For example, an a PB-TRE can comprise a tandem series of at least two, at least three, at least four, at least five PB promoter fragments. Alternatively, a PB-TRE could have one or more PB promoters along with one or more PB enhancers. These multimers may also contain non-PB promoter and/or enhancer sequences. Multiple AREs have been joined together in constructing a transcriptional regulatory element that is highly inducible by androgen receptor in vitro. Snoek et al. (1996) J. Steroid Biochem. Mol. Biol. 59:243–50. Base substitutions between ARE sites, if multiple ARE sites are included in a single PB-TRE, as is known in the art, are unlikely to cause alterations in cell-specific transcription. although deletions may decrease or increase transcription if they bring binding sites too close or too far away or rotate them so they are on opposite sides of the DNA helix, as is known in the art. Thus, while the inventors are not wishing to be bound by a single theory it is possible that certain modifications will result in modulated resultant expression levels, including enhanced cell-specific expression levels.

Any number of minor variations of the disclosed PB-TRE sequences are capable of mediating cell-specific transcription in cells which allow, a PB-TRE to function, such as androgen receptor-producing cells. Certain point mutations within a hexamer conserved in both the ARE-1 and ARE-2 sites in the PB-TRE are known to decrease AR binding and gene activation. Rennie et al. (1993). Taking into account the ARE consensus sequence and similarity of the AREs to the glucocorticoid-responsive element (GRE) motif found in androgen regulation of the C3(1) gene, PSA gene and the sex-limited protein gene [Rennie et al. (1993); Claessens et al. (1989) Biochem. Biophys. Res. Comm. 164:833–840; De Vos et al. (1991) J. Biol. Chem. 266:3439–3443; Riegman et al. (1992) Mol. Endocrin. 5: 1921–1930; Adler et al. (1991) Mol. Endocrin. 5:1587–1596; and Dai et al. (1996) Mol. Endocrinol. 10:1582–94], one of skill in the art would recognize that some alterations of highly conserved bases in and around the AREs are likely to negatively affect gene activation and cell-specificity, while alterations in bases which are not highly conserved are not likely to have such effects. Certain mutations are also capable of increasing PB-TRE activity, such as the alteration within ARE-2 of four bases at −130to −127 from CCAA to TACT or GTCT, which demonstrated greater induction than the wild-type PB-TRE. International Application PCT/CA93/003 13, published as WO 94/03594, Feb. 17, 1994, to Matusk. Testing of the effects of altering bases may be performed in vitro or in vivo by any method known in the art, such as mobility shift assays, or transfecting vectors containing these alterations in AR-expressing and non-AR-expressing cells.

Figure 3:
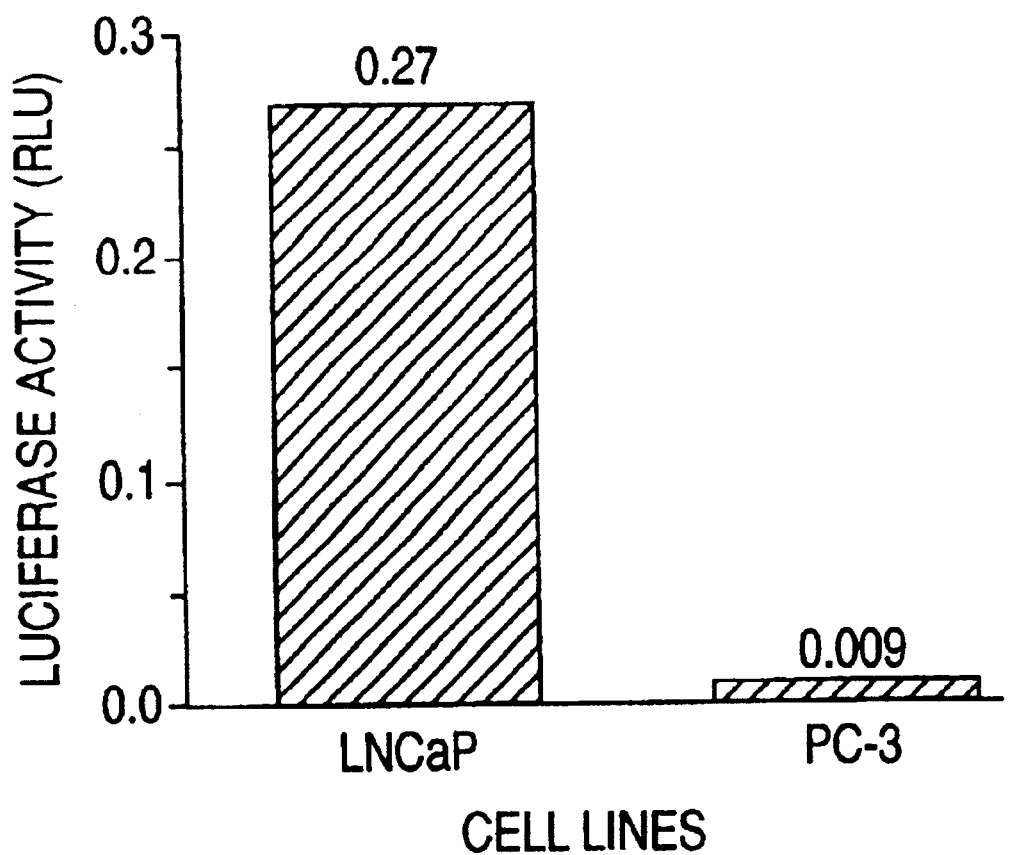
FIG. 3 is a bar graph depicting results of a luciferase assay demonstrating cell-specific gene expression driven by a PB-TRE in LNCaP (PSA-plus and androgen-dependent prostate carcinoma cells) and PC-3 (PSA-minus and androgen-independent prostate carcinoma cells).

As an example of how PB-TRE activity can be determined, a polynucleotide sequence or set of such sequences can be generated using methods known in the art, such as chemical synthesis, site-directed mutagenesis, PCR, and/or recombinant methods. The sequence(s) to be tested can be inserted into a vector containing an appropriate reporter gene encoding a reporter protein, including, but not limited to, chloramphenicol acetyl transferase (CAT), β-galactosidase (encoded by the lacZ gene), luciferase, (encoded by the luc gene), alkaline phosphatase, green fluorescent protein, and horse radish peroxidase. Such vectors and assays are readily available, from, inter alia, commercial sources. Plasmids thus constructed are transfected into a suitable host cell to test for expression of the reporter gene as controlled by the putative PB-TRE using transfection methods known in the art, such as calcium phosphate precipitation, electroporation, liposomes (lipofection), and DEAE dextran. Suitable host cells include any cell type that produces androgen receptor, including but not limited to, prostate cells, including prostate tumor cells such as LNCaP. A gene encoding androgen receptor can be transformed into and expressed in any cell that does not normally express AR; in such a cell, a PB-TRE will be functional. Non-androgen receptor producing cells, such as HLF, HLE, and 3T3 and the non-AR-producing prostate cancer cells PC3 and DU145 can be used as a control. Results are obtained by measuring the level of expression of the reporter gene using standard assays. The comparison of expression between AR-producing cells and the control cell indicates the presence or absence of transcriptional activation. FIG. 3 is a bar graph depicting results of a luciferase assay demonstrating cell-specific gene expression driven by a PB-TRE in LNCaP (PSA-plus and androgen-dependent prostate carcinoma cells) and PC-3 (PSA-minus and androgen-independent prostate carcinoma cells).

A PB-TRE of the present invention may or may not lack a silencer. The presence of a silencer (i.e., a negative regulatory element known in the art) can assist in shutting off transcription (and thus replication) in non-permissive (i.e., non-AR-producing) cells. Thus, presence of a silencer can confer enhanced cell-specific replication by more effectively preventing adenoviral vector replication in non-target cells. Alternatively, lack of a silencer may assist in effecting replication in target cells. thus conferring enhanced cell-specific replication due to more effective replication in target cells.

As is readily appreciated by one skilled in the art, a PB-TRE is a polynucleotide sequence, and, as such, can exhibit function over a variety of sequence permutations. Methods of nucleotide substitution, addition, and deletion are known in the art, and readily available functional assays (such as the CAT or luciferase reporter gene assay) allow one of ordinary skill to determine whether a sequence variant exhibits requisite cell-specific transcription function.

Hence, the invention also includes adenovirus vectors comprising functionally preserved variants of the PB-TRE nucleic acid sequences disclosed herein, which include nucleic acid substitutions, additions, and/or deletions. It is possible that certain base modifications will result in enhanced expression levels or cell-specificity. Achievement of enhanced expression levels may be especially desirable in the case of more aggressive forms of prostate carcinoma, or when a more rapid and/or aggressive pattern of cell killing is warranted (due to an immunocompromised condition of the individual, for example).

Various replication-competent adenovirus vectors can be made according to the present invention in which a single or multiple adenovirus gene(s) are under control of a PB-TRE.

For example, a PB-TRE may be introduced into an adenovirus vector immediately upstream of and operably linked to (i.e. oriented in such a way as to be able to drive expression of) a replication gene. e.g. an early gene such as E1A or E1B or a late gene such as L1, L2, L3, L4, or L5.

Various other replication-competent adenovirus vectors can be made according to the present invention in which, in addition to having an adenovirus gene(s) are under control of a PB-TRE, other adenovirus gene(s) are under control of another exogenous (non-adenovirus) promoter. This promoter may be a tissue-specific promoter-enhancer, for instance the PSA-TRE (prostate-specific antigen transcriptional regulatory element) of the prostate specific antigen gene (PSA), which is preferentially expressed in prostate cells. In one embodiment, the PSA-TRE comprises an approximately 1.5 kb enhancer and a 0.5 kb promoter segment derived from the native region upstream of the PSA coding segment. The enhancer in humans is located between nt −5322 and nt −3739, relative to the transcription start site of the prostate specific antigen (PSA) gene. The promoter consists of about nt −540 to nt about +12. In another embodiment, the PSA-TRE is present on a single fragment about 5 to about 6 kb upstream from the transcriptional start site and comprising a PSA-TRE enhancer and a PSA-TRE promoter. The enhancer contains three regions that bind prostate-specific DNA binding proteins, one of which contains a putative androgen response element. The promoter contains typical TATA and CAAT boxes as well as a second putative androgen response element. A PSA-TRE can comprise a non-PSA-TRE promoter in combination with a PSA-TRE enhancer(s), or a PSA-TRE promoter in combination with a non-PSA-TRE enhancer(s), provided that the combination mediates prostate-specific gene expression. The PSA-TRE is more fully described in, inter alia, U.S. Pat. Nos. 5,648,478 and 5,698,443; and Lundwall et al. (1987) *FEBS Lett.* 214: 317; Lundwall (1989) *Biochem. Biophys. Res. Commun.* 161:1151–1159; Riegmann et al. (1991) *Molec. Endocrin.* 5: 1921; Schuur et al. (1996) *J. Biol. Chem.* 271: 7043–7051; and Zhang et al. (1997) *Nucleic Acids Res.* 25:3143–50.

A PB-TRE may be introduced into an adenovirus vector immediately upstream of and operably linked to an early gene such as E1A, and the PSA-TRE may be introduced immediately upstream of and operably linked to another early gene such as E1B. Alternatively, a PB-TRE may be introduced upstream of and operably linked to E1B, while the PSA-TRE is introduced immediately upstream of and operably linked to E1A.

Figure 4:
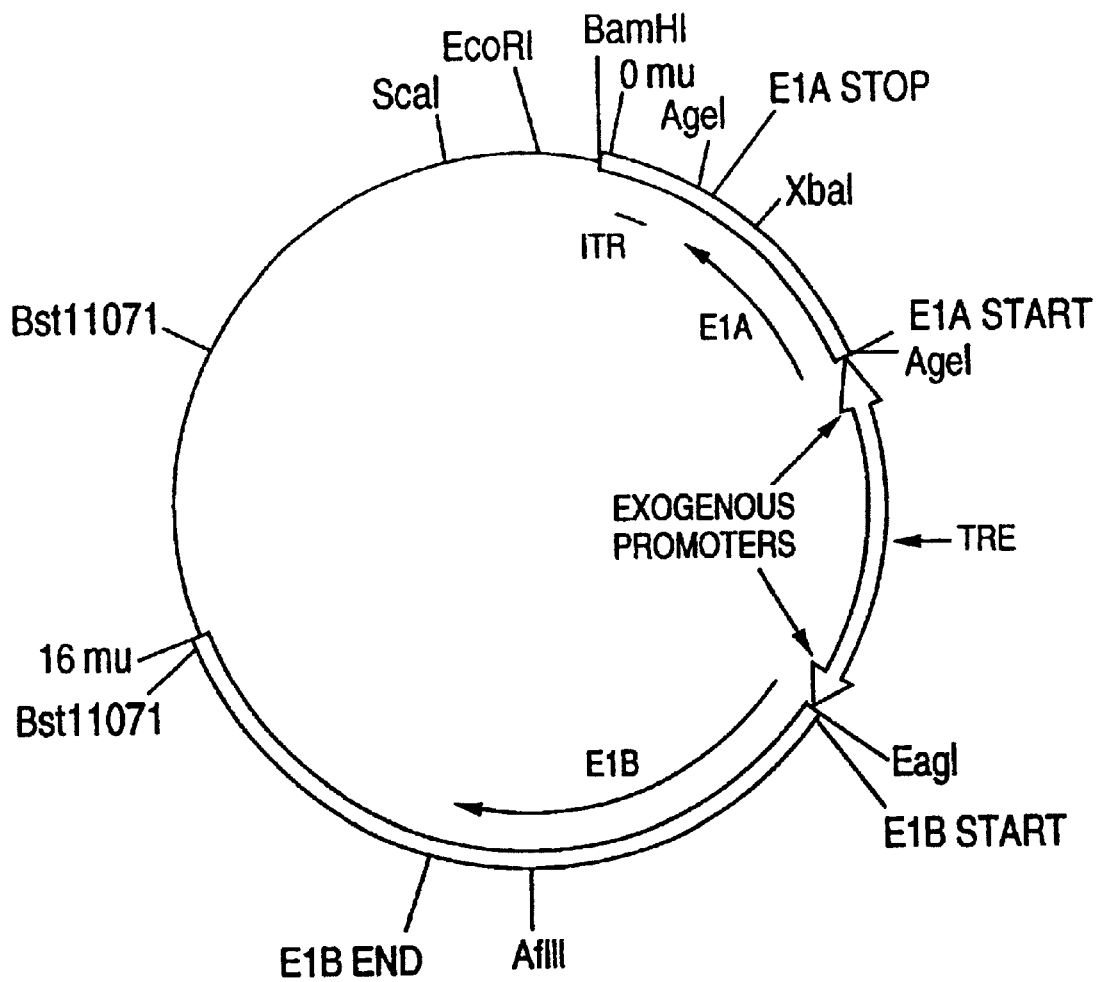
FIG. 4 is a schematic depiction of an adenoviral vector in which E1A and E1B are under control of an PB-TRE, with E1A and E1B in opposite orientations.

In one embodiment, E1A and E1B are under control of one or more PB-TREs by making the following construct. In wild-type adenovirus, E1A and E1B are in tandem orientation. A fragment containing the coding region of E1A through the E1B promoter is excised from the adenovirus genome and reinserted in the opposite orientation (FIG. 4). In this configuration, the E1A and E1B promoters are next to each other, followed by E1A coding segment in opposite orientation (so that neither the E1A or E1B promoters are operably linked to E1A), followed by E1B in opposite orientation with respect to E1A. An PB-TRE(s) can be inserted between E1A and E1B coding regions, (which are in opposite orientation), so that these regions are under control of the TRE(s). Appropriate promoter sequences are inserted proximal to the E1A and E1B region as shown in FIG. 4. Thus, an PB-TRE may drive both E1A and E1B. Such a configuration may prevent, for example, possible loop-out events that may occur if two PB-TREs were inserted in intact (native) Ad genome, one each 5' of the coding regions of E1A and E1B. By introducing a polycloning site between E1A and E1B, other types of prostate-specific TREs can be inserted, such as a transcriptional regulatory element of the prostate-specific antigen (PSA-TRE); or other cell-specific regulatory elements, preferably those associated with a disease state, such as neoplasm. Thus, this construct may find general use for cell-specific, temporal, or other means of control of adenovirus genes E1A and E1B, thereby providing a convenient and powerful way to render adenoviral replication dependent upon a chosen transcriptional parameter.

As shown in the Examples section, adenovirus vectors in which more than one adenovirus replication gene is under control of a prostate-specific TRE demonstrated an unexpectedly higher degree of cell-specificity of replication compared to adenovirus vectors in which only one gene is controlled by a PB-TRE. In one vector, placing both E1A and E1B under transcriptional control of copies of a PB-TRE demonstrated synergy; the cell-specificity of replication was unexpectedly better than that when only E1A was controlled by PB-TRE. In another vector, placing two adenoviral replication genes under control of two different prostate-specific TREs, a PB-TRE and a PSA-TRE, allowed a much greater specificity than placing a single gene under control of a prostate-specific TRE (PSA-TRE).

Various other replication-competent adenovirus vectors can be made according to the present invention in which, in addition to having a single or multiple adenovirus gene(s) are under control of a PB-TRE, reporter gene(s) are under control of a PB-TRE.

For example, a PB-TRE may be introduced into an adenovirus vector immediately upstream of and operably linked to an early gene such as E1A or E1B, and this construct may also contain a second PB-TRE driving expression of a reporter gene. The reporter gene can encode a reporter protein, including, but not limited to, chloramphenicol acetyl transferase (CAT), β-galactosidase (encoded by the lacZ gene), luciferase, alkaline phosphatase, green fluorescent protein, and horse radish peroxidase. For detection of a putative prostate cell(s) in a biological sample, the biological sample may be contacted with a modified adenoviral vector in which a reporter gene (e.g., luciferase) is under control of a PB-TRE. The PB-TRE will be transcriptionally active in cells that allow a PB-TRE to function (e.g. those cells expressing androgen receptor), and luciferase will be produced. This production allows detection of cells producing androgen receptor in, for example, a human host or a biological sample. Alternatively, an adenovirus vector can be constructed in which the gene encoding a product conditionally required for survival (e.g., an antibiotic resistance marker) is under control of a PB-TRE. When this adenovirus vector is introduced into a biological sample, cells producing androgen receptor will become antibiotic resistant. An antibiotic can then be introduced into the medium to kill cells that do not allow a PB-TRE to function.

By "transcriptional activation" or an "increase in expression", it is intended that transcription is increased above basal levels in the target cell (i.e., a cell that allows a PB-TRE to function, such as an AR-producing cell) by at least about 2-fold, preferably at least about 5-fold, preferably at least about 10-fold. more preferably at least about 20-fold, more preferably at least about 50-fold, more preferably at least about 100-fold, more preferably at least about 200-fold, even more preferably at least about 400- to about 500-fold, even more preferably at least about 1000-fold. Comparisons between or among various PB-TREs can be assessed, for example, by measuring and comparing levels of expression within a single AR-producing cell line. It is understood that absolute transcriptional activity of a PB-TRE will depend on several factors, such as the nature of the target cell, delivery mode and form of a PB-TRE, and the coding sequence that is to be selectively transcriptionally activated. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the CMV immediate early promoter. This analysis can also indicate negative regulatory regions, i.e., silencers.

It is understood that, to practice this invention, it is not necessary to use PB-TREs having maximum activity, or having minimum size. The requisite degree of activity is determined, inter alia, by the anticipated use and desired result. For example, if an adenoviral vector of the invention is used to monitor cells for androgen receptor-producing activity, it is possible that less than maximal degree of responsiveness by a PB-TRE will suffice to qualitatively indicate the presence of such cells. Similarly, if used for treatment or palliation of a disease state, less-than-maximal responsiveness may be sufficient for the desired result, if, for example, the androgen receptor-producing cells are not especially virulent and/or the extent of disease is relatively confined.

The size of a PB-TRE will be determined in part by the capacity of the adenoviral vector, which in turn depends upon the contemplated form of the vector (see below). Generally a minimal size is preferred, as this provides potential room for insertion of other sequences which may be desirable, such as transgenes (discussed below) or other additional regulatory sequences. However, if no additional sequences are contemplated, or if, for example, an adenoviral vector will be maintained and delivered free of any viral packaging constraints, a larger DNA sequence may be used as long as the resultant adenoviral vector is rendered replication-competent.

If no adenovirus sequences have been deleted, an adenoviral vector can be packaged with extra sequences totaling up to about 5% of the genome size, or approximately 1.8 kb. If non-essential sequences are removed from the adenovirus genome, then an additional 4.6 kb of insert can be tolerated (i.e., a total of about 1.8 kb plus 4.6 kb, which is about 6.4 kb). Examples of non-essential adenoviral sequences that can be deleted are E3 and E4 (as long as the E4 ORF6 is maintained).

In order to minimize non-specific replication, endogenous (i.e., adenovirus) TREs should preferably be removed. This would also provide more room for inserts in an adenoviral vector. which may be of special concern if an adenoviral vector will be packaged as a virus (see below). Even more importantly, deletion of endogenous TREs would prevent a possibility of a recombination event whereby a PB-TRE is deleted and the endogenous TRE assumes transcriptional control of its respective adenovirus coding sequences (thus allowing non-specific replication). In one embodiment, an adenoviral vector of the invention is constructed such that the endogenous transcription control sequences of an adenoviral gene(s) are deleted and replaced by a PB-TRE. However, endogenous TREs may be maintained in the adenovirus vector(s), provided that sufficient cell-specific replication preference is preserved. These embodiments can be constructed by providing a PB-TRE intervening between the endogenous TRE and the replication gene coding segment. Requisite cell-specific replication preference is indicated by conducting assays that compare replication of the adenovirus vector in a cell expressing androgen receptor with replication in a non-androgen receptor producing cell. Generally, it is intended that replication is increased above basal levels in the target cell (i.e., a cell that allows a PB-TRE to function, such as a AR-producing cell) by at least about 2-fold, preferably at least about 5-fold, preferably at least about 10-fold more preferably at least about 20-fold, more preferably at least about 50-fold, more preferably at least about 100-fold, more preferably at least about 200-fold, even more preferably at least about 400- to about 500-fold, even more preferably at least about 1000-fold. The acceptable differential can be determined empirically (using, for example, Northern assays or other assays known in the art or assays described in the Examples section) and will depend upon the anticipated use of the adenoviral vector and/or the desired result.

Suitable target cells are any cell type that allows a PB-TRE to function. Preferred are cells that express or produce androgen receptor, including, but not limited to, tumor cells expressing androgen receptor. Especially preferred are prostate carcinoma cells and any metastases that produce AR. Especially preferred are those cells in which androgen receptor production can be measured using assays standard in the art such as RIA, ELISA, or Western blots (immunoassays) to determine levels of AR protein production or Northern blots to determine levels of AR mRNA production. Alternatively, such cells can be identified and/or characterized by their ability to transcriptionally activate a PB-TRE (i.e., allow an AFP-TRE to function).

Any of the various serotypes of adenovirus can be used, such as Ad2, Ad5, Ad12, and Ad40. For purposes of illustration the serotype Adenovirus 5 (Ad5) is exemplified herein.

In some embodiments, a PB-TRE is used with an adenovirus gene that is essential for propagation, so that replication-competence is preferentially achievable in the target cell that allow a PB-TRE to function, such as a cell expressing androgen receptor. Preferably, the gene is an early gene, such as E1A, E1B, E2, or E4. (E3 is not essential for viral replication.) More preferably, the early gene under PB-TRE control is E1A and/or E1B. More than one early gene can be placed under control of a PB-TRE or another prostate-specific TRE. Example 1 provides a more detailed description of such constructs.

The E1A gene is expressed immediately after viral infection (0–2 hours) and before any other viral genes. E1A protein acts as a trans-acting positive-acting transcriptional regulatory factor, and is required for the expression of the other early viral genes E1B, E2, E3, E4, and the promoter-proximal major late genes. Despite the nomenclature, the promoter proximal genes driven by the major late promoter are expressed during early times after Ad5 infection. Flint (1982) Biochem. Biophys. Acta 651:175–208; Flint (1986) Advances Virus Research 31:169–228; Grand (1987) Biochem. J. 241:25–38. In the absence of a functional E1A gene, viral infection does not proceed, because the gene products necessary for viral DNA replication are not produced. Nevins (1989) Adv. Virus Res. 31:35–81. The transcription start site of Ad5 E1A is at nt 498 and the ATG start site of the E1A protein is at nt 560 in the virus genome.

The E1B protein functions in trans and is necessary for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey et al. (1993) Virology 193:631; Bailey et al. (1994) Virology 202:695–706. E1B proteins are also necessary for the virus to overcome restrictions imposed on viral replication by the host cell cycle and also to reduce the apoptotic effects of E1A. Goodrum et al. (1997) J. Virology 71:548–561. The E1B promoter of Ad5 consists of a single high-affinity recognition site for Sp1 and a TATA box.

The E2 region of adenovirus codes for proteins related to replication of the adenoviral genome, including the 72-kDa DNA-binding protein, the 80-kDa precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site.

For a detailed review of the E2 promoter architecture see Swaminathan et al., Curr. Topics in Micro. and Imm. (1995) 199 part 3:177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kDa protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor binding sites E2F and ATF. Therefore, insertion of a PB-TRE having SpeI ends into the SpeI site in the 1-strand would disrupt the endogenous E2 early promoter of Ad5 and should allow AR-restricted expression of E2 transcripts.

The E4 gene produces a number of transcription products. The E4 region codes for two polypeptides which are responsible for stimulating the replication of viral genomic DNA and for stimulating late gene expression. The protein products of open reading frames (ORFs) 3 and 6 can both perform these functions by binding the 55-kDa protein from E1B and heterodimers of E2F-1 and DP-1. The ORF 6 protein requires interaction with the E1B 55-kDa protein for activity while the ORF 3 protein does not. In the absence of functional protein from ORF 3 and ORF 6, plaques are produced with an efficiency less than $10^{-6}$ that of wild type virus. To further restrict viral replication to cells that allow a PB-TRE to function, such as AR-producing cells, E4 ORFs 1–3 can be deleted, making viral DNA replication and late gene synthesis dependent on E4 ORF 6 protein. By combining such a vector with sequences in which the E1B region is regulated by a PB-TRE, a virus can be obtained in which both the E1B function and E4 function are dependent on a PB-TRE driving E1B.

The major late genes relevant to the subject invention are L1, L2, L3, L4, and L5, which encode proteins of the Ad5 virus virion. All of these genes (typically coding for structural proteins) are probably required for adenoviral replication. The late genes are all under the control of the major late promoter (MLP), which is located in Ad5 at about +5986 to about +6048.

In addition to conferring selective cytotoxic and/or cytolytic activity by virtue of preferential replication competence in cells that allow a PB-TRE to function, such as cells expressing androgen receptor, the adenovirus vectors of this invention can further include a heterologous gene (transgene) under the control of a PB-TRE. In this way, various genetic capabilities may be introduced into target cells allowing a PB-TRE to function, such as cells expressing androgen receptor, particularly prostate carcinoma cells. For example, in certain instances, it may be desirable to enhance the degree and/or rate of cytotoxic activity, due to, for example, the relatively refractory nature or particular aggressiveness of the androgen receptor-producing target cell. This could be accomplished by coupling the cell-specific replicative cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin [Palmiter et al. (1987) *Cell* 50: 435; Maxwell et al. (1 987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *Mol. Cell. Biol.* 9: 415], genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly, genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1, -2, -6, -12, GM-CSF, G-CSF, M-CSF, IFN-α, -β, -γ, TNF-α, -β, TGF-α, -β, NGF; and the like. The positive effector genes could be used in an early phase, followed by cytotoxic activity due to replication.

In some embodiments, the adenovirus death protein (ADP), encoded within the E3 region, is maintained (i.e. contained) in the adenovirus vector (FIG. 5). The ADP gene, under control of the major late promoter (MLP), appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/or a lower dosage requirement. See Example 6.

Accordingly, the invention provides an adenoviral vector that includes a polynucleotide sequence encoding an ADP. A DNA sequence encoding an ADP and the amino acid sequence of an ADP are depicted in SEQ ID NO:2 1 and SEQ ID NO:22, respectively. Briefly, an ADP coding sequence is obtained preferably from Ad2 (since this is the strain in which ADP has been more fully characterized) using techniques known in the art, such as PCR. Preferably, the Y leader (which is an important sequence for correct expression of late genes) is also obtained and ligated to the ADP coding sequence. The ADP coding sequence (with or without the Y leader) can then be introduced into the adenoviral genome, for example, in the E3 region (where the ADP coding sequence will be driven by the MLP or the E3 promoter). The ADP coding sequence could also be inserted in other locations of the adenovirus genome, such as the E4 region. Alternatively, the ADP coding sequence could be operably linked to a heterologous promoter (with or without enhancer(s)), including, but not limited to, another viral promoter, a prostate-specific promoter such as the rat probasin TRE (PB-TRE).

In some embodiments, the invention provides adenoviral vectors which comprise an additional adenovirus gene under transcriptional control of a second PB-TRE. Examples of an additional adenovirus gene under transcriptional control is ADP (discussed above) and genes necessary for replication, such as earl) genes. For example, an adenoviral vector can be constructed such that a first PB-TRE regulates transcription of one early gene, such as E1A or E1B. and a second PB-TRE regulates transcription of another early gene. These multiple constructs may be more desirable in that they provide more than one source of cell specificity with respect to replication. As shown in the Examples section, such a double construct successfully inhibited tumor growth in mice harboring tumor xenografts.

Any of the adenoviral vectors described herein can be used in a variety of forms, including, but not limited to, naked polynucleotide (usually DNA) constructs. Adenoviral vectors can, alternatively, comprise polynucleotide constructs that are complexed with agents to facilitate entry into cells. such as cationic liposomes or other compounds such as polylysine; packaged into infectious adenovirus particles (which may render the adenoviral vector(s) more immunogenic); packaged into other particulate viral forms such as HSV or AAV; complexed with agents to enhance or dampen an immune response; or complexed with agents that facilitate in vivo transfection, such as DOTMA, DOTAP™, and polyamines.

The invention also provides an adenovirus capable of replicating preferentially in cells which allow a PB-TRE to function, such as androgen-receptor-producing cells. "Replicating preferentially in an androgen-receptor-producing cell" means that the adenovirus replicates more in a cell producing all the factors and co-factors needed for PB expression than in a cell not producing such factors and co-factors. Preferably, the adenovirus replicates at a significantly higher level in cells that allow a PB-TRE to function, such as AR-producing cells than non-AR-producing cells; preferably, at least about 2-fold higher, preferably at least about 5-fold higher, more preferably at least about 10-fold higher, still more preferably at least about 50-fold higher, even more preferably at least about 100-fold higher, still more preferably at least about 400-to about 500-fold higher, still more preferably at least about 1000-fold higher, most preferably at least about $1 \times 10^6$ higher. Most preferably, the adenovirus replicates solely in AR-producing cells (that is, does not replicate or replicates at very low levels in non AR-producing cells).

If an adenoviral vector comprising an adenovirus polynucleotide is packaged into a whole adenovirus (including the capsid), the adenovirus itself may be selected to further enhance targeting. For example, adenovirus fibers mediate primary contact with cellular receptor(s) aiding in tropism. See, e.g., Amberg et al. (1997) *Virol.* 227:239–244. If a particular subgenus of an adenovirus serotype displayed tropism for a target cell type and/or reduced affinity for non-target cell types, such subgenus (or subgenera) could be used to further increase cell-specificity of cytotoxicity and/or cytolysis.

The adenoviral vectors may be delivered to the target cell in a variety of ways, including, but not limited to, liposomes, general transfection methods that are well known in the art, such as calcium phosphate precipitation, electroporation, direct injection, and intravenous infusion. The means of delivery will depend in large part on the particular adenoviral vector (including its form) as well as the type and location of the target cells (i.e., whether the cells are in vitro or in vivo).

If used in packaged adenoviruses, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 µg to 1000 µg of an adenoviral vector can be administered. The adenoviral vector(s) may be administered one or more times, depending upon the intended use and the immune response potential of the host or may be administered as multiple simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

The present invention also provides host cells comprising (i.e., transformed with) the adenoviral vectors described herein. Both prokaryotic and eukaryotic host cells can be used as long as sequences requisite for maintenance in that host, such as appropriate replication origin(s), are present. For convenience, selectable markers are also provided. Host systems are known in the art and need not be described in detail herein. Prokaryotic host cells include bacterial cells, for example, *E. coli, B. subtilis*, and mycobacteria. Among eukaryotic host cells are yeast, insect, avian, plant, *C. elegans* (or nematode) and mammalian host cells. Examples of fungi (including yeast) host cells are *S. cerevisiae, Kluyveromyces lactis* (*K lactis*), species of Candida including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, mouse L cells, LNCaP cells, Chinese hamster ovary (CHO) cells, human embryonic kidney (HEK) cells, and African green monkey cells. *Xenopus laevis* oocytes, or other cells of amphibian origin, may also be used. Suitable host cells also include any cells which allow a PB-TRE to function, such as cells that produce androgen receptor and/or proteins and other factors necessary for expression of the probasin gene, whether the AR and/or other factors are produced naturally or recombinantly.

The present invention also includes compositions, including pharmaceutical compositions, containing the adenoviral vectors described herein. Such compositions are useful for administration in vivo, for example, when measuring the degree of transduction and/or effectiveness of cell killing in an individual. Preferably, these compositions further comprise a pharmaceutically acceptable excipient. These compositions, which can comprise an effective amount of an adenoviral vector of this invention in a pharmaceutically acceptable excipient, are suitable for systemic administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical Sciences*, 18the Edition, Mack Publishing (1990). Compositions also include lyophilized and/or reconstituted forms of the adenoviral vectors (including those packaged as a virus, such as adenovirus) of the invention.

The present invention also encompasses kits containing an adenoviral vector of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow someone to detect the presence of cells that allow a PB-TRE to function, such as androgen receptor-producing cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Preparation of the Adenovirus Vectors of the Invention

The adenovirus vectors of this invention can be prepared using recombinant techniques that are standard in the art. Generally, a PB-TRE is inserted 5 to the adenoviral gene of interest, preferably an adenoviral replication gene, more preferably one or more early replication genes (although late gene(s) can be used). A PB-TRE can be prepared using oligonucleotide synthesis (if the sequence is known) or recombinant methods (such as PCR and/or restriction enzymes). Convenient restriction sites either in the natural adeno-DNA sequence or introduced by methods such as PCR or site-directed mutagenesis. provide an insertion site for a PB-TRE. Accordingly, convenient restriction sites for annealing (i.e., inserting) a PB-TRE can be engineered onto the 5' and 3' ends of a PB-TRE using standard recombinant methods, such as PCR.

Polynucleotides used for making adenoviral vectors of this invention may be obtained using standard methods in the art such as chemical synthesis recombinant methods and/or obtained from biological sources.

Adenoviral vectors are conveniently prepared by homologous recombination or in vitro ligation of two plasmids, one providing the left-hand portion of adenovirus and the other providing the right-hand portion, one or both of which contains at least one adenovirus gene under control of a PB-TRE. If homologous recombination is used, the two plasmids should share at least about 500 bp of sequence overlap. Each plasmid, as desired. may be independently manipulated, followed by cotransfection in a competent host, providing complementing genes as appropriate, or the appropriate transcription factors for initiation of transcription from a PB-TRE for propagation of the adenovirus. Plasmids are generally introduced into a suitable host cell such as 293 cells or LNCaP cells, etc., using appropriate means of transduction, such as cationic liposomes. Alternatively, in vitro ligation of the right and left-hand portions of the adenovirus genome can be used to construct recombinant adenovirus derivative containing all the replication-essential portions of adenovirus genome. Berkner et al. (1983) *Nucleic Acid Research* 11:60036020; Bridge et al. (1989) *J. Virol.* 63:631–638.

For convenience, plasmids are available that provide the necessary portions of adenovirus. Plasmid pXC.1 (McKinnon (1982) *Gene* 19:33–42) contains the wild-type left-hand end of Ad5, from Adenovirus 5 nt 22 to 5790. pBHG10 (Bett. et al. (1994) *Proc. Natl. Acad Sci. USA* 91:8802–8806; Microbix Biosystems Inc., Toronto) provides the right-hand end of Ad5, with a deletion in E3. The deletion in E3 provides room in the virus to insert a 3-kb PB-TRE without deleting the endogenous enhancer-promoter. The gene for E3 is located on the opposite strand from E4 (r-strand). pBHG11 [Bett. et al. (1994)] provides an even larger E3 deletion (an additional 0.3 kb is deleted).

For manipulation of the early genes, the transcription start site of Ad5 E1A is at nt 498 and the ATG start site of the E1A coding segment is at nt 560 in the virus genome. This region can be used for insertion of a PB-TRE. A restriction site may be introduced by employing polymerase chain reaction (PCR), where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a 30 sequence change resulting in a unique restriction site, one can provide for insertion of PB-TRE at that site. Example 1 provides a more detailed description of an adenoviral vector in which E1A is under PB-TRE control.

A similar strategy may be used for insertion of a PB-TRE to regulate E1B. The E1B promoter of Ad5 consists of a single high-affinity recognition site for SpI and a TATA box. This region extends from Ad5 nt 1636 to 1701. By insertion of a PB-TRE in this region, one can provide for cell-specific transcription of the E1B gene. By employing the left-hand region modified with the cell-specific response element regulating E1A. as the template for introducing a PB-TRE to regulate E1B. the resulting adenovirus vector will be dependent upon the cell-specific transcription factors for expression of both E1A and E1B. Example 1 provides a more detailed description of how such constructs can be prepared.

Similarly, a PB-TRE may be inserted upstream of the E2 gene to make its expression cell-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Micro. and Imm.* (1 995) 199 part 3:177–194.

The E2 late promoter overlaps with the coding sequences of a gene encoded by the counterstrand and is therefore not amenable to genetic manipulation. However, the E2 early promoter overlaps only for a few base pairs with sequences coding for a 33-kDa protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor binding sites E2F and ATF. Therefore, insertion of a PB-TRE having SpeI ends into the SpeI site in the 1-strand would disrupt the endogenous E2 early promoter of Ad5 and should allow AR-restricted expression of E2 transcripts.

For E4, one must use the right hand portion of the adenovirus genome. The E4 transcription start site is predominantly at about nt 35609, the TATA box at about nt 35638 and the first AUG/CUG of ORF1 is at about nt 35532. Virtanen et al. (1984) *J. Virol.* 51: 822–831. Using any of the above strategies for the other genes, a PB-TRE may be introduced upstream from the transcription start site. For the construction of a full-length adenovirus with a PB-TRE inserted in the E4 region, the co-transfection and homologous recombination are performed in W162 cells (Weinberg et al. (1983) *Proc. Anatl. Acad. Sci.* 80:5383–5386) which provide E4 proteins in trans to complement defects in synthesis of these proteins.

Methods of packaging adenovirus poly,nucleotides into adenovirus particles are known in the art and are described in the Examples.

Methods Using the Adenovirus Vectors of the Invention

The subject vectors can be used for a wide variety of purposes, which will vary with the desired or intended result. Accordingly, the present invention includes methods using the adenoviral vectors described above.

In one embodiment, methods are provided for conferring selective cytotoxicity in cells which allow a PB-TRE to function, such as cells expressing androgen receptor comprising contacting the cells with an adenovirus vector described herein. Cytotoxicity can be measured using standard assays in the art, such as dye exclusion, $^3$H-thymidine incorporation, and/or lysis.

In another embodiment, methods are provided for propagating an adenovirus specific for cells that allow a PB-TRE to function, such as those cells expressing androgen receptor. These methods entail combining an adenovirus vector with cells whereby said adenovirus is propagated.

Another embodiment provides methods of killing cells that allow a PB-TRE to function, such as cells expressing the androgen receptor in a mixture of cells, comprising combining the mixture of cells with an adenovirus vector of the present invention. The mixture of cells is generally a mixture of normal cells and cancerous cells producing androgen receptor, and can be an in vivo mixture or in vitro mixture.

The invention also includes methods for detecting cells which allow a PB-TRE to function, such as cells expressing androgen receptor in a biological sample. These methods are particularly useful for monitoring the clinical and/or physiological condition of an individual (i.e., mammal), whether in an experimental or clinical setting. In one method, cells of a biological sample are contacted with an adenovirus vector, and replication of the adenoviral vector is detected. Alternatively, the sample can be contacted with an adenovirus in which a reporter gene is under control of a PB-TRE. Expression of the reporter gene indicates the presence of cells that allow the PB-TRE to function, such as androgen receptor-producing cells. Alternatively, an adenovirus can be constructed in which a gene conditionally required for cell survival is placed under control of a PB-TRE. This gene may encode, for example, antibiotic resistance. The adenovirus is introduced into the biological sample, and later the sample is treated with an antibiotic. The presence of surviving cells expressing antibiotic resistance indicates the presence of cells that allow a PB-TRE to function. A suitable biological sample is one in which androgen receptor-producing cells may be or are suspected to be present. Generally, in mammals, a suitable clinical sample is one in which cancerous cells producing androgen receptor, such as prostate cancer cells, are suspected to be present. Such cells can be obtained, for example, by needle biopsy or other surgical procedure. Cells to be contacted may be treated to promote assay conditions such as selective enrichment and/or solubilization. In these methods, androgen receptor-producing cells can be detected using in vitro assays that detect proliferation, which are standard in the art. Examples of such standard assays include, but are not limited to, burst assays (which measure virus yields) and plaque assays (which measure infectious particles per cell). Also, propagation can be detected by measuring specific adenoviral DNA replication, which are also standard assays.

The invention also provides methods of modifying the genotype of a target cell, comprising contacting the target cell with an adenovirus vector described herein, wherein the adenoviral vector enters the cell.

The invention also provides methods of modifying the genotype of a target cell, comprising contacting the target cell with an adenovirus vector described herein, wherein the adenoviral vector enters the cell.

The invention further provides methods of suppressing tumor cell growth, preferably a tumor cell that expresses androgen receptor, comprising contacting a tumor cell with an adenoviral vector of the invention such that the adenoviral vector enters the tumor cell and exhibits selective cytotoxicity for the tumor cell. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and stopping tumor growth, as well as tumor shrinkage. "Suppressing" tumor growth indicates a growth state that is curtailed when compared to growth without contact with, i.e., transfection by, an adenoviral vector described herein.

The invention also provides methods of lowering the levels of a tumor cell marker in an individual, comprising administering to the individual an adenoviral vector of the present invention, wherein the adenoviral vector is selectively cytotoxic toward cells producing the tumor cell marker. Tumor cell markers include, but are not limited to, PSA, hK2, and carcinoembryonic antigen. Methods of measuring the levels of a tumor cell marker are known to those of ordinary skill in the art and include, but are not limited to, immunological assays, such as enzyme-linked immunosorbent assay (ELISA), using antibodies specific for the tumor cell marker. In general, a biological sample is obtained from the individual to be tested, and a suitable assay, such as an ELISA, is performed on the biological sample.

The invention also provides methods of treatment, in which an effective amount of an adenoviral vector(s) described herein is administered to an individual. Treatment using an adenoviral vector(s) is indicated in individuals with prostate-associated diseases as described above, such as hyperplasia and cancer. Also indicated are individuals who are considered to be at risk for developing prostate-associated diseases, such as those who have had disease which has been resected and those who have had a family history of prostate-associated diseases. Determination of suitability of administering adenoviral vector(s) of the invention will depend, inter alia, on assessable clinical parameters such as serological indications and histological examination of tissue biopsies. Generally, a pharmaceutical composition comprising an adenoviral vector(s) in a pharmaceutically acceptable excipient is administered. Pharmaceutical compositions are described above.

The amount of adenoviral vector(s)to be administered will depend on several factors, such as route of administration, the condition of the individual, the degree of aggressiveness of the disease, the particular PB-TRE employed, and the particular vector construct (i.e., which adenovirus gene(s) is under PB-TRE control).

If administered as a packaged adenovirus, from about $10^4$ to about $10^{14}$, preferably from about $10^4$ to about $10^{12}$, more preferably from about $10^4$ to about $10^{10}$. If administered as a polynucleotide construct (i.e., not packaged as a virus), about 0.01 μg to about 100 μg can be administered, preferably 0.1 μg to about 500 μg, more preferably about 0.5 μg to about 200 μg. More than one adenoviral vector can be administered, either simultaneously or sequentially. Administrations are typically given periodically, while monitoring any response. Administration can be given, for example, intratumorally, intravenously or intraperitoneally.

The adenoviral vectors of the invention can be used aloneor in conjunction with other active agents, such as chemotherapeutics, that promote the desired objective.

The following examples are provided to illustrate but not limit the invention.

EXAMPLES

Example 1

Adenovirus Vectors Containing an Early Gene Under Control of a Transcriptional Element Derived from a Probasin Transcriptional Response Element (PB-TRE)

1. A. The probasin Transcriptional Response Element (PB-TRE)

The 454 nucleotide fragment (nt about −426 to about +28) of the rat PB-TRE, which contains two androgen response elements (ARE sites), a CAAT box and a TATAA box (FIG. 1, SEQ ID NO:1), was amplified by polymerase chain reaction (PCR) using rat genomic DNA as template and the synthetic oligonucleotides:

42.2.1 (SEQ ID NO:4):

5-GATCACCGGTAAGCTTCCACAAGTGCATTTAG CC-3',

PinAI site underlined, and 42.2.2 (SEQ ID NO:5):

5'-GATCACCGGTCTGTAGGTATCTGGACCTCACT G-3', or oligonucleotides 42.2.3 (SEQ ID NO:6):

5'-GATCCGGCCGAAGCTTCCACAAGTGCATTTAG CC-3',

EagI site underlined, and 42.2.4 (SEQ ID NO:7):

5'-GATCCGGCCGCTGTAGGTATCTGGACCTCA CTG-3'. The oligonucleotides created a unique PinAI (AgeI) site (A/CCGGT) or Eagl site (C/GGCCG) at both ends of the PCR fragments. The PCR fragments were ligated into the pGEM-T vector (Promega) to generate plasmids CN249, and CN250. Similarly, CN256 was created using the same strategy but the PB-TRE fragment was ligated into the pCRT vector (Invitrogen); CN271 is identical to CN250 but with a HindIII site at the 5'-end. These plasmids provide the PB-TRE DNA fragments for the constructs reported below. In some of the adenovirus vectors described below, the endogenous (adenoviral) TREs were not deleted; rather, in each construct, the PB-TRE was inserted between the endogenous TRE (e.g., the E1A TRE) and its respective coding segment (e.g., the E1A coding segment). In other vectors, the endogenous (Ad5) promoter-enhancer has been deleted, and the prostate-specific promoter-enhancer placed immediately upstream of an early gene.

1. B. Construction of PB-TRE Adenovirus Comprising an Adenovirus Gene Under Control of a Prostate-specific Transcriptional Regulatory Element 1. B. 1. PB-TRE-driven E1A Ad5 plasmid (CN251)

An adenovirus vector in which expression of an early gene, E1A, is under control of PB-TRE was constructed as follows.

CN 124 is a derivative of construct pXC.1, which contains the wild-type left-hand end of Ad5, from nt 22 to 5790, including. both E1A and E1B (McKinnon (1982) *Gene* 19:33–42). CN124 also has, among other alterations, an artificial PinAI site at Ad5 nt 547 (between the E1A transcriptional start at nt 498 and the E1A coding segment beginning with ATG at 560).

To construct CN 124 from pXC.1, we introduced an AgeI site 12 bp 5' to the E1A initiation codon (Ad5 547) by oligonucleotide-directed mutagenesis and linked PCR. To achieve this, pXC.1 was PCR-amplified using primers:

5'-TCGTCTTCAAGAATTCTCA (15.133A) (SEQ ID NO:8), containing an EcoRI site, and

5'-TTTCAGTCACCGGTGTCGGA (15.134B) (SEQ ID NO:9), containing an extra A to introduce an AgeI site. This created a segment from the EcoRI site in the pBR322 backbone to Ad5 560. A second segment of pXC.1 from Ad 541 to the XbaI site at Ad nucleotide 1339 was amplified using primers:

5'-GCATTCTCTAGACACAGGTG (15.133B) (SEQ ID NO:10) containing an XbaI site, and

5'-TCCGACACCGGTGACTGAAA (15.134A) (SEQ ID NO:11), containing an extra T to introduce an AgeI site. These two PCR-amplified DNA segments were mixed and amplified with primers 15.133A and 15.133B to create a DNA segment from the EcoRI site to the XbaI site of pXC.1. This DNA segment encompasses the leftmost 1317 bases of Ad sequence and contains an AgeI site at Ad 547. This DNA segment was used to replace the corresponding segment of pXC.1 to create CN95.

An EagI site was created upstream of the E1B start site by inserting a G residue at Ad5 1682 by oligonucleotide directed mutagenesis as above. To simplify insertion of an PB-TRE in the EagI site, the endogenous EagI site in CN95 was removed by digestion with EagI, treatment with mung bean nuclease, and re-ligation to construct CN114. The primers:

5 -TCGTCTTCAAGAATTCTCA (15.133A) (SEQ ID NO:8), containing an EcoRI site, and

5'-GCCCACGGCCGCATTATATAC (9.4) (SEQ ID NO:12), containing an EagI site, and

5'-GTATATAATGCGGCCGTGGGC (9.3) (SEQ ID NO:13) containing an extra G and an EagI site, and 5'-CCAGAAAATCCAGCAGGTACC (24.020) (SEQ ID NO:14), containing a KpnI site, were used to amplify the segment between 1682 and the KpnI site at Ad5 2048. Co-amplification of the two segments with primers 15.133A and 24.020 yielded a fragment with an EagI site at Ad5 1682 which was used to replace the corresponding EcoRI/KpnI site in pXC.1 to construct CN124.

CN124 was linearized with PinAI and dephosphorylated with calf intestinal alkaline phosphatase (New England Biolabs). CN249 was digested with PinAI to free the PB-TRE fragment. The PB-TRE fragment was then ligated into the PinAI-linearized CN124, producing CN251. CN253 is similar to CN251 except for the PB-TRE fragment is in the reverse orientation.

Thus, construct CN251 contains the PB-TRE inserted upstream of and operably linked to the E1A coding segment in the Adenovirus 5 genome. The vector CN253 is similar, but the PB-TRE is in the reverse orientation.

1. B. 2. PB-TRE-driven E1B Ad5 plasmid (CN254)

An adenovirus derivative in which the expression of another early gene, E1B, is under control of the PB-TRE was constructed as follows.

CN 124, which carries the left-end of Ad5, as described above, also contains an artificial EagI site at Ad5 nt 1682, or just upstream of the E1B coding segment. The PB-TRE fragment was excised from CN250 with EagI and inserted into CN124 digested with EagI. This produced CN254, which contains the PB-TRE immediately upstream of and operably linked to the E1B coding segment.

CN255 is identical to CN254, but the orientation of the PB-TRE insert is reversed.

CN275 is the same as CN254, but with a HindIII site at the 5'-end.

1. C. Construction of Adenovirus Vectors in which Expression of One Adenovirus Replication Gene is Controlled by PB-TRE, and Expression of Another is Controlled by Another Prostate-specific TRE 1 C. 1. Adenovirus vector comprising PB-TRE-driven E1A and E1B driven by another promoter-enhancer, PSA-TRE (CN257)

An adenovirus vector in which expression of the E1A gene is under control of the PB-TRE and expression of the E1B gene is under control of the prostate specific antigen transcriptional regulatory element (PSA-TRE) was constructed as follows. The PSA-TRE region has been described in detail in, inter alia, U.S. Pat. Nos. 5,648,478 and 5,698,443; Lundwall (1989) *Biochem. Biophys. Res. Commun.* 161:1151–1159; and Zhang et al. (1997) *Nucleic Acids Res.* 25:3143–50.

CN 125 is an (left-end) adenovirus derivative in which expression of the E1B gene is driven by a PSA-TRE, and in which an PinAI site lies upstream of the E1A gene, whose expression is driven by its wild-type (endogenous) promoter. CN125 was derived by inserting the PSA-TRE as an EagI fragment from CN105 into the EagI site of CN124 (immediately upstream of the E1B gene).

The PinAI PB-TRE fragment was then inserted into CN125 digested with PinAI, which cleaves just upstream of E1A. This created construct CN257, which is a plasmid containing PB-TRE-driven E1A and PSA-TRE-driven E1B. CN258 is similar to CN257, but with the opposite orientation of the PB-TRE fragment.

1. C.2. Ad5 plasmid comprising PSA-TRE-driven E1A and PB-TRE-driven E1B (CN273)

An adenovirus vector was constructed in which expression of E1A is mediated by the exogenous non-PSA-TRE promoter-enhancer, and expression of E1B is mediated by PB-TRE.

The construct CN257, which is a plasmid containing PB-TRE-driven E1A and PSA-TRE-driven E1B, was described above.

CN273 was constructed with a position change between PSA-TRE and PB-TRE in CN257. CN143 is a pBluescript (Stratagene, La Jolla, Calif.) derivative containing the PSA-TRE fragment. This fragment was excised with PinAI and ligated into PinAI-digested CN254. The final construct is a plasmid containing PSA-TRE-driven E1A and PB-TRE-driven E1B. CN274 is similar to CN273 except for the opposite orientation of PB-TRE.

1. D. Construction of Adenovirus Vectors in which Expression of More than One Adenovirus Replication Gene is Controlled by a PB-TRE 1. D. 1. PB-TRE-driven E1A and PB-TRE-driven E1B Ad5 plasmid (CN268)

An adenovirus vector in which expression of both E1A and E1B are driven by PB-TRE was constructed as follows.

CN251, described above, comprises a PB-TRE fragment inserted just upstream of the E1A coding segment.

CN268 was generated by inserting a second PB-TRE in front of the E1B gene in CN251. A PB-TRE fragment was excised from CN250 by EagI-digestion and ligated into EagI-digested CN251 to create CN268. The final construct is a plasmid with PB-TRE driving E1A and a second PB-TRE driving E1B. CN269 is the same as CN268 but the orientation of the second PB-TRE is reversed.

In addition, in experiments (described below) in which adenoviral vectors were constructed in which two genes were under control of two separate TREs specific for prostate cells, the effect was synergistic (i.e. the increase in cell-specificity of transcription is more than additive).

1. E. Construction of Adenovirus Vectors in which Expression of Reporter Genes is Under Control of a Prostate-specific TRE 1. E. 1. PB-TRE-driven reporter gene plasmid (CN280, CN2.81)

An adenovirus vector containing the entire structural gene of firefly luciferase (luc) driven by a PB-TRE was constructed as follows.

CN280 was derived from pGL3-Basic (Promega) for transfection experiments. A PB-TRE fragment was excised from CN249 by NcoI/SacI digestion and ligated into NcoI/SacI-digested pGL3-Basic to produce CN280. The final construct is a plasmid containing the entire structural gene of luc driven by PB-TRE.

CN28 1 was generated from the same procedure except that a PB-TRE fragment was ligated into pGL3-Enhancer (Promega).

1. E. 2. AR up-regulation of PB-TRE-driven reporter gene expression

To test the specificity of PB-TRE-driven gene expression. the region of the PB 5'-flanking DNA (about −426 to about +28) including the endogenous promoter sequences was inserted upstream of the firefly luciferase gene to generate a chimeric PB-TRE-luc plasmid (CN280) (see above). Transient transfection of LNCaP (PSA-producing and AR-producing prostate carcinoma cells) and PC-3 (PSA-deficient and AR-deficient prostate carcinoma cells) cells was performed. Transfection involved the cationic lipid-mediated method under conditions standardized for another vector, pCMV-βgal. The results presented in FIG. 3 show that LNCaP cells transfected with CN280 have approximately 400 times more activity than background, indicating that the PB-TRE is intact. Further, the overall luciferase activity recovered in the cellular extracts of LNCaP cells was much higher (about 30–40-fold) than that measured in PC-3 cells. Thus, the results indicate that PB-TRE expression is up-regulated regulated in AR-producing. PSA-producing cells, and that PB-TRE is capable of mediating specific expression in cells producing the androgen receptor.

1. F. Homologous Recombination for Generation of the Recombinant Adenovirus Vectors Containing a PB-TRE Of the plasmids described above, in which an adenovirus gene is under control of a prostate-specific TRE, man) contained only the left-end of adenovirus. In order to construct whole adenovirus comprising adenovirus gene(s) under control of prostate-specific TREs. these plasmids were homologously recombined with right-end adenovirus plasmids.

A human embryonic kidney cell line, 293, efficiently expresses the Ad5 E1A and E1B genes and exhibits a high transfection efficiency with adenovirus DNA. For these experiments, 293 cells were co-transfected with one left-end Ad5 plasmid and one right-end Ad5 plasmid. Homologous recombination generates whole PB-TRE-containing adenoviruses with the required genetic elements for replication in 293 cells. Briefly, 5 μg of CN251 (PB-TRE -E1A) and BHG11 (which contains cat right part of adenovirus) were co-transfected into 293 cells. The cells were overlaid with medium, and infectious virus, generated by in vivo recombination, was detected by cytopathic effect and isolated. Plaque-purified stocks of a vector comprising a PB-TRE, designated CN737, were established. The structure of the recombinant virus was characterized by PCR. restriction endonuclease digestion and Southern blot analysis. The viral genome of CN737 is the full-length Ad5 wherein E1A is under a control of PB-TRE.

The plasmids to be combined were co-transfected into 293 cells using cationic liposomes such as Lipofectin (DOTMA:DOPE™, Life Technologies). The two plasmids (10 μg of each in 500 μl of minimum essential medium (MEM) without serum or other additives) ere mixed with a four-fold molar excess of liposomes in 200 μl of the same buffer. The DNA-lipid complexes were then placed on the cells and incubated at 37° C., 5% $CO_2$ for 16 hours. After incubation the medium was hanged to MEM with 10% fetal bovine serum and the cells are further incubated at 37° C., 5% $CO_2$, for 10 days with two changes of medium. At the end of this time the cells and medium were transferred to tubes, freeze-thawed three times, and the lysate was used to infect 293 cells at the proper dilution to detect individual viruses as plaques.

Plaques obtained were plaque-purified twice, and viruses were characterized for presence of desired sequences by PCR and occasionally by DNA sequencing. For further experimentation, the viruses were purified on a large scale by cesium chloride gradient centrifugation.

Additional viruses containing the entire adenovirus genome with one or more early genes under control of a prostate-specific TRE were also constructed. Viruses CN738, CN739 and CN740 were generated with the same approach except that the CN251 (PB-TRE-E1A) plasmid was replaced with CN254 (PB-TRE-E1B), CN257 (PB-TRE-E1A, PSA-TRE-E1B), and CN273 (PSA-TRE-E1A, PB-TRE-E1B), respectively. In each of these viruses, the prostate-specific TRE (PB-TRE or PSA-TRE) was inserted between the appropriate coding segment (e.g., E1A or E1B) and its corresponding endogenous promoter. These viruses were therefore constructed by engineering one or two identical copies of the rat PB-TRE upstream of one or two essential adenovirus 5 early genes, E1A and E1B.

In short, CN737 is an adenovirus type 5 which contains one PB-TRE upstream of the E1A gene; CN738, PB-TRE upstream of E1B; and CN740, two identical copies of PB-TRE upstream of the E1A and E1B.

Example 2

Testing a Putative PB-TRE

Plasmids similar to a reporter plasmid, such as CN280 described above, may be used to test the prostate-specificity of putative prostate-specific TREs (PS-TREs) or PS-TRE variants such as PB-TRE variants. The PS-TRE to be tested may have mutations such as deletions or insertions between binding sites known to be important in PS-TRE activity (e.g., are sites, etc.) or base substitutions in these sites themselves. For example, some variants in the AREs (androgen receptor binding sites) of PB-TREs are known and described above and in the literature. Rennie et al. (1993) *Mol. Endocrinol.* 7:23–36. Additional variant PB-TREs may comprise, for example, mutation(s) between a PB-TRE promoter and a PB-TRE enhancer (including deletions, substitutions and additions); a combination of a non-prostate specific promoter and a PB-TRE enhancer; a combination of a non-prostate-specific promoter and a PSA-TRE enhancer; the rearrangement of segments of the enhancer and promoter of a prostate-specific TRE; or any other variant of a PB-TRE.

Briefly, the putative prostate-specific TRE or TRE variant such as a putative PB-TRE is inserted upstream of a reporter gene (exemplified by, but not limited to, firefly luciferase, luc). Reporter genes have been disclosed above, and methods for such construction are known in the art or are disclosed herein.

A comparison of reporter gene activity in prostate cells (or cells expressing prostate gene products) and non-prostate cells, using as a control an adenovirus with a non-cell-specific-promoter (e.g. CMV) controlling reporter gene expression, can indicate the efficacy of a putative PS-TRE in mediating prostate cell-specific gene expression.

Example 3

Testing the Cytotoxic Ability of Adenovirus Vectors on Prostate Carcinoma Cells and Tumor Xenografts 3. A. Experimental Strategy An especially useful objective in the development of prostate-specific adenoviral vectors is to treat patients with prostate carcinoma. The strategy is to develop a prostate tissue-specific targeting pharmaceutical which could selectively kill a certain type of tumor cells (such as prostatic neoplasia) while leaving their non-cancerous neighbors unharmed. A 'smart bomb' virus, in which key gene expression is restricted by a tissue-specific regulator) element incorporated into its chromosome. meets this requirement. As stated previously, PB gene expression is exclusively in the prostate and is transcriptionally regulated by androgens. It has also been demonstrated that the minimal 454 nucleotides of PB-TRE is sufficient to target and restrict gene expression to prostate cells. This arrangement limits the expression of important early viral genes to prostatic cells. The E1 coding segment, for example, can placed under the control of PB-TRE; the TRE will remain silent in non-prostatic cell types and, consequently, prevent early gene expression, viral replication and cell lysis. Several experiments have contributed to the understanding of PB-TRE-containing adenoviruses CN737, CN738 and CN740, described above.

An initial indicator of the feasibility is to test the vectors using a technique known in the art, such as testing the vectors for cytotoxicity against prostate and non-prostate cells in vitro (cytopathic effects), plaque assays, and tests against prostate carcinoma cells such as prostate xenografts grown subcutaneously in Balb/c nu/nu mice.

3. B. Int Vitro Cytopathic Effects of Adenovirus with Adenoviral Early Gene(s) Under Control of Prostate-specific TRE(s)

The first task at hand was to characterize the differential viral replication and cytopathic effects (CPE).

The adenovirus used included CN702 (full-length Ad5 with unaltered E1 region); CN737 (full-length Ad5 with E1A under control of PB-TRE; see Example 1) and CN740 (full-length Ad5 with both E1A and E1B under control of copies of PB-TRE; see Example 1).

CPE assays were performed as follows: Cells were infected with virus at increasing multiplicities of infection (MOI) and monitored for cytopathic effect. Ovarian carcinoma cells (OVCAR-3) and the human prostate cancer cells (LNCaP) each underwent complete monolayer cytolysis with wild-type adenovirus CN702 at MOI as low as 0.01 within 7 to 10 days. This indicated that wild-type adenovirus infects both prostatic and non-prostatic cells. In contrast, CN737 (PB-TRE-E1A) or CN740 (PB-TRE-E1A, PB-TRE-E1B)-infected LNCaP cells showed significant cytopathic effects at the same time points with MOI of 0.1 or 0.01. CN737 or CN740-infected OVCAR-3 cell monolayers did not show visible cytopathic effects with the same MOI.

Thus, adenoviruses in which one or two early Ad5 genes were under control of probasin TREs were able to mediate replication and cytopathic effects specifically in prostate cells, but not in non-prostate cells.

3. C. Plaque Assay of Adenovirus with Adenovirus Gene(s) Under Control of Prostate-specific TRE(s)

The prostate-cell specificity of adenovirus viruses with adenovirus under control of prostate-specific TRE(s) was quantified. One method used to test this was a plaque assay. A plaque assay is an infectious assay that quantifies how efficiently a particular virus produces a productive infection in a cell line. Plaquing efficiency was evaluated in the following cell types: prostate cells (LNCaP) and non-prostate cells (MCF-7, BHL-100, OVCAR-3, and 293).

The plaque assay was performed as following: Confluent cell monolayers seeded in 6-well dishes eighteen hours before infection were infected with 10-fold serial dilutions of CN737, CN738, CN740, and CN702. After infecting monolayers for four hours in serum-free media (MEM), the media was removed and replaced with a solution of 0.75% low melting point agarose and tissue culture media. Plaques were scored two weeks after infection.

TABLE 1

PB-TRE engineered adenovirus plaque assay

| Cell Line | Virus | Ave Titre | Titre/293 | CN7--/CN702 |
|---|---|---|---|---|
| 293 | CN702 (wt) | 1.30E + 06 | 1.0 | |
| | CN737 | 3.40E + 05 | 1.0 | |
| | CN738 | 5.60E + 05 | 1.0 | |
| | CN740 | 4.80E + 06 | 1.0 | |
| LNCaP | CN702 | 1.40E + 06 | 1.08 | 1.0 |
| | CN737 | 1.90E + 05 | 0.56 | 0.52 |
| | CN738 | 4.00E + 05 | 0.71 | 0.66 |
| | CN740 | 1.50E + 06 | 0.31 | 0.29 |
| PC-3 | CN702 | 1.80E + 05 | 0.14 | 1.0 |
| | CN737 | 1.10E + 04 | 0.032 | 0.23 |
| | CN738 | 5.00E + 04 | 0.089 | 0.64 |
| | CN740 | 4.50E + 04 | 0.011 | 0.079 |
| MCF-7 | CN702 | 3.40E + 05 | 0.26 | 1.0 |
| | CN737 | 3.90E + 02 | 0.0012 | 0.0046 |
| | CN738 | 2.20E + 04 | 0.065 | 0.25 |
| | CN740 | 3.90E + 03 | 0.00083 | 0.0032 |
| HBL-100 | CN702 | 2.00E + 05 | 0.15 | 1.0 |
| | CN737 | 1.40E + 02 | 0.00041 | 0.0027 |
| | CN738 | 8.60E + 03 | 0.0150 | 0.1 |
| | CN740 | 5.30E + 01 | 0.000011 | 0.000073 |
| OVCAR-3 | CN702 | 4.10E + 05 | 0.32 | 1.0 |
| | CN737 | 1.40E + 02 | 0.00041 | 0.0013 |
| | CN738 | 1.40E + 03 | 0.0025 | 0.0078 |
| | CN740 | 1.20E + 03 | 0.00025 | 0.00078 |

Table 1 shows the average titer of duplicate samples for the viruses tested. The titer for a particular virus in all cell lines was normalized to its titer on 293 cells. This allows comparisons between viruses in a particular cell type. Once the titers on a cell type were normalized to 293 cells, the normalized numbers of the recombinant viruses were compared to CN702. A ratio of less than one suggests that the virus tested plaques less efficiently than CN702. Conversely, a ratio greater than one suggests that the virus plaques more efficiently than CN702.

Several interesting observations can be made from the plaque assay. First and most importantly, PB-TRE-engineered adenoviruses demonstrated preferential replication in prostate tumor cell line LNCaP compared to non-prostate cells. Since this carcinoma expresses androgen receptor and PSA. the PB regulatory region installed in the adenovirus vectors should be active in promoting the transcription of adenoviral early genes. The data suggests that this is the case, and the adenovirus comprising a PB-TRE induced cytopathic effects with an efficiency comparable to that of wild-type adenovirus in prostate tumor cells. Second, PB-TRE-driven adenoviruses show very little virus-mediated cytolysis of non-prostate tumor cells. The plaquing efficiency) for three of the adenovirus vectors comprising a PB-TRE decreases dramatically in the non-prostate cell lines included in the experiment. Thus, PB-TRE engineered virus mediated cytolysis is significantly decreased relative to wild-type adenovirus in non-prostate cells.

Third, the vector CN740, in which two adenovirus replication genes (E1A and E1B) are controlled by separate PB-TREs, demonstrated unexpectedly better specificity than adenoviruses in which only one adenovirus gene was controlled by a PB-TRE. For example, in the AR-deficient cell line PC-3, CN737, in which a PB-TRE controls expression of E1A, showed a 4-fold increase in replication specificity compared to CN702 (wt). CN738, in which PB-TRE controls expression of E1B, showed little increase in specificity. However, CN740, in which PB-TREs control transcription of both E1A and E1B demonstrated a 13-fold increase in replication specificity, which is more than additive. Similar synergy was demonstrated with the AR-deficient cell line HBL-100. In this line, CN737 showed a 370-fold increase in specificity, and CN738, 10-fold. However, CN740 demonstrated a 14,000-fold increase in replication specificity. Therefore, the addition of a second prostate-specific TRE controlling an adenovirus replication gene results in a more than additive effect and an unexpectedly better increase in the cell-specific replication.

While all three vectors comprising a PB-TRE, CN737, CN738 and CN740 showed prostate-specific replication compared to At CN702, CN737 and CN740 showed greater specificity than CN738 (PB-TRE - E1B).

In addition, in the prostate cell line, the PB-TRE-containing adenoviruses replicated slightly less well than wt CN702. For example, CN737 produced a titer of 0.56 relative to that of CN702. However. this reflects a small drop (up to 2- or 3-fold) in replication in prostate cells simultaneously obtained with a very large increase (up to 1.200-fold) in specificity.

In short. the PB-TRE adenoviruses described above demonstrated an ability to replicate specifically in prostate cells expressing androgen receptor.

3. D. Testing the Efficacy Against Xenografts of Adenovirus Comprising an Adenovirus Gene Under Control of a Prostate-specific TRE Mice are given subcutaneous injections with 1×10$^7$ prostate carcinoma cells. such as LNCaP, in PBS. Tumor cells can be tested for probasin activity by assaying for probasin in serum using standard assays (for example, ELISA).

For this experiment, test virus vectors are introduced into the mice either by direct intratumoral, intravenous or intraperitoneal injection of approximately 10$^8$ pfu of virus (if administered as a packaged virus) in 0.1 ml PBS +10% glycerol or intravenously via the tail vein. If administered as a polynucleotide construct (i.e., not packaged in virus), 0.1 μg to 100 μg or more can be administered. Tumor sizes are measured and, in some experiments, blood samples are taken weekly. The effect of intratumoral injection of an adenovirus vector of the present invention on tumor size and serum androgen receptor levels is compared to sham treatment.

While it is likely that a therapeutic based on the viruses described here would be given intralesionally (i.e., direct injection), it would also be desirable to determine if intravenous (IV) administration of the virus can affect tumor growth. If so, then it is conceivable that the virus could be used to treat metastatic tumor deposits inaccessible to direct injection. For this experiment, groups of five mice bearing prostate cancer tumors are inoculated with 10$^8$ pfu of an adenoviral vector of the present invention by tail vein injection, or 10$^8$ pfu of a replication defective adenovirus (CMV-LacZ) to control for non-specific toxic effects of the virus, or with buffer used to carry the virus. The effect of IV injection of the adenoviral vector on tumor size is compared to the sham treatment. As shown in Example 5. F., the modified adenovirus of the present invention was capable of specifically eradicating prostate cell carcinoma induced in subject mice.

Example 4

Construction of an Adenoviral Vector Containing the Coding Region for the Adenovirus Death Protein (ADP) Under Control of a Prostate-specific TRE An adenovirus vector in which the adenovirus death protein (ADP) was placed under control of a PB-TRE can be constructed as described below. ADP is encoded within the E3 region and naturally under control of the major late promoter (MLP). The gene appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/or a lower dosage requirement.

In an AR-specific viral vector (such as those described above in Example 1), a deletion can be created in the E3 region to accommodate a PB-TRE. The ADP coding sequence from Ad2 can be reintroduced into the E3 region of adenovirus Ad5 as follows:

An ADP cassette is constructed using overlap PCR. The Y leader, an important sequence for correct expression of some late genes, is PCR-amplified using primers:

5' GCCTTAATTAAAAGCAAACCTCACCTCCG . . . Ad2 28287bp (37.124.1) SEQ ID NO:15); and 5' GTGGAACAAAAGGTGATTAAAAAATCCCAG . . . Ad2 28622bp (37.146.1) (SEQ ID NO:16).

The ADP coding region is PCR amplified using primers

5' CACCTTTTGTTCCACCGCTCTGCTTATTAC . . . Ad2 29195bp (37.124.3) (SEQ ID NO:17) and 5' GGCTTAATTAACTGTGAAAGGTGGGAGC . . . Ad2 29872bp (37:124.4) (SEQ ID NO:18).

The two fragments were annealed and the overlap product was PCR amplified using primers 37.124.1 and 37.124.4. The ends of the product were polished with Klenow fragment and ligated to BamHI cut pGEM-72 (+) (CN241; Promega, Madison. Wis.). The ADP cassette was excised by digesting CN241 with PacI restriction endonuclease and ligated with two vectors, CN247 and CN248, generating plasmids CN252 and CN270, respectively. CN247 contains a unique PacI site in the E3 region and was constructed as follows. A plasmid containing the full length Ad5 genome, TG3602 (Transgene, France), was digested with BamHI and religated to yield CN221. The backbone of this plasmid (outside of the adenovirus sequence) contained a PacI site that needed to be removed to enable further manipulations. This was effected by digesting CN221 with PacI and polishing the ends with T4 DNA polymerase, resulting in CN246. CN246 was digested with AscI and AvrII (to remove intact E3 region). This fragment was replaced by a similarly cut fragment derived from BHG11. The resulting plasmid, CN247, lacks the E3 region and a PacI site suitable for insertion of the ADP cassette fragment (described above). Ligation of CN247 with the ADP cassette generated CN252.

CN248 (a construct that would allow introduction of an ADP cassette into a Ad that also contains a deletion/ substitution in the E4 region) was made as follows. The E4 region was deleted by digesting CN108, a construct that contains right hand end Ad5 sequence from the unique EcoRI site in the E3 region, with AvrII and AflIII. The only E4 ORF necessary for viral replication, ORF 6. was reintroduced by PCR amplifying the ORF with primers, 33.81.1 (Ad5 33096):

GCAGCTCACTTAAGTTCATGTCG (SEQ ID NO:19)
33.81.2 (Ad5 34084):

TCAGCCTAGGAAATATGACTACGTCCG (SEQ ID NO:20)

The resulting plasmid is CN203. CN203 was digested with EcoRI and ligated to CN209, a shuttle plasmid, to generate CN208. In the final cloning step, CN208 was digested with AscI and AvrII and ligated to similarly cut E4 deletion/substitution with the ADP cassette.

Thus, both CN252 and CN270 are adenoviral vectors containing the ADP gene and lacking the E3 gene. In addition, CN270 lacks some sequence in the E4 region as previously described. Full-length adenoviral vectors are obtained via in vitro ligation of (1) appropriately prepared vial DNA digested with BamHI and (2) CN252 or CN257 also digested with BamHI. The ligation product is used to transfect 293 cells. Plaque assays are performed as described in Example 1.

CN252 and CN270 can also be modified by insertion of a PB-TRE to place the ADP gene under transcriptional control of PB-TRE.

Example 5

Additional Analysis of Adenoviruses in which Adenovirus Genes are Under Control of Prostate-specific TREs 5. A. Adenoviral Vectors In each of adenoviruses CN739 and CN753, two viral genes were under control of two separate prostate-specific TREs. These viruses were shown, as described below, to possess a stable genome; exhibit higher levels of specificity than adenoviruses in which only one gene was under control of a prostate-specific TRE; and mediate cell-specific adenoviral replication in cytopathic assays, plaque assays. and in in vivo tests on prostatic xenografts in athymic mice.

Adenovirus CN739, as described in Example 1.F., comprises a whole adenovirus in which a PB-TRE controls expression of E1A and PSA-TRE controls expression of E1B.

In adenovirus CN753, described in detail below, a PB-TRE controls expression of E1B, and a PSA-TRE controls E1A. In other adenovirus vectors, E1A was placed under control of a PB-TRE or PSA-TRE by inserting a PB-TRE or PSA-TRE between the native (wt) E1A promoter and the E1A coding segment, thus creating the sequence: native E1A promoter/PB-TRE (or PSA-TRE)/ E1A coding segment. In CN753, the native E1A promoter was deleted, yielding the E1A coding segment under sole control of a prostate-specific enhancer.

CN753 was generated in several steps: The native E1A promoter was deleted (as a 64 bp fragment) from CN 124 (wild-type left-hand end of Ad5) to generate CN306. The PSA-TRE fragment (from plasmid CN143, described above) was then inserted upstream of the promoter-less E1A coding segment of CN306 to generate CN321. A PB-TRE fragment (described above) was then inserted into the EagI site between the E1B promoter and E1B coding segment to generate CN326. CN326 thus has E1A under sole control of PSA-TRE and E1B undercontrol of PB-TRE. CN326 was then homologously recombined with BHG 11, which contains the right hand side of Ad5 to generate CN753. The recombination was performed under a protocol similar to that outlined in 1. F.

5. B. Plaque Assay Demonstrating Prostate Cell Specificity of Adenovirus in which Multiple Adenonviral Genes are Under Control of Prostate-specific TREs Plaque assays were performed to determine the cell-specificity of adenoviruses in which multiple adenoviral genes are under control of prostate-specific TREs. A plaque assay is an infectious assay that quantifies how efficiently a particular virus produces an infection in a cell line. Plaquing efficiency was evaluated in the following cell types: prostate tumor cell lines (LNCaP, PC-3), breast normal cell line (HBL-100), ovarian tumor cell line (OVCAR-3), and human embryonic kidney cells (293).

The adenoviruses tested were:

CN702, wt. in which E1A and E1B are under control of their native promoters.
CN706, in which a PSA-TPE controls E1A expression.
CN739, in which a PB-TRE controls E1A expression and a PSA-TRE controls E1B.
CN753, in which a PSA-TRE controls E1A, and a PB-TRE controls E1B.

The plaque assay was performed as follows: Confluent cell monolayers were seeded in 6 well dishes eighteen hours before infection. The monolayers were infected with 10-fold serial dilutions of each virus. After infecting monolayers for four hours in serum-free media (MEM), the media was removed and replaced with a solution of 0.75% low melting point agarose and tissue culture media. Plaques were scored two weeks after infection. CN702 has no modifications in its E1 region and is used as a wild-type control.

TABLE 2

PSA-TRE and PB-TRE engineered adenovirus plaque assay data. Percent of wild-type adenovirus (PFU/ml)

| | Cell Lines | | | |
|---|---|---|---|---|
| Viruses | 293 | LNCaP | HBL-100 | OVCAR-3 |
| CN702 | 100 | 100 | 100 | 100 |
| CN706 | 100 | 33 | 2.5 | 3.4 |
| CN739 | 100 | 35 | 0.12 | 0.0023 |
| CN753 | 100 | 41 | 0.23 | 0.11 |

Table 2 shows the average titer of duplicate samples for the viruses tested. The titer for a particular virus in all cell lines was normalized to its titer on 293 cells. This allows comparisons to be made between viruses in a particular cell type. Once the titers on a cell type were normalized to 293 cells. the normalized numbers of the recombinant viruses were compared to CN702. A ratio of less than 100 suggests that the virus tested plaques less efficiently than CN702. Conversely, a ratio greater than 100 suggests that the virus plaques more efficiently than CN702.

Several interesting observations can be made from this plaque assay. First, adenoviruses in which two adenoviral replication genes are controlled by a PSA-TRE and a PB-TRE demonstrated replication in prostate tumor cells, although this replication shows a slightly lower efficiency than wild type adenovirus.

Second, adenoviruses in which two adenoviral replication genes are controlled by PSA-TRE and PB-TRE demonstrated an unexpectedly high preferential replication in prostate tumor cells. The virus CN706, in which a PSA-TRE controls E1A, showed a 29-fold increase in replication cell-specificity. When two prostate-specific promoters, a PSA-TRE and a PB-TRE, controlled transcription of E1A and E1B, the specificity increased 800-fold (for CN753) or over 40,000-fold in OVCAR-3 cells. Similarly, the adenoviruses comprising two prostate-specific TREs demonstrated significantly better specificity of replication in HBL-100 cells. This increase in specificity is more than an additive effect of inserting a second prostate-specific TRE.

A significant result shown in Table 2 was that viral replication of CN739 proved much more specific than that of CN753. In both of these viruses. two adenovirus replication genes, E1A and E1B, are controlled by prostate-specific TREs, a PB-TRE or a PSA-TRE. E1A is arguably more important for viral replication than E1B, as E1A is expressed before any other viral genes, including E1B. and is required for E1B expression. Flint (1982); Flint (1986); Grand (1987). CN753, in which a PSA-TRE controls expression of E1A. demonstrated an 800-fold increase in cell-specific replication in OVCAR-3 cells. CN739, in which PB-TRE controls expression of E1A, showed a greater 40,000-fold increase. This result suggests that, under at least some conditions, PB-TRE has a much greater ability to regulate cell-specific replication than a TRE derived from the prostate specific antigen gene.

Third, PSA-TRE and PB-TRE viruses give 10- to 100- fold less plaques in HBL-100 and OVCAR-3 cells than CN706, but their titers were similar to CN706 in LNCaP cells. PSA-TRE and PB-TRE engineered viruses were significantly attenuated relative to wild-type adenovirus and CN706 in non-prostate cells, but they showed similar activity to CN706 in LNCaPs. While the adenoviruses containing prostate-specific TREs showed an ability to replicate in prostate cells decreased up to three-fold, this occurred simultaneously with the achievement of a greatly increased specificity (up to 1,000-fold).

Thus, an adenovirus in which one adenoviral gene was under control a prostate-specific TRE showed great specificity to prostate cells. but adenoviruses in which two adenoviral genes were under control of two separate prostate-specific promoters showed even greater specificity, in plaque assays.

5. C. Cytopathic Effects Assay Demonstrating Prostate Cell Specificity of Denovirus in which Multiple Adenoviral Genes are Under Control of Prostate-specific TREs The cytopathic effects assay (CPE) was also used to determine the cell-specificity of replication of adenoviruses in which multiple adenoviral genes were placed under control of prostate-specific TREs.

The adenoviruses tested were:

CN702, in which E1A and E1B are under control of their native promoters; and

CN739, in which PB-TRE controls E1A expression and PSA-TRE controls E1B.

CPE assays were performed as follows: Cells were infected with virus at increasing multiplicities of infection (MOI) and monitored for cytopathic effect. Assays were terminated when complete cytolysis of the monolayers was observed at an MOI of 0.01 with wild-type adenovirus. One primary, non-immortalized human microvascular endothelial cell line was chosen to test its sensitivity to CN739 and wild-type adenovirus (CN702) infection, in vitro. CN702 caused complete monolayer cytolysis of hMVECs (primary human microvascular endothelial cells) at MOIs as low as 0.01 within 10 days. In contrast, CN739-infected hMVEC monolayers did not show significant cytopathic effects at the same time points with MOIs of 10, 1.0, 0.1 and 0.01. Cytolysis of hMVECs equivalent to that seen with wild-type adenovirus was only evident at MOIs between 100 and 1000 times as high (MOI>10).

Thus, CN739-mediated cytolysis is significantly attenuated relative to wild-type adenovirus in primary normal human cells.

5. D. Differential Viral Replication

Figure 6:
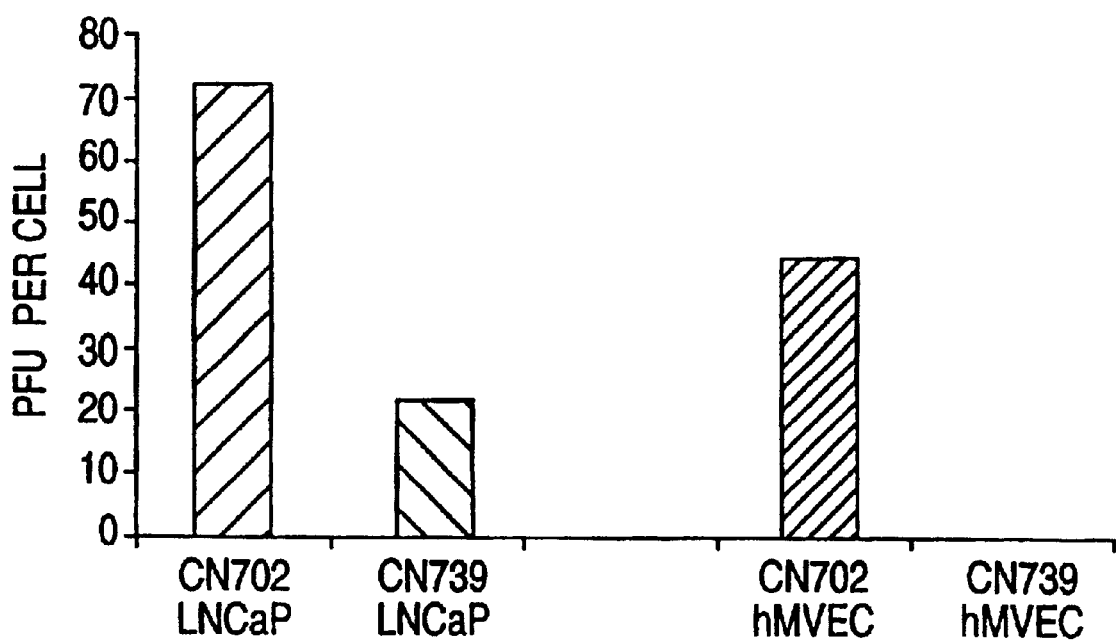
FIG. 6 is a bar graph demonstrating the reduced replication in non-prostate cells of an adenovirus, CN739, in which multiple adenoviral early genes are placed under control of prostate-specific TREs.

In order to determine if levels of virus replication correlate with the cytopathic effects of CN739 in prostate tumor cells or human normal cells, we carried out virus replication titration on PSA-producing prostate tumor cells (LNCaP) and non-prostate cells, primary human microvascular endothelial cells (hMVECs). Cells were grown to 70–90% confluence and infected With either wild-type adenovirus (CN702) or CN739 for 90 min at a MOI of 10. Fifty-five hours after infection, the virus was released from the cells by three freeze/thaw cycles, and the resulting supernatant was titered on 293 cells. The amount of CN739 produced was normalized against the amount of wild-type virus produced in the same cell line during the same time period. The data shown in FIG. 6 indicate that CN739 titers were 30% of CN702 titers in LNCaPs. but were reduced to less than ¹⁄₁₀₀the those of the wild-type virus in normal (hMVEC) cells. This suggests that CN739 replicates poorly in primary normal human cells, and is only slightly attenuated in prostate cancer cells.

In short, an adenovirus in which multiple adenoviral genes were under control of prostate-specific TRFs demonstrated replication in prostate cells, and only very poor replication in non-prostate endothelial cells.

5. E. One-step Growth Curve

Figure 7A:
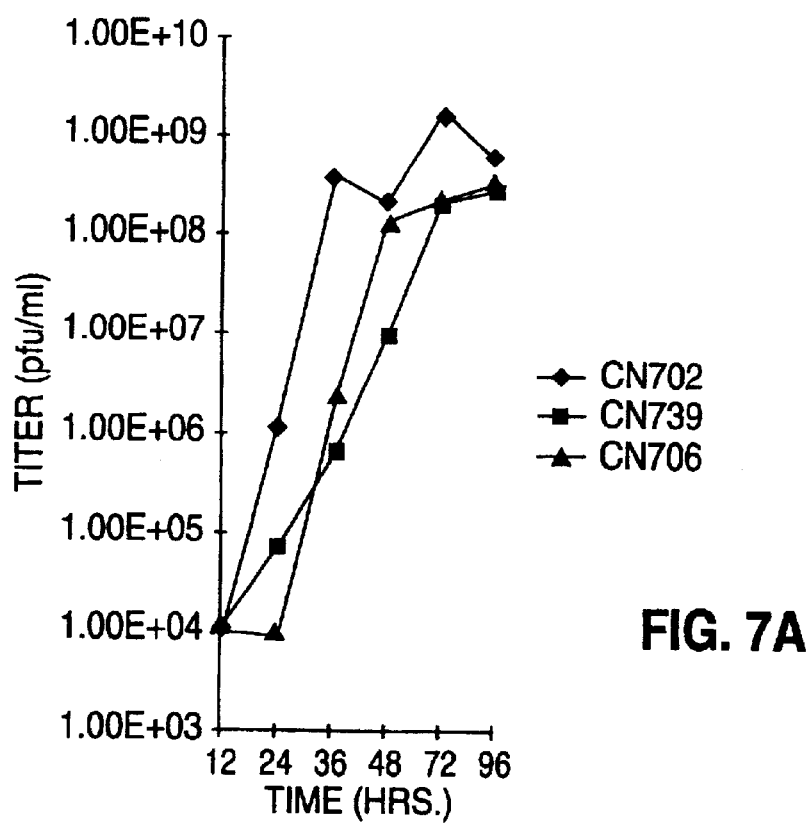
FIGS. 7A and 7B are line graphs illustrating the one-step growth of an adenovirus, CN739, in which multiple adenoviral early genes are placed under control of prostate-specific TREs in prostate (LNCaP, FIG. 7A) and non-prostate cells (hMVEC, FIG. 7B).
Figure 7B:
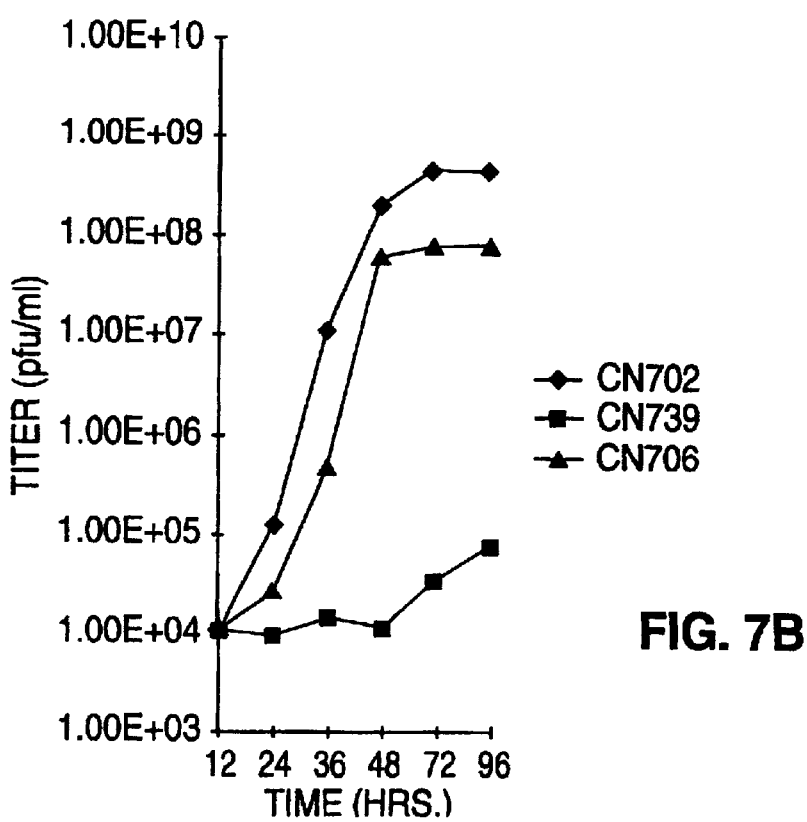

A one-step growth curve assay was used to determine the efficiency and kinetics of replication of various adenoviruses in prostate and non-prostate endothelial cells. Viruses used were CN702 (wt), CN706 (PSA-TRE controlling E1A expression), and CN739 (PB-TRE controlling E1A and PSA-TRE controlling E1B). Cells used were LNCaPs (prostate tumor cells) and hMVECs (primary human microvascular endothelial cells). Replicate monolayers of LNCaPs and hMVECs were infected at a MOI of 10 to obtain a synchronous infection of all the cells. Duplicate cultures were harvested at various times post-infection. The number of infectious virus was determined by plaque assay on 293 cells (FIG. 7). CN739 and CN706 grew at a similar efficiency in LNCaPs. However, under identical conditions. CN739 grew poorly in the hMVECs, producing about 1 0,000-fold and 80,000-fold less infectious virus than CN706 and wild-type adenovirus, respectively.

Thus, the one-step growth curve demonstrated that viruses in which multiple adenoviral genes were under control of prostate-specific TREs grew well in prostate tumor cells, but grew very poorly in non-prostate endothelial cells. indicating significantly enhanced specificity.

5. F. Therapeutic Effect Studies

The efficacy of treating prostate tumors in vivo was tested with an adenovirus in which multiple genes were under control of two separate prostate-specific TREs, a PB-TRE and a PSA-TRE (CN739). To examine the therapeutic efficacy of CN739 in vivo, LNCaP (prostate tumor) xenografts were grown in athymic mice. The tumor cells were injected subcutaneously into each flank of each mouse, and after establishment of palpable tumors (mean tumor volume 300 mm³), the tumors were directly injected with CsCl-purified CN739 at $2.5 \times 10^8$ particles per $mm^3$, or PBS containing 10% glycerol (vehicle) as a control. Tumor growth was then followed for 6 weeks, at which time the mean tumor volume in each group was determined and serum samples were collected for PSA analysis on day 0 and weekly thereafter.

Figure 9:
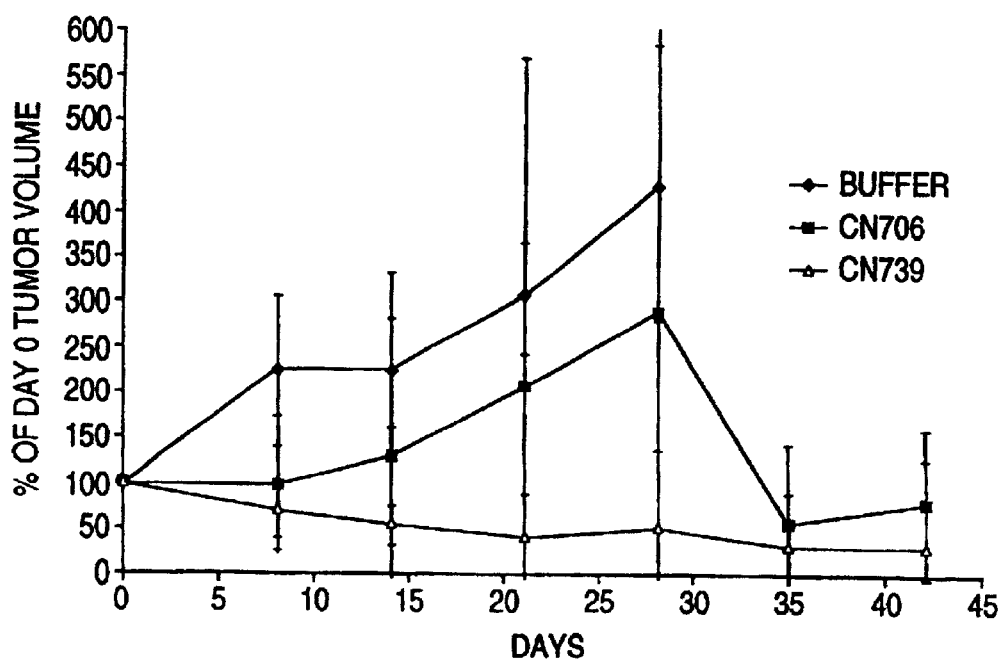
FIG. 9 is a line graph illustrating the efficacy in treating a prostate cancer tumor in mice of an adenovirus, CN739, in which multiple adenoviral early genes are placed under control of prostate-specific TREs.

The data depicted in FIG. 9 show that treatment of LNCaP tumors with CN739 resulted in an 80% reduction in average tumor volume whereas the average tumor volume in vehicle-treated group 1, at day 28, had increased to 400% of the initial volume. Four of seven (57%) animals in CN739-treated group II were free of palpable tumors at day 42. This study demonstrates that a fixed, single dose of an adenovirus in which multiple genes are under control of prostate-specific TREs (CN739) per tumor is efficacious against LNCaP xenografts in vivo.

5. G. Effects on Serum PSA Levels

The serum PSA level is a widely-used marker for the diagnosis and management of prostate carcinoma. LNCaP cells express and secrete high levels of PSA into the culture media and into circulation. An experiment was designed to examine the effects of treatment with CN739 (an adenovirus in which multiple genes were under control of prostate-specific TREs PB-TRE and PSA-TRE) on the serum PSA concentration in mice with LNCaP tumor xenografts.

Figure 8:
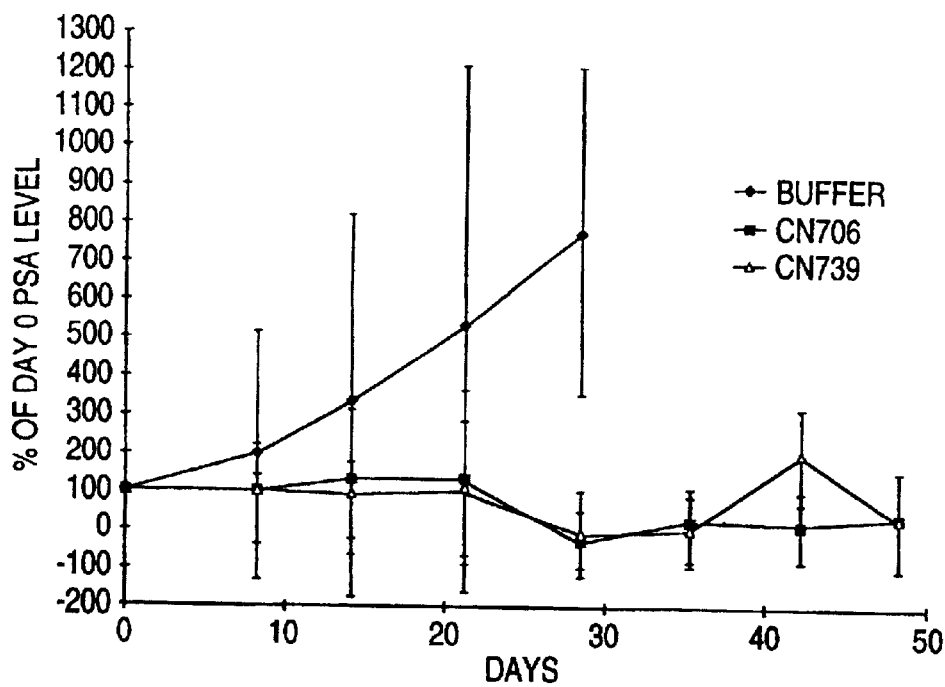
FIG. 8 is a line graph showing serum PSA levels in mice treated with an denovirus, CN739, in which multiple adenoviral early genes are placed under control of prostate-specific TREs.

Following treatment, the average serum PSA level in control group I (vehicle only) increased to approximately 800% of the initial value by day 28, whereas the average PSA level in group II (CN706 treatment) and group III (CN739 treatment) remained essentially constant through day 21 and declined to 10% of the initial value by day 35 (FIG. 8). There was a statistically significant difference ($p<0.001$; T-test) between group I and group II on day 14 and thereafter.

These results demonstrate that CN739 treatment is efficacious in the LNCaP xenograft model when the outcome is measured either by reduction in tumor growth or serum PSA concentration. Taken together with the in vitro data, it suggests that adenoviruses with a single adenoviral gene under control of a prostate-specific TRE such as PB-TRE are able to mediate prostate cell-specific viral replication. Placing a second adenoviral gene under control of a separate prostate-specific TRE further increases the cell-specificity.

Example 6

Characterization of an E3 Deleted Adenovirus, CN751, that Contains the Adenovirus Death Protein Gene An adenovirus comprising an adenovirus death protein, CN751, was constructed to test whether such a construct may be more effective for cytotoxicity. The adenovirus death protein (ADP), an 11.6-kDa Asn-glycosylated integral membrane peptide expressed at high levels late in infection, migrates to the nuclear membrane of infected cells and affects efficient lysis of the host. The Adenovirus 5 (Ad5) E3 region expresses the adp gene.

Construction of CN751

CN75 1 was constructed in two parts. First, an E3 deleted platform plasmid that contains Ad5 sequence 3' from the BamHI site at 21562bp was generated. The Ad2 adp was engineered into the remainder of the E3 region of this plasmid to yield CN252 (this cloning has been previously described). To construct the second part, the 5' Ad5 sequence necessary for CN751 was obtained by digesting purified CN702 DNA with EcoRI and isolating the left hand fragment by gel extraction. After digesting CN252 with EcoRI, the left hand fragment of CN702 and CN252 were ligated. 293 cells were transfected with this ligation mixture by lipofection transfection and incubated at 37° C. Ten days later, the cells were harvested, freeze-thawed three times, and the supernatant was plaqued on 293 monolayers. Individual plaques were picked and used to infect monolayers of 293 cells to grow enough virus to test. After several days, plate lysates were screened using a polymerase chain reaction (PCR) based assay to detect candidate viruses. One of the plaques that scored positive was designated CN751.

Structural Characterization of CN751

The structure of CN751 was confirmed by two methods. First, primers 37.124.1 (5' gccttaattaaaagcaaacctcacctccg Ad2 28287bp) and 37.124.4 (5' ggcttaattaactgtgaaag-gtgggctgc Ad2 29872bp) were used to screen candidate viruses by PCR to detect the presence of the adp cassette. CN751 produced an extension fragment consistent with the expected product (1065bp). Second, CN751 was analyzed by Southern blot. Viral DNA was purified, digested with PacI, SacI, and AccI/XhoI, and probed with a sequence homologous to the ADP coding region. The structure of CN751 matched the expected pattern.

In Vitro Characterization of CN751

Two experiments were conducted to examine the cytotoxicity and virus yield of CN751. In the first study, CN751's cytotoxicity was evaluated in LNCaP cells by measuring the accumulation of a cytosolic enzyme, lactate dehydrogenase (LDH), in the supernatant over several days. The level of extracellular LDH correlates with the extent of cell lysis. Healthy cells release very little, if any, enzyme, whereas dead cells release large quantities. LDH was chosen as a marker because it is a stable protein that can be readily detected by a simple protocol. CN751's ability to cause cell death was compared to that of CN702, a vector lacking the ADP gene. and Rec700, a vector containing the ADP gene.

Monolayers of LNCaP cells were infected at an MOI of one with either CN702, Rec700 (adp+control), or CN751 and then seeded in 96 well dishes. Samples were harvested once a day from one day after infection to five days after infection and scored using Promega's Cytotox 96 kit. This assay uses a coupled enzymatic reaction which converts a tetrazolium salt to a red formazan product that can be determined in a plate reader at 490 nm.

Figure 10:
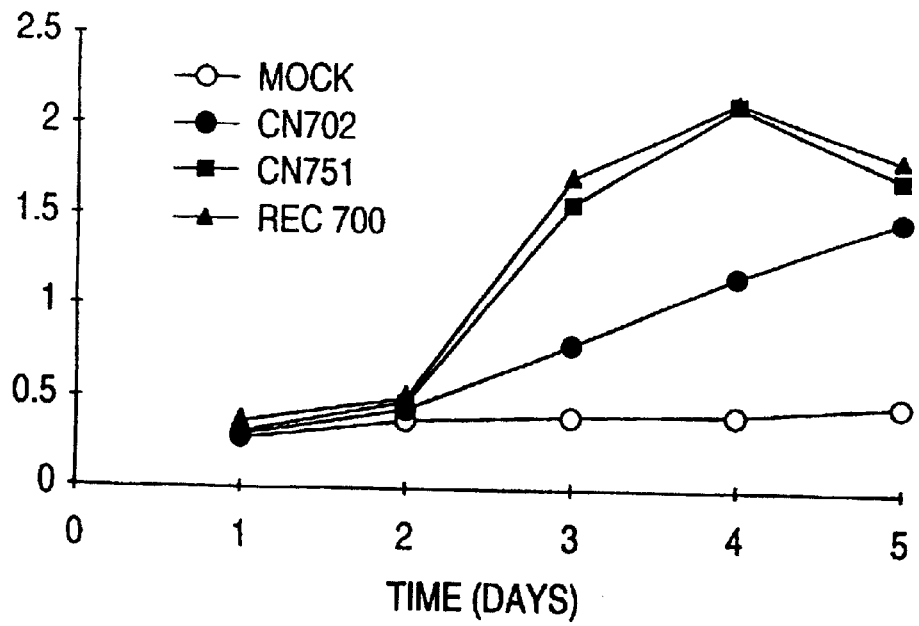
FIG. 10 is a graph depicting cytotoxicity of an adenoviral vector containing the coding sequence for adenoviral death protein (ADP), CN751 (solid squares), compared to control CN702 (solid circles), Rec 700 (solid triangles) and mock infection (Xs).

Since the absorbance of a sample corresponds to the level of LDH released from infected cells, a plot of how a sample's absorbance changes with time describes how efficiently the viruses studied induce cell lysis (FIG. 10). Each data point represents the average of sixteen separate samples. The results suggest that CN751 kills cells more efficiently than the adp– control, CN702, and similarly to the adp+control, Rec700. The concentration of LDH in the supernatant increases rapidly from two days and reaches a maximum at four days in wells infected with CN751. In contrast, LDH concentration in the supernatant of CN702 infected cells begins to rise slowly at two days and continues until the conclusion of the experiment. Significantly, the amount of LDH released from CN751 infected cells at three days is two times that released from CN702 infected cells. In sum, the virus yield data demonstrate that adenoviral vectors with the ADP gene release more virus.

Figure 11:
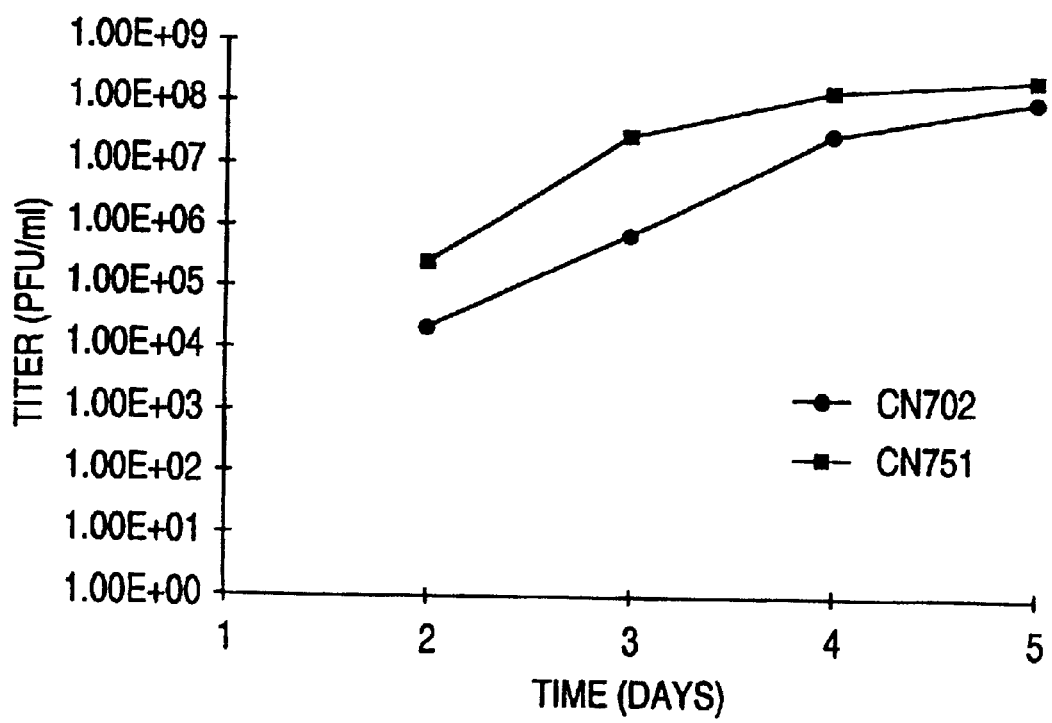
FIG. 11 is a graph comparing extracellular virus yield of CN751 (solid squares) and CN702 (solid circles).

Not only is it important for Ad vectors to kill cells efficiently, they must also be able to shed progeny that can infect other cancer cells. Viral vectors that can shed large amounts of virus might be better therapeutics than those that shed only small amounts. A virus yield assay was undertaken to evaluate whether CN751 can induce the efficient release of its progeny from the infected cell. A549 cells were infected at an MOI of five. Supernatant was harvested at various times after infection and titered on 293 cells to determine the virus yield (FIG. 11). The data suggest that cells infected with CN751 shed virus more efficiently than those infected with CN702. At forty-eight hours post infection, CN751 infected cells released ten times more virus than CN702 infected. At seventy-two hours post infection, CN751 infected cells released forty times more virus. The data demonstrate that adenoviral vectors with the ADP gene kill cells more efficiently than adenoviral vectors that lack the ADP gene.

In vivo characterization of CN751

Figure 12:
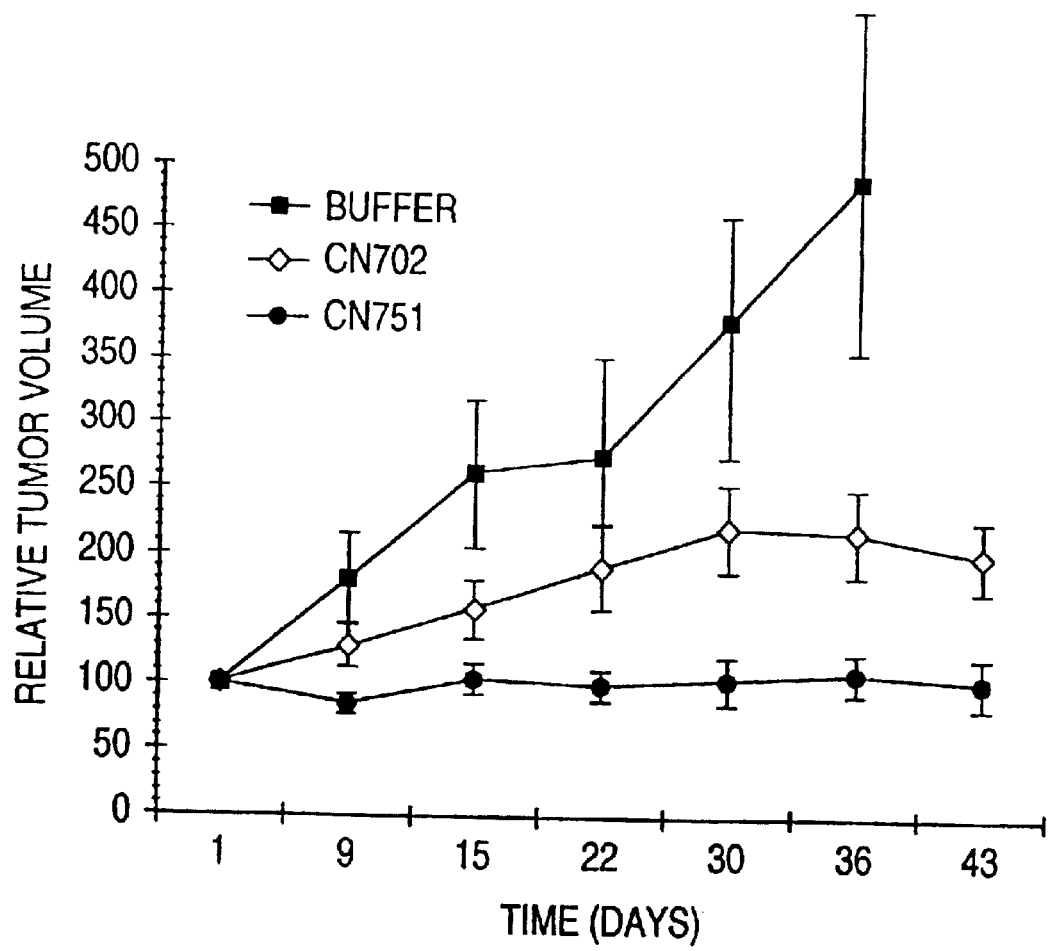
FIG. 12 is a graph comparing tumor volume in mice harboring LNCaP tumor xenografts challenged with CN751 ("H"), CN702 ("J"), or buffer ("B").

LNCaP nude mouse xenografts were challenged with a single intratumoral dose ($1 \times 10^4$ particles/mm$^3$ tumor) of either CN751, a vector containing the ADP gene, or CN702, a vector lacking the gene. A third group of tumors was treated with buffer alone. The tumors were monitored weekly for six weeks and their relative volume was graphed against time. The results are shown in FIG. 12. Error bars represent the standard error for each sample group. The initial average tumor volume for CN751 treated animals (n=14) was 320 mm$^3$ for CN702 treated (n=14), and 343 mm$^3$ for buffer treated (n=8). The data suggest that CN751 kills tumor cells more effectively than CN702. On average, tumors challenged with CN751 remained the same size throughout the course of the experiments while nine out of fourteen tumors (64%) regressed. Those treated with CN702 doubled in size. Buffer treated tumors grew to nearly five times their initial volume. The Students T-test indicates that the difference in tumor size between CN751 and CN702 treated tumors was statistically significant from day 7 (p=0.016) through the end of the experiment (p=0.003).

Example 7

A PB-TRE Demonstrates Higher Cell-specificity of Replication than a Human Glandular Kallikrein-1 TRE 6. A. Adenoviral Vectors Used in this Example Include:

CN702 (wt);

CN706, in which a PSA-TRE controls E1A expression;

CN753, in which a PSA-TRE controls E1A expression and a PB-TRE controls E1B; and CN755, in which a PSA-TRE controls E1A expression and a hKLK2-TRE (from the human glandular kallikrein-1 gene) controls E1B expression.

Plaque assays were performed to determine the cell-specificity of these adenoviruses. Plaquing efficiencies were evaluated on the following cell types: human embryonic kidney cell line (293), prostate tumor cell line (LNCaP), breast normal cell line (HBL-100). and ovarian tumor cell line (OVCAR-3). The plaque assays were performed as described above.

TABLE 3

PSA-TRE-, PB-TRE- and hKLK2-engineered adenovirus plaque assay data.
Percent of wild-type adenovirus (PFU/ml)

| Viruses | Cell Lines | | | |
|---|---|---|---|---|
| | 293 | LNCaP | HBL-100 | OVCAR-3 |
| CN702 | 100 | 100 | 100 | 100 |
| CN706 | 100 | 25 | 2.7 | 7.7 |
| CN753 | 100 | 33 | 0.067 | 0.11 |
| CN755 | 100 | 29 | 0.52 | 0.6 |

Table 3 shows the average titer of samples for the viruses tested. The titer for a particular virus in all cell lines was normalized to its titer on 293 cells. This allows comparisons to be made between viruses in a particular cell type. Once the titers on a cell type were normalized to 293 cells, the normalized numbers of the recombinant vectors were compared to CN702. A ratio of less than 100 suggests that the virus tested plaques less efficiently than CN702. Conversely, a ratio greater than 100 suggests that the virus plaques more efficiently than CN702.

Several interesting observations can be made from this plaque assay. First, this assay reiterates the unexpected finding described above that an adenovirus in which more than one adenovirus gene is under control of a prostate-specific TRE displays much a more than additive cell-specificity than an adenovirus in which only one adenovirus gene is under control of a prostate-specific TRE.

Second, CN753 demonstrates a significantly higher cell-specificity than CN755. In both CN753 and CN755, a PSA-TRE controls expression of E1A. However, in CN753, a PB-TRE controls expression of E1B, while in CN755, an hKLK2-TRE controls E1B. CN753 demonstrates a 5-fold higher cell-specificity in ovarian cells, and an 8-fold higher specificity in breast cells. Thus, it appears that, while both a PB-TRE and an hKLK2-TRE are thought to be specific for prostate cells, a PB-TRE, under at least some conditions, has a significantly higher specificity to prostate cells than an hKLK2-TRE.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A replication-competent adenovirus vector comprising a first adenovirus gene under transcriptional control of a probasin transcriptional regulatory element (PB-TRE) and a second adenovirus gene under transcriptional control of a different transcriptional regulatory element.

2. The adenovirus vector of claim 1, wherein the first and second adenovirus genes are essential for viral replication.

3. The adenovirus vector of claim 1, wherein the PB-TRE comprises an enhancer from a probasin gene.

4. The adenovirus vector of claim 1, wherein the PB-TRE comprises a promoter from a probasin gene.

5. The adenovirus vector of claim 1, wherein the PB-TRE comprises a promoter from a probasin gene and an enhancer from a probasin gene.

6. The adenovirus vector of claim 1, wherein the PB-TRE comprises at least one androgen response element (ARE).

7. The adenovirus vector of claim 1, wherein the PB-TRE comprises androgen response elements 1 and 2 (ARE-1 and ARE-2) of a probasin gene.

8. The adenovirus vector of claim 1, wherein the PB-TRE comprises nucleotides about 141 to about 454 of SEQ ID NO:1.

9. The adenovirus vector of claim 1, wherein the PB-TRE comprises nucleotides about 191 to about 204 or about 286 to about 310 of SEQ ID NO:1.

10. The adenovirus vector of claim 1, wherein the PB-TRE comprises the sequence of SEQ ID NO:1.

11. A composition comprising an adenovirus vector of claim 1 and a pharmaceutically acceptable excipient.

12. The adenovirus vector of claim 1, wherein said different transcriptional regulatory element comprises a prostate-specific transcriptional regulatory element.

13. The adenovirus vector of claim 1, wherein said different TRE comprises a human glandular kallikrein TRE (hKLK2-TRE).

14. A host cell transformed with an adenovirus vector of claim 1.

15. A method for selective cytolysis of a target cell, said method comprising:

contacting a cell with an adenovirus vector of claim 1, wherein the adenovirus vector enters the cell and the transcriptional regulatory elements (TREs) are functional in the cell and expression of said adenovirus gene under control of said PB-TRE contributes to selective cytotoxicity.

16. A method of suppressing tumor cell growth, said method comprising contacting a tumor cell with an adenoviral vector of claim 1 such that the adenoviral vector enters the tumor cell and exhibits selective cytotoxicity for the tumor cell.

17. The adenovirus of claim 2, wherein said first adenovirus gene is a late gene.

18. The adenovirus vector of claim 2, wherein said first adenovirus gene is E1A or E1B.

19. The adenovirus vector of claim 2, wherein said second adenovirus gene is E1A or E1B.

20. The adenovirus of claim 2, wherein said second adenovirus gene is a late gene.

21. The adenovirus vector of claim 12, wherein said prostate-specific transcriptional regulatory element comprises a prostate-specific antigen (PSA) transcriptional regulatory element.

22. A composition comprising an adenovirus vector of claim 12 and a pharmaceutically acceptable excipient.

23. A host cell transformed with an adenovirus vector of claim 12.

24. A method for selective cytolysis of a target cell, said method comprising:

contacting a cell with an adenoviral vector of claim 12, wherein the adenovirus vector enters the cell and the transcriptional regulatory elements (TREs) are functional in the cell and expression of said adenovirus gene under control of said PB-TRE contributes to selective cytotoxicity.

25. A method of suppressing tumor cell growth, said method comprising contacting a tumor cell with an adenoviral vector of claim 12 such that the adenoviral vector enters the tumor cell and exhibits selective cytotoxicity for the tumor cell.

26. A host cell transformed with an adenovirus vector of claim 13.

* * * * *